(12) United States Patent  (10) Patent No.: US 8,946,264 B2
Shinozuka et al.  (45) Date of Patent: Feb. 3, 2015

(54) PYRIDINE DERIVATIVE

(71) Applicant: Daiichi Sankyo Company, Limited, Tokyo (JP)

(72) Inventors: Tsuyoshi Shinozuka, Tokyo (JP); Tomoharu Tsukada, Tokyo (JP); Kunihiko Fujii, Tokyo (JP); Makoto Mori, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/656,664

(22) Filed: Oct. 20, 2012

(65) Prior Publication Data
US 2013/0045994 A1 Feb. 21, 2013

Related U.S. Application Data

(63) Continuation of application No. 13/088,103, filed on Apr. 15, 2011, now abandoned, which is a continuation of application No. PCT/JP2010/053384, filed on Mar. 3, 2010.

(30) Foreign Application Priority Data

Mar. 5, 2009 (JP) .................................. 2009-051820

(51) Int. Cl.
A61K 31/4439 (2006.01)
C07D 401/12 (2006.01)

(52) U.S. Cl.
CPC .................................... C07D 401/12 (2013.01)
USPC ........................................ 514/338; 546/273.4

(58) Field of Classification Search
USPC ........................................ 546/273.4; 514/338
See application file for complete search history.

(56) References Cited

U.S. PATENT DOCUMENTS

| 5,002,953 | A | 3/1991 | Hindley |
| 5,968,960 | A | 10/1999 | Schwartz |
| 5,972,968 | A | 10/1999 | De Nanteuil |
| 6,353,009 | B1 | 3/2002 | Fujiwara et al. |
| 6,630,598 | B2 | 10/2003 | Yoshida |
| 6,706,746 | B2 | 3/2004 | Fujita et al. |
| 7,232,828 | B2 | 6/2007 | Pershadsingh |
| 7,812,046 | B2 | 10/2010 | Pershadsingh |
| 7,867,991 | B2 | 1/2011 | Pershadsingh |
| 8,106,079 | B2 | 1/2012 | Kajino et al. |
| 8,263,631 | B2 | 9/2012 | Fujiwara et al. |
| 2003/0069294 | A1 | 4/2003 | Fujita et al. |
| 2004/0002512 | A1 | 1/2004 | Fujita et al. |
| 2004/0122237 | A1 | 6/2004 | Amiri et al. |
| 2005/0250831 | A1 | 11/2005 | Gibson et al. |
| 2007/0185070 | A1 | 8/2007 | Pershadsingh |
| 2008/0009536 | A1 | 1/2008 | Pershadsingh |
| 2008/0242712 | A1 | 10/2008 | Pershadsingh |
| 2010/0048564 | A1 | 2/2010 | Shimada et al. |
| 2012/0029026 | A1 | 2/2012 | Shinozuka |

FOREIGN PATENT DOCUMENTS

| JP | 2000-351769 A | 12/2000 |
| JP | 2002-193948 A | 7/2002 |
| JP | 2004-067629 A | 3/2004 |
| JP | 2004-315404 A | 11/2004 |
| JP | 2005-523292 A | 8/2005 |
| WO | WO 00/59889 A1 | 10/2000 |
| WO | WO 2004/013109 A1 | 2/2004 |
| WO | WO 2004/014308 A2 | 2/2004 |
| WO | WO-2005/042497 | 10/2004 |
| WO | WO 2005/037763 A1 | 4/2005 |
| WO | WO 2006/025783 A1 | 3/2006 |
| WO | WO 2007/084786 A1 | 7/2007 |
| WO | WO 2008/126732 A1 | 10/2008 |

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982.*
Martinic et al., "Real-time imaging, etc.," Immunological Reviews 2008, 22: 200-213.*

(Continued)

Primary Examiner — Patricia L Morris
(74) Attorney, Agent, or Firm — Locke Lord, LLP

(57) ABSTRACT

The present invention relates to a novel pyridine derivative or a pharmacologically acceptable ester thereof, or a pharmacologically acceptable salt of the derivative or ester, which has an excellent hypoglycemic effect or treats and/or prevents the onset of a disorder of carbohydrate or lipid metabolism or a disease mediated by peroxisome proliferator-activated receptor (PPAR) γ. A compound represented by the general formula (I):

[Formula 1]

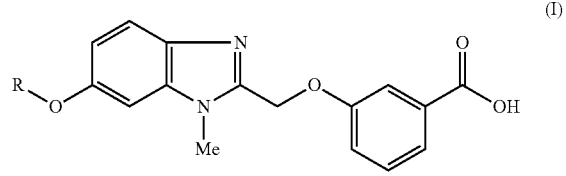

[wherein R represents a pyridyl group substituted with 1 to 3 group(s) independently selected from Substituent Group A, and Substituent Group A represents a halogen atom, a $C_1$-$C_6$ alkyl group and a $C_1$-$C_6$ alkoxy group] or a pharmacologically acceptable ester thereof, or a pharmacologically acceptable salt of the compound or ester.

17 Claims, No Drawings

(56) References Cited

OTHER PUBLICATIONS

Leff et al., "Review: Peroxisome, etc.," Experimental Diab, Res., 5:99-109, 2004.*
Subramani et al., "The Need for Physiologically, etc.," Endocring, Metabolic & Immune Disorders-Drug Targets, 2013, 13, 175-183.*
Willson et al., Peroxisome Proliferator, etc., Annu. Rev. Biochem., 2001 70: 341-367.*
Savkur et al., "Investigational PPAR, etc.," Expert Opin. Investig. Drugs (2006), 15(7) 763-778.*
U.S. Appl. No. 13/418,796, filed Mar. 13, 2012, Kousei Shimada et al.
Bélanger, Patrice C. et al., "Facile preparations of 4-fluororesorcinal," Can. J. Chem., 66, pp. 1479-1482, 1988.
Greene, T.W. et al., "Protective Groups in Organic Synthesis", 3rd Edition, John Wiley & Sons, Inc. (1999) (Chapters 2, 5, and 7 in particular).
Horning, E.C. et al., "Furocoumarins: Synthesis of 2,3-Dihydropsoralene," J. Am. Chem. Soc., 70, pp. 3619-3620, Nov. 1948.
Kato, S., Homo sapiens mRNA for PPAR gamma2, complete cds, GenBank: D83233.1, 1999.
Lambe, K.G., "H.sapiens mRNA for peroxisome proliferactor activated receptor gamma," GenBank: X90563.1, Eur. J. Biochem. 239:1, pp. 1-7, 1996.
Lehmann, Jürgen M. et al., "An Antidiabetic Thiazolidinedione Is a High Affinity Ligand for Peroxisome Proliferator-activated Receptor γ (PPARγ)," Journal of Biological Chemistry, 270:22, pp. 12953-12956, Jun. 2, 1995.
Tugwood, J.D. et al., "The Mouse peroxisome proliferator activated receptor recognizes a response element in the 5' flanking sequence of the rat acyl CoA oxidase gene," The EMBO Journal, 11:2, pp. 433-439, 1992.
Bundgaard, H., "Design of progrugs: Bioreversible derivatives for various functional groups and chemical entities," Design of Prodrugs, Elsevier Science Publishers B.V. (Biomedical Division), 7:1-92 (Chapter 1), 1985.

"The Molecular Design of Prodrugs," Development of Pharmaceutical Products, Molecular Design, Hirokawa Shoten Ltd., 7:163-164, and 186-190, 1990 (English Translation).
International Search Report for International Application No. PCT/JP2008/056541, Date of Mailing: May 20, 2008.
International Search Report for International Application No. PCT/JP2010/053384, Date of Mailing: Mar. 30, 2010.
Berger, Joel et al., "The Mechanisms of Action of PPARs," Annual Reviews of Medicine, 53, pp. 409-435, 2002.
Cantello, Barrie et al., "The Synthesis of BRL 49653—A Novel and Potent Antihyperglycaemic Agent," Biooraanic & Medicinal Chemistry Letters, 4:10, pp. 1181-1184, 1994.
Fujiwara et al., (1999): STN International HCAPLUS database, (Columbus, Ohio), Accession No. 1999:355581.
Jiang, Chengyu, et al., "PPAR-γ Agonists Inhibit Production of Monocyte Inflammatory Cytokines," Nature, 391, pp. 82-86, Jan. 1998.
Kapoor, Amit et al., "QSAR and Molecular Modeling Studies in Imidazo-Pyridinethiazolidine-2,4-Diones: PPARγ Agonists," Medical Chemistry Research, 13:8/9, pp. 770-780, 2004.
Momose, Yu et al., "Studies on Antidiabetic Agents. X. Synthesis and Biological Activities of Pioglitazone and Related Compounds," Chem. Pharm. Bull., 39:6, pp. 1440-1445, 1991.
Ricote, Mercedes et al., The Peroxisome Proliferator-Activated Receptor-γ is a Negative Regulator of Macrophage Activation, Nature, 391, pp. 79-82, Jan. 1998.
Sarabu, Ramakanth et al., "Recent Advances in Therapeutic Approaches to Type 2 Diabetes," Annual Reports in Medicinal Chemistry, 39, pp. 41-56, 2004.
Sternbach, Daniel et al., "Modulators of Peroxisome Proliferator-Activated Receptors (PPARs)," Annual Reports in Medicinal Chemistry, 38, pp. 71-80, 2003.
Tsubouchi, Yasunori et al., "Inhibition of Human Lung Cancer Cell Growth by the Peroxisome Proliferator-Activated Receptor-γ Agonists through Induction of Apoptosis," Biochemical and Biophysical Research Communications, 270, pp. 400-405, 2000.

* cited by examiner

PYRIDINE DERIVATIVE

This application is a continuation of U.S. application Ser. No. 13/088,103, filed Apr. 15, 2011, which is a continuation of International Application No. PCT/JP2010/053384, filed on Mar. 3, 2010, entitled "PYRIDINE DERIVATIVE", which claims the benefit of Japanese Patent Application Number JP 2009-051820, filed on Mar. 5, 2009, all of which are hereby incorporated by reference.

FIELD OF THE INVENTION

The present invention relates to a medicine, in particular, a novel pyridine derivative or a pharmacologically acceptable ester thereof, or a pharmacologically acceptable salt of the derivative or ester, which has a hypoglycemic effect or treats and/or prevents the onset of a disorder of carbohydrate or lipid metabolism or a disease mediated by peroxisome proliferator-activated receptor (PPAR) γ.

The present invention also relates to a therapeutic agent and/or prophylactic agent for diabetes (especially type II diabetes), hyperglycemia, hyperlipidemia, adiposity, impaired glucose tolerance, insulin resistance, impaired fasting glucose, cachexia, psoriasis, diabetic complications, arteriosclerosis, atherosclerosis, hypertension, pancreatitis, polycystic ovary syndrome, fatty liver, nonalcoholic steatohepatitis (NASH), gestational diabetes mellitus, inflammatory disease, cancer, osteoporosis, involutional osteoporosis, neurodegenerative disease, Alzheimer's disease, hyperuricemia, metabolic syndrome, or the like, which has an effect of improving carbohydrate or lipid metabolism, an effect of improving insulin resistance, an antiinflammatory effect or an effect of inhibiting the growth of cancer cells, the therapeutic agent and/or prophylactic agent comprising a novel pyridine derivative or a pharmacologically acceptable ester thereof, or a pharmacologically acceptable salt of the derivative or ester as an active ingredient.

BACKGROUND

In recent years, the number of patients with metabolic syndrome such as type II diabetes, hyperinsulinemia, dyslipidemia, adiposity, hypertension or atherosclerotic disease has been increasing around the world due to reasons such as changes in lifestyles. Patients with metabolic syndrome have a several-fold increased risk of coronary artery disease, cerebral infarction and cerebral hemorrhage and are further affected with chronic complications such as nephropathy, neuropathy and retinopathy. The increase in the number of patients with complications has been a major cause of rising medical costs (Non-Patent Document 1).

Recent researches have shown that ligands acting on PPARγ are useful for the prevention or improvement of a pathology called metabolic syndrome such as type II diabetes, hyperinsulinemia, dyslipidemia, adiposity, hypertension, atherosclerotic disease or insulin resistance (Non-Patent Document 2). Ligands acting on PPARγ inhibit the production of inflammatory cytokines (Non-Patent Documents 3 and 4) and induce apoptosis to inhibit the growth of cancer cells (Non-Patent Document 5). Therefore, the ligands are also useful for the prevention or improvement of inflammatory disease or cancer. Specific examples of the ligands activating PPARγ include pioglitazone (Non-Patent Document 6) and rosiglitazone (Non-Patent Document 7) classified into thiazolidinedione drugs already medically used in the treatment of type II diabetes. These thiazolidinedione drugs have side effects such as fluid retention, body weight increase and increased risks for heart disease. Therefore, safer pharmaceuticals have been desired to be developed (Patent Document 1). Many researchers have now been researching and developing pharmaceuticals with an aim to prevent or improve insulin resistance, diseases caused by inflammation or the like, or metabolic syndrome through researches of ligands activating or inhibiting PPARα, PPARγ or PPARδ (Non-Patent Document 8).

Patent Document 2 describes compounds having an alkoxy group, a (substituted) phenyloxy group, a pyridyloxy group or the like bonded to the 6-position of a benzimidazole group as derivatives having the same skeleton as in the compounds of the present invention, and use of those compounds as therapeutic agents for diabetes, hyperglycemia or the like. However, in the synthetic examples in this document, the sole pyridyloxy group at the 6-position of the benzimidazole group is an unsubstituted 3-pyridyloxy group. On the other hand, in the compounds of the present invention, a pyridyloxy group having 1 to 3 substituent(s) is bonded to the 6-position of a benzimidazole group.

Patent Document 1: WO 2004/014308
Patent Document 2: WO 2008/126732
Non-Patent Document 1: Annual Reports in Medicinal Chemistry, 39, 41-56 (2004)
Non-Patent Document 2: Annual Reviews of Medicine, 53, 409-435 (2002)
Non-Patent Document 3: Nature, 391, 79-82 (1998)
Non-Patent Document 4: Nature, 391, 82-86 (1998)
Non-Patent Document 5: Biochemical and Biophysical Research Communications, 270, 400-405 (2000)
Non-Patent Document 6: CHEMICAL & PHARMACEUTICAL BULLETIN, 39, 1440-1445 (1991)
Non-Patent Document 7: Bioorganic and Medicinal Chemistry Letter, 4, 1181-1184 (1994)
Non-Patent Document 8: Annual Reports in Medicinal Chemistry, 38, 71-80 (2003)

SUMMARY OF THE INVENTION

Problems to be Solved by the Invention

The present inventors have conducted extensive studies to develop therapeutic agents and/or prophylactic agents for disorders of carbohydrate or lipid metabolism or diseases mediated by peroxisome proliferator-activated receptor (PPAR) γ. Thus, the inventors have found that pyridine derivatives having a specific chemical structure have an excellent hypoglycemic effect or have an effect of improving carbohydrate or lipid metabolism, an effect of improving insulin resistance or an effect of improving so-called metabolic syndrome such as arteriosclerosis, hypertension, cardiovascular disorder or complications derived from them or a pathology caused by various inflammations. The inventors have further found that the compounds are ligands acting on peroxisome proliferator-activated receptor (PPAR) γ and therefore have an effect of inhibiting the growth of cancer cells. These findings have led to the completion of the present invention.

Specifically, the present invention provides novel pyridine derivatives or pharmacologically acceptable esters thereof, or pharmacologically acceptable salts of the derivatives or esters, which are useful as therapeutic agents or prophylactic agents for metabolic syndrome, specifically, diseases such as diabetes (especially type II diabetes), hyperglycemia, hyperlipidemia, adiposity, impaired glucose tolerance (IGT), insulin resistance, impaired fasting glucose (IFG), hypertension, fatty liver, nonalcoholic steatohepatitis (NASH), diabetic complications (such as retinopathy, nephropathy or neuropathy), arteriosclerosis, gestational diabetes mellitus (GDM) or polycystic ovary syndrome (PCOS), inflammatory disease (such as osteoarthritis, pain or inflammatory enteritis), acne, sunburn, psoriasis, eczema, allergic disease, asthma, peptic ulcer, ulcerative colitis, Crohn's disease, coronary artery disease, arteriosclerosis, atherosclerosis, diabetic retinopathy, diabetic maculopathy, macular edema, diabetic nephropathy, ischemic heart disease, cerebrovascular disorder, peripheral circulatory disturbance, autoimmune disease (such as systemic lupus erythematosus, chronic rheumatism, Sjogren's syndrome, systemic sclerosis, mixed connective tissue disease, Hashimoto's disease, Crohn's disease, ulcerative colitis, idiopathic Addison's disease, male sterility, Goodpasture's syndrome, rapidly progressive glomerulonephritis, myasthenia gravis, polymyositis, multiple sclerosis, autoimmune hemolytic anemia, idiopathic thrombocytopenic purpura, Behcet's disease or CREST syndrome), pancreatitis, cachexia, cancer (such as gastric cancer, lung cancer, breast cancer, colon cancer, prostate cancer, pancreatic cancer or liver cancer), leukemia, sarcoma (such as liposarcoma), osteoporosis, involutional osteoporosis, neurodegenerative disease, Alzheimer's disease, hyperuricemia, dry eyes, or the like.

Also advantageously, the compounds have been found to be highly safe.

Means for Solving the Problems

The present invention relates to:
(1) A compound represented by general formula (I):

[Formula 1]

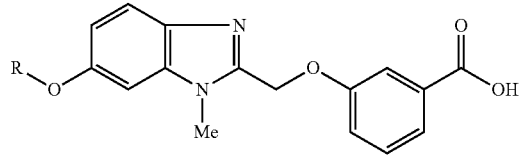

(I)

[wherein
R represents a pyridyl group substituted with 1 to 3 group(s) independently selected from Substituent Group A,
Substituent Group A represents a group consisting of a halogen atom, a $C_1$-$C_6$ alkyl group and a $C_1$-$C_6$ alkoxy group, and Me represents a methyl group]
or a pharmacologically acceptable ester thereof, or a pharmacologically acceptable salt of the compound or ester.

Preferred embodiments of the present invention include:
(2) The compound or pharmacologically acceptable ester thereof, or pharmacologically acceptable salt of the compound or ester according to (1), wherein Substituent Group A is a group consisting of a fluorine atom, a chlorine atom, a methyl group, an ethyl group and a methoxy group;
(3) The compound or pharmacologically acceptable ester thereof, or pharmacologically acceptable salt of the compound or ester according to (1) or (2), wherein R is a 2-pyridyl group substituted with 1 to 3 group(s) independently selected from Substituent Group A;
(4) The compound or pharmacologically acceptable ester thereof, or pharmacologically acceptable salt of the compound or ester according to (1) or (2), wherein R is a 3-pyridyl group substituted with 1 to 3 group(s) independently selected from Substituent Group A;
(5) The compound or pharmacologically acceptable ester thereof, or pharmacologically acceptable salt of the compound or ester according to (1) or (2), wherein R is a 4-pyridyl group substituted with 1 to 3 group(s) independently selected from Substituent Group A;
(6) A compound that is:
3-({6-[(3-chloropyridin-2-yl)oxy]-1-methyl-1H-benzimidazol-2-yl}methoxy)benzoic acid,
3-({6-[(3-ethylpyridin-2-yl)oxy]-1-methyl-1H-benzimidazol-2-yl}methoxy)benzoic acid,
3-({6-[(6-methoxy-5-methylpyridin-2-yl)oxy]-1-methyl-1H-benzimidazol-2-yl}methoxy)benzoic acid,
3-({6-[(5,6-dimethylpyridin-2-yl)oxy]-1-methyl-1H-benzimidazol-2-yl}methoxy)benzoic acid,
3-({6-[(5-chloro-3-fluoropyridin-2-yl)oxy]-1-methyl-1H-benzimidazol-2-yl}methoxy)benzoic acid,
3-({6-[(5-chloro-3-methylpyridin-2-yl)oxy]-1-methyl-1H-benzimidazol-2-yl}methoxy)benzoic acid,
3-({6-[(3,5-dichloropyridin-2-yl)oxy]-1-methyl-1H-benzimidazol-2-yl}methoxy)benzoic acid,
3-({6-[(5-fluoro-3-methylpyridin-2-yl)oxy]-1-methyl-1H-benzimidazol-2-yl}methoxy)benzoic acid,
3-({6-[(3-fluoro-5-methylpyridin-2-yl)oxy]-1-methyl-1H-benzimidazol-2-yl}methoxy)benzoic acid,
3-({6-[(3,5-dimethylpyridin-2-yl)oxy]-1-methyl-1H-benzimidazol-2-yl}methoxy)benzoic acid,
3-({6-[(5-ethyl-3-methylpyridin-2-yl)oxy]-1-methyl-1H-benzimidazol-2-yl}methoxy)benzoic acid,
3-({6-[(3-ethyl-5-methylpyridin-2-yl)oxy]-1-methyl-1H-benzimidazol-2-yl}methoxy)benzoic acid,
3-({6-[(3,6-difluoropyridin-2-yl)oxy]-1-methyl-1H-benzimidazol-2-yl}methoxy)benzoic acid,
3-({6-[(4-methoxy-3,5-dimethylpyridin-2-yl)oxy]-1-methyl-1H-benzimidazol-2-yl}methoxy)benzoic acid,
3-({1-methyl-6-[(3,5,6-trimethylpyridin-2-yl)oxy]-1H-benzimidazol-2-yl}methoxy)benzoic acid,
3-({6-[(2-methoxypyridin-4-yl)oxy]-1-methyl-1H-benzimidazol-2-yl}methoxy)benzoic acid,
3-({6-[(2-methoxy-6-methylpyridin-4-yl)oxy]-1-methyl-1H-benzimidazol-2-yl}methoxy)benzoic acid,
3-({6-[(6-methoxypyridin-3-yl)oxy]-1-methyl-1H-benzimidazol-2-yl}methoxy)benzoic acid or 3-({6-[(5-ethylpyridin-3-yl)oxy]-1-methyl-1H-benzimidazol-2-yl}methoxy)benzoic acid
or a pharmacologically acceptable ester thereof, or a pharmacologically acceptable salt of the compound or ester;
(7) A compound that is:
3-({6-[(3-chloropyridin-2-yl)oxy]-1-methyl-1H-benzimidazol-2-yl}methoxy)benzoic acid,
3-({6-[(3-ethylpyridin-2-yl)oxy]-1-methyl-1H-benzimidazol-2-yl}methoxy)benzoic acid,
3-({6-[(6-methoxy-5-methylpyridin-2-yl)oxy]-1-methyl-1H-benzimidazol-2-yl}methoxy)benzoic acid,
3-({6-[(5,6-dimethylpyridin-2-yl)oxy]-1-methyl-1H-benzimidazol-2-yl}methoxy)benzoic acid,
3-({6-[(5-chloro-3-fluoropyridin-2-yl)oxy]-1-methyl-1H-benzimidazol-2-yl}methoxy)benzoic acid,
3-({6-[(5-chloro-3-methylpyridin-2-yl)oxy]-1-methyl-1H-benzimidazol-2-yl}methoxy)benzoic acid,
3-({6-[(3,5-dichloropyridin-2-yl)oxy]-1-methyl-1H-benzimidazol-2-yl}methoxy)benzoic acid,
3-({6-[(5-fluoro-3-methylpyridin-2-yl)oxy]-1-methyl-1H-benzimidazol-2-yl}methoxy)benzoic acid,
3-({6-[(3-fluoro-5-methylpyridin-2-yl)oxy]-1-methyl-1H-benzimidazol-2-yl}methoxy)benzoic acid,
3-({6-[(3,5-dimethylpyridin-2-yl)oxy]-1-methyl-1H-benzimidazol-2-yl}methoxy)benzoic acid, 3-({6-[(5-ethyl-3-methylpyridin-2-yl)oxy]-1-methyl-1H-benzimidazol-2-yl}methoxy)benzoic acid,
3-({6-[(3-ethyl-5-methylpyridin-2-yl)oxy]-1-methyl-1H-benzimidazol-2-yl}methoxy)benzoic acid,
3-({6-[(3,6-difluoropyridin-2-yl)oxy]-1-methyl-1H-benzimidazol-2-yl}methoxy)benzoic acid,
3-({6-[(4-methoxy-3,5-dimethylpyridin-2-yl)oxy]-1-methyl-1H-benzimidazol-2-yl}methoxy)benzoic acid,
3-({1-methyl-6-[(3,5,6-trimethylpyridin-2-yl)oxy]-1H-benzimidazol-2-yl}methoxy)benzoic acid,
3-({6-[(2-methoxypyridin-4-yl)oxy]-1-methyl-1H-benzimidazol-2-yl}methoxy)benzoic acid,
3-({6-[(2-methoxy-6-methylpyridin-4-yl)oxy]-1-methyl-1H-benzimidazol-2-yl}methoxy)benzoic acid,
3-({6-[(6-methoxypyridin-3-yl)oxy]-1-methyl-1H-benzimidazol-2-yl}methoxy)benzoic acid or
3-({6-[(5-ethylpyridin-3-yl)oxy]-1-methyl-1H-benzimidazol-2-yl}methoxy)benzoic acid
or a pharmacologically acceptable salt thereof;
(8) 3-({6-[(3-Chloropyridin-2-yl)oxy]-1-methyl-1H-benzimidazol-2-yl}methoxy)benzoic acid,
3-({6-[(3-ethylpyridin-2-yl)oxy]-1-methyl-1H-benzimidazol-2-yl}methoxy)benzoic acid,
3-({6-[(6-methoxy-5-methylpyridin-2-yl)oxy]-1-methyl-1H-benzimidazol-2-yl}methoxy)benzoic acid,
3-({6-[(5,6-dimethylpyridin-2-yl)oxy]-1-methyl-1H-benzimidazol-2-yl}methoxy)benzoic acid,
3-({6-[(5-chloro-3-fluoropyridin-2-yl)oxy]-1-methyl-1H-benzimidazol-2-yl}methoxy)benzoic acid,
3-({6-[(5-chloro-3-methylpyridin-2-yl)oxy]-1-methyl-1H-benzimidazol-2-yl}methoxy)benzoic acid,
3-({6-[(3,5-dichloropyridin-2-yl)oxy]-1-methyl-1H-benzimidazol-2-yl}methoxy)benzoic acid,
3-({6-[(5-fluoro-3-methylpyridin-2-yl)oxy]-1-methyl-1H-benzimidazol-2-yl}methoxy)benzoic acid,
3-({6-[(3-fluoro-5-methylpyridin-2-yl)oxy]-1-methyl-1H-benzimidazol-2-yl}methoxy)benzoic acid,
3-({6-[(3,5-dimethylpyridin-2-yl)oxy]-1-methyl-1H-benzimidazol-2-yl}methoxy)benzoic acid,
3-({6-[(5-ethyl-3-methylpyridin-2-yl)oxy]-1-methyl-1H-benzimidazol-2-yl}methoxy)benzoic acid,
3-({6-[(3-ethyl-5-methylpyridin-2-yl)oxy]-1-methyl-1H-benzimidazol-2-yl}methoxy)benzoic acid,
3-({6-[(3,6-difluoropyridin-2-yl)oxy]-1-methyl-1H-benzimidazol-2-yl}methoxy)benzoic acid, 3-({6-[(4-methoxy-3,5-dimethylpyridin-2-yl)oxy]-1-methyl-1H-benzimidazol-2-yl}methoxy)benzoic acid,
3-({1-methyl-6-[(3,5,6-trimethylpyridin-2-yl)oxy]-1H-benzimidazol-2-yl}methoxy)benzoic acid,
3-({6-[(2-methoxypyridin-4-yl)oxy]-1-methyl-1H-benzimidazol-2-yl}methoxy)benzoic acid,
3-({6-[(2-methoxy-6-methylpyridin-4-yl)oxy]-1-methyl-1H-benzimidazol-2-yl}methoxy)benzoic acid,
3-({6-[(6-methoxypyridin-3-yl)oxy]-1-methyl-1H-benzimidazol-2-yl}methoxy)benzoic acid or
3-({6-[(5-ethylpyridin-3-yl)oxy]-1-methyl-1H-benzimidazol-2-yl}methoxy)benzoic acid;
(9) A compound that is:
3-({6-[(3-ethylpyridin-2-yl)oxy]-1-methyl-1H-benzimidazol-2-yl}methoxy)benzoic acid,
3-({6-[(5,6-dimethylpyridin-2-yl)oxy]-1-methyl-1H-benzimidazol-2-yl}methoxy)benzoic acid,
3-({6-[(5-chloro-3-fluoropyridin-2-yl)oxy]-1-methyl-1H-benzimidazol-2-yl}methoxy)benzoic acid,
3-({6-[(5-fluoro-3-methylpyridin-2-yl)oxy]-1-methyl-1H-benzimidazol-2-yl}methoxy)benzoic acid,
3-({6-[(3-fluoro-5-methylpyridin-2-yl)oxy]-1-methyl-1H-benzimidazol-2-yl}methoxy)benzoic acid,
3-({6-[(3,5-dimethylpyridin-2-yl)oxy]-1-methyl-1H-benzimidazol-2-yl}methoxy)benzoic acid,
3-({6-[(5-ethyl-3-methylpyridin-2-yl)oxy]-1-methyl-1H-benzimidazol-2-yl}methoxy)benzoic acid,
3-({6-[(3-ethyl-5-methylpyridin-2-yl)oxy]-1-methyl-1H-benzimidazol-2-yl}methoxy)benzoic acid,
3-({6-[(4-methoxy-3,5-dimethylpyridin-2-yl)oxy]-1-methyl-1H-benzimidazol-2-yl}methoxy)benzoic acid,
3-({1-methyl-6-[(3,5,6-trimethylpyridin-2-yl)oxy]-1H-benzimidazol-2-yl}methoxy)benzoic acid,
3-({6-[(2-methoxypyridin-4-yl)oxy]-1-methyl-1H-benzimidazol-2-yl}methoxy)benzoic acid,
3-({6-[(2-methoxy-6-methylpyridin-4-yl)oxy]-1-methyl-1H-benzimidazol-2-yl}methoxy)benzoic acid or
3-({6-[(6-methoxypyridin-3-yl)oxy]-1-methyl-1H-benzimidazol-2-yl}methoxy)benzoic acid
or a pharmacologically acceptable ester thereof, or a pharmacologically acceptable salt of the compound or ester;
(10) A compound that is:
3-({6-[(3-ethylpyridin-2-yl)oxy]-1-methyl-1H-benzimidazol-2-yl}methoxy)benzoic acid,
3-({6-[(5,6-dimethylpyridin-2-yl)oxy]-1-methyl-1H-benzimidazol-2-yl}methoxy)benzoic acid,
3-({6-[(5-chloro-3-fluoropyridin-2-yl)oxy]-1-methyl-1H-benzimidazol-2-yl}methoxy)benzoic acid,
3-({6-[(5-fluoro-3-methylpyridin-2-yl)oxy]-1-methyl-1H-benzimidazol-2-yl}methoxy)benzoic acid,
3-({6-[(3-fluoro-5-methylpyridin-2-yl)oxy]-1-methyl-1H-benzimidazol-2-yl}methoxy)benzoic acid,
3-({6-[(3,5-dimethylpyridin-2-yl)oxy]-1-methyl-1H-benzimidazol-2-yl}methoxy)benzoic acid,
3-({6-[(5-ethyl-3-methylpyridin-2-yl)oxy]-1-methyl-1H-benzimidazol-2-yl}methoxy)benzoic acid,
3-({6-[(3-ethyl-5-methylpyridin-2-yl)oxy]-1-methyl-1H-benzimidazol-2-yl}methoxy)benzoic acid,
3-({6-[(4-methoxy-3,5-dimethylpyridin-2-yl)oxy]-1-methyl-1H-benzimidazol-2-yl}methoxy)benzoic acid,
3-({1-methyl-6-[(3,5,6-trimethylpyridin-2-yl)oxy]-1H-benzimidazol-2-yl}methoxy)benzoic acid,
3-({6-[(2-methoxypyridin-4-yl)oxy]-1-methyl-1H-benzimidazol-2-yl}methoxy)benzoic acid,
3-({6-[(2-methoxy-6-methylpyridin-4-yl)oxy]-1-methyl-1H-benzimidazol-2-yl}methoxy)benzoic acid or
3-({6-[(6-methoxypyridin-3-yl)oxy]-1-methyl-1H-benzimidazol-2-yl}methoxy)benzoic acid
or a pharmacologically acceptable salt thereof;
(11) A compound that is:
3-({6-[(3-ethylpyridin-2-yl)oxy]-1-methyl-1H-benzimidazol-2-yl}methoxy)benzoic acid,
3-({6-[(5,6-dimethylpyridin-2-yl)oxy]-1-methyl-1H-benzimidazol-2-yl}methoxy)benzoic acid,
3-({6-[(5-chloro-3-fluoropyridin-2-yl)oxy]-1-methyl-1H-benzimidazol-2-yl}methoxy)benzoic acid,
3-({6-[(5-fluoro-3-methylpyridin-2-yl)oxy]-1-methyl-1H-benzimidazol-2-yl}methoxy)benzoic acid,
3-({6-[(3-fluoro-5-methylpyridin-2-yl)oxy]-1-methyl-1H-benzimidazol-2-yl}methoxy)benzoic acid,
3-({6-[(3,5-dimethylpyridin-2-yl)oxy]-1-methyl-1H-benzimidazol-2-yl}methoxy)benzoic acid,
3-({6-[(5-ethyl-3-methylpyridin-2-yl)oxy]-1-methyl-1H-benzimidazol-2-yl}methoxy)benzoic acid,
3-({6-[(3-ethyl-5-methylpyridin-2-yl)oxy]-1-methyl-1H-benzimidazol-2-yl}methoxy)benzoic acid,
3-({6-[(4-methoxy-3,5-dimethylpyridin-2-yl)oxy]-1-methyl-1H-benzimidazol-2-yl}methoxy)benzoic acid, 3-({1-methyl-6-[(3,5,6-trimethylpyridin-2-yl)oxy]-1H-benzimidazol-2-yl}methoxy)benzoic acid,
3-({6-[(2-methoxypyridin-4-yl)oxy]-1-methyl-1H-benzimidazol-2-yl}methoxy)benzoic acid,
3-({6-[(2-methoxy-6-methylpyridin-4-yl)oxy]-1-methyl-1H-benzimidazol-2-yl}methoxy)benzoic acid or
3-({6-[(6-methoxypyridin-3-yl)oxy]-1-methyl-1H-benzimidazol-2-yl}methoxy)benzoic acid;

(12) 3-({6-[(3-Ethylpyridin-2-yl)oxy]-1-methyl-1H-benzimidazol-2-yl}methoxy)benzoic acid;
(13) 3-({6-[(5,6-Dimethylpyridin-2-yl)oxy]-1-methyl-1H-benzimidazol-2-yl}methoxy)benzoic acid;
(14) 3-({6-[(5-Chloro-3-fluoropyridin-2-yl)oxy]-1-methyl-1H-benzimidazol-2-yl}methoxy)benzoic acid;
(15) 3-({6-[(5-Chloro-3-methylpyridin-2-yl)oxy]-1-methyl-1H-benzimidazol-2-yl}methoxy)benzoic acid;
(16) 3-({6-[(5-Fluoro-3-methylpyridin-2-yl)oxy]-1-methyl-1H-benzimidazol-2-yl}methoxy)benzoic acid;
(17) 3-({6-[(3-Fluoro-5-methylpyridin-2-yl)oxy]-1-methyl-1H-benzimidazol-2-yl}methoxy)benzoic acid;
(18) 3-({6-[(3,5-Dimethylpyridin-2-yl)oxy]-1-methyl-1H-benzimidazol-2-yl}methoxy)benzoic acid;
(19) 3-({6-[(5-Ethyl-3-methylpyridin-2-yl)oxy]-1-methyl-1H-benzimidazol-2-yl}methoxy)benzoic acid;
(20) 3-({6-[(3-Ethyl-5-methylpyridin-2-yl)oxy]-1-methyl-1H-benzimidazol-2-yl}methoxy)benzoic acid;
(21) 3-({6-[(3,6-Difluoropyridin-2-yl)oxy]-1-methyl-1H-benzimidazol-2-yl}methoxy)benzoic acid;
(22) 3-({6-[(4-Methoxy-3,5-dimethylpyridin-2-yl)oxy]-1-methyl-1H-benzimidazol-2-yl}methoxy)benzoic acid;
(23) 3-({1-Methyl-6-[(3,5,6-trimethylpyridin-2-yl)oxy]-1H-benzimidazol-2-yl}methoxy)benzoic acid;
(24) 3-({6-[(2-methoxypyridin-4-yl)oxy]-1-methyl-1H-benzimidazol-2-yl}methoxy)benzoic acid;
(25) 3-({6-[(2-Methoxy-6-methylpyridin-4-yl)oxy]-1-methyl-1H-benzimidazol-2-yl}methoxy)benzoic acid;
(26) 3-({6-[(6-Methoxypyridin-3-yl)oxy]-1-methyl-1H-benzimidazol-2-yl}methoxy)benzoic acid;
(27) A pharmaceutical composition comprising the compound or pharmacologically acceptable ester thereof, or pharmacologically acceptable salt of the compound or ester according to any one of (1) to (26) as an active ingredient;
(28) The pharmaceutical composition according to (27), wherein the pharmaceutical composition is a composition for lowering blood glucose;
(29) The pharmaceutical composition according to (27), wherein the pharmaceutical composition is a composition for the treatment and/or prevention of diabetes;
(30) The pharmaceutical composition according to (27), wherein the pharmaceutical composition is a composition for the treatment and/or prevention of type II diabetes;
(31) The pharmaceutical composition according to (27), wherein the pharmaceutical composition is a composition for activating peroxisome proliferator-activated receptor (PPAR) γ;
(32) The pharmaceutical composition according to (27), wherein the pharmaceutical composition is a composition for improving carbohydrate or lipid metabolism, for improving insulin resistance, for inhibiting inflammation or for inhibiting the growth of cancer cells;
(33) The pharmaceutical composition according to (27), wherein the pharmaceutical composition is a composition for the treatment and/or prevention of a disease caused by metabolic syndrome;
(34) The pharmaceutical composition according to (27), wherein the pharmaceutical composition is a composition for the treatment and/or prevention of a disease mediated by peroxisome proliferator-activated receptor (PPAR) γ;
(35) The pharmaceutical composition according to (27), wherein the pharmaceutical composition activates peroxisome proliferator-activated receptor (PPAR) γ and improves insulin resistance to treat, improve, relieve and/or prevent symptoms;
(36) The pharmaceutical composition according to (27), wherein the pharmaceutical composition is a composition for the treatment and/or prevention of hyperglycemia, hyperlipidemia, adiposity, impaired glucose tolerance, insulin resistance, impaired fasting glucose, hypertension, fatty liver, nonalcoholic steatohepatitis, diabetic complications, arteriosclerosis, atherosclerosis, gestational diabetes mellitus or polycystic ovary syndrome;
(37) The pharmaceutical composition according to (27), wherein the pharmaceutical composition is a composition for the treatment and/or prevention of inflammatory disease, cancer, osteoporosis, involutional osteoporosis, neurodegenerative disease, Alzheimer's disease or hyperuricemia;
(38) The pharmaceutical composition according to (27), wherein the pharmaceutical composition is a composition for the treatment and/or prevention of acne, sunburn, psoriasis, eczema, allergic disease, asthma, peptic ulcer, ulcerative colitis, Crohn's disease, coronary artery disease, arteriosclerosis, atherosclerosis, diabetic retinopathy, diabetic maculopathy, macular edema, diabetic nephropathy, ischemic heart disease, cerebrovascular disorder, peripheral circulatory disturbance, autoimmune disease, pancreatitis, cachexia, leukemia, sarcoma or dry eyes;
(39) A peroxisome proliferator-activated receptor (PPAR) γ activator/modulator comprising the compound or pharmacologically acceptable ester thereof, or pharmacologically acceptable salt of the compound or ester according to any one of (1) to (26) as an active ingredient;
(40) Use of the compound or pharmacologically acceptable ester thereof, or pharmaceutically acceptable salt of the compound or ester according to any one of (1) to (26) for producing a pharmaceutical composition;
(41) The use according to (40), wherein the pharmaceutical composition is a composition for lowering blood glucose;
(42) The use according to (40), wherein the pharmaceutical composition is a composition for the treatment and/or prevention of diabetes;
(43) The use according to (40), wherein the pharmaceutical composition is a composition for the treatment and/or prevention of type II diabetes;
(44) The use according to (40), wherein the pharmaceutical composition is a composition for activating peroxisome proliferator-activated receptor (PPAR) γ;
(45) The use according to (40), wherein the pharmaceutical composition is a composition for improving carbohydrate or lipid metabolism, for improving insulin resistance, for inhibiting inflammation or for inhibiting the growth of cancer cells;
(46) The use according to (40), wherein the pharmaceutical composition is a composition for the treatment and/or prevention of a disease caused by metabolic syndrome;
(47) The use according to (40), wherein the pharmaceutical composition is a composition for the treatment and/or prevention of hyperglycemia, hyperlipidemia, adiposity, impaired glucose tolerance, insulin resistance, impaired fasting glucose, hypertension, fatty liver, nonalcoholic steatohepatitis, diabetic complications, arteriosclerosis, atherosclerosis, gestational diabetes mellitus or polycystic ovary syndrome;

(48) The use according to (40), wherein the pharmaceutical composition is a composition for the treatment and/or prevention of inflammatory disease, cancer, osteoporosis, involutional osteoporosis, neurodegenerative disease, Alzheimer's disease or hyperuricemia;

(49) The use according to (40), wherein the pharmaceutical composition is a composition for the treatment and/or prevention of acne, sunburn, psoriasis, eczema, allergic disease, asthma, peptic ulcer, ulcerative colitis, Crohn's disease, coronary artery disease, arteriosclerosis, atherosclerosis, diabetic retinopathy, diabetic maculopathy, macular edema, diabetic nephropathy, ischemic heart disease, cerebrovascular disorder, peripheral circulatory disturbance, autoimmune disease, pancreatitis, cachexia, leukemia, sarcoma or dry eyes;

(50) The use according to (40), wherein the pharmaceutical composition is a peroxisome proliferator-activated receptor (PPAR) γ activator/modulator;

(51) A method for lowering blood glucose, comprising administering a pharmacologically effective amount of the compound or pharmacologically acceptable ester thereof, or pharmacologically acceptable salt of the compound or ester according to any one of (1) to (26) to a warm-blooded animal;

(52) A method for activating peroxisome proliferator-activated receptor (PPAR) γ, comprising administering a pharmacologically effective amount of the compound or pharmacologically acceptable ester thereof, or pharmacologically acceptable salt of the compound or ester according to any one of (1) to (26) to a warm-blooded animal;

(53) A method for improving carbohydrate or lipid metabolism, for improving insulin resistance, for inhibiting inflammation or for inhibiting the growth of cancer cells, comprising administering a pharmacologically effective amount of the compound or pharmacologically acceptable ester thereof, or pharmacologically acceptable salt of the compound or ester according to any one of (1) to (26) to a warm-blooded animal;

(54) A method for the treatment and/or prevention of a disease, comprising administering a pharmacologically effective amount of the compound or pharmacologically acceptable ester thereof, or pharmacologically acceptable salt of the compound or ester according to any one of (1) to (26) to a warm-blooded animal;

(55) The method according to (54), wherein the disease is diabetes;

(56) The method according to (54), wherein the disease is type II diabetes;

(57) The method according to (54), wherein the disease is a disease caused by metabolic syndrome;

(58) The method according to (54), wherein the disease is hyperglycemia, hyperlipidemia, adiposity, impaired glucose tolerance, insulin resistance, impaired fasting glucose, hypertension, fatty liver, nonalcoholic steatohepatitis, diabetic complications, arteriosclerosis, atherosclerosis, gestational diabetes mellitus or polycystic ovary syndrome;

(59) The method according to (54), wherein the disease is inflammatory disease, cancer, osteoporosis, involutional osteoporosis, neurodegenerative disease, Alzheimer's disease or hyperuricemia;

(60) The method according to (54), wherein the disease is acne, sunburn, psoriasis, eczema, allergic disease, asthma, peptic ulcer, ulcerative colitis, Crohn's disease, coronary artery disease, arteriosclerosis, atherosclerosis, diabetic retinopathy, diabetic maculopathy, macular edema, diabetic nephropathy, ischemic heart disease, cerebrovascular disorder, peripheral circulatory disturbance, autoimmune disease, pancreatitis, cachexia, leukemia, sarcoma or dry eyes; and

(61) The method according to any one of (51) to (60), wherein the warm-blooded animal is a human.

The "halogen atom" in the present invention is a fluorine atom, a chlorine atom, a bromine atom or an iodine atom. The halogen atom is preferably a fluorine atom or a chlorine atom.

The "$C_1$-$C_6$ alkyl group" in the present invention is a linear or branched alkyl group having 1 to 6 carbon atom(s). Examples of such a group include a methyl group, an ethyl group, a propyl group, an isopropyl group, a butyl group, an isobutyl group, an s-butyl group, a t-butyl group, a pentyl group, an isopentyl group and a hexyl group. The group is preferably a methyl group or an ethyl group.

The "$C_1$-$C_6$ alkoxy group" in the present invention is a group in which the above-mentioned "$C_1$-$C_6$ alkyl group" is bonded to an oxygen atom, and is a linear or branched alkoxy group having 1 to 6 carbon atom(s). Examples of such a group include a methoxy group, an ethoxy group, a propoxy group, an isopropoxy group, a butoxy group, an isobutoxy group, an s-butoxy group, a t-butoxy group, a pentyloxy group, an isopentyloxy group and a hexyloxy group. The group is preferably a methoxy group or an ethoxy group, and more preferably a methoxy group.

The "Substituent Group A" in the present invention is a group consisting of the above-mentioned "halogen atom", the above-mentioned "$C_1$-$C_6$ alkyl group" and the above-mentioned "$C_1$-$C_6$ alkoxy group", and is preferably a group consisting of a fluorine atom, a chlorine atom, a methyl group, an ethyl group and a methoxy group.

The "pyridyl group substituted with 1 to 3 group(s) independently selected from Substituent Group A" in the present invention is a 2-pyridyl group, 3-pyridyl group or 4-pyridyl group substituted with 1 to 3 group(s) independently selected from the above-mentioned "Substituent Group A", and is preferably a 2-pyridyl group, 3-pyridyl group or 4-pyridyl group substituted with 1 to 3 group(s) independently selected from the group consisting of a fluorine atom, a chlorine atom, a methyl group, an ethyl group and a methoxy group.

In the present invention, R is preferably a 2-pyridyl group, 3-pyridyl group, or 4-pyridyl group substituted with 1 to 3 group(s) independently selected from the group consisting of a fluorine atom, a chlorine atom, a methyl group, an ethyl group and a methoxy group.

The compound represented by the general formula (I) or pharmacologically acceptable ester thereof, or pharmacologically acceptable salt of the compound or ester according to the present invention includes all isomers (such as a keto-enol isomer, a diastereomer, an optical isomer, a rotamer, etc.).

The compound represented by the general formula (I) or pharmacologically acceptable ester thereof, or pharmacologically acceptable salt of the compound or ester according to the present invention has various isomers because asymmetric carbon atom(s) exist in the molecule. These isomers and mixtures of these isomers of the present invention are all represented by a single formula, specifically, the general formula (I). Accordingly, the present invention includes all of these isomers and mixtures of these isomers in arbitrary ratios.

The aforementioned stereoisomers can be obtained by synthesizing the compound of the present invention using an optically active raw material compound or using an asymmetric synthesis or asymmetric induction technique or by isolating the synthesized compound of the present invention by a common optical resolution or separation method if desired.

The compound represented by the general formula (I) or pharmacologically acceptable ester thereof, or pharmacologically acceptable salt of the compound or ester according to the present invention may contain unnatural proportions of atomic isotopes at one or more of the atoms that constitute such compounds. Examples of atomic isotopes include deuterium ($^2$H), tritium ($^3$H), iodine-125 ($^{125}$I) and carbon-14 ($^{14}$C). The above-described compounds may be radiolabeled with radioisotopes such as tritium ($^3$H), iodine-125 ($^{125}$I) or carbon-14 ($^{14}$C). Radiolabeled compounds are useful as therapeutic or prophylactic agents, research reagents such as assay reagents, and diagnostic agents such as in vivo diagnostic imaging agents. All isotopic variants of the compounds of the present invention, whether radioactive or not, are included in the scope of the present invention.

The "pharmacologically acceptable ester thereof" refers to an ester of the compound represented by the general formula (I), which has a carboxyl group and can therefore be esterified, wherein the ester has an ester residue that is a "protecting group that can be cleaved in vivo by a biological method such as hydrolysis".

The "protecting group that can be cleaved in vivo by a biological method such as hydrolysis" refers to a protecting group to be cleaved in the human body by a biological method such as hydrolysis to generate a free acid or a salt thereof. Whether the ester has such a protecting group or not can be determined by administering the ester to laboratory animals such as rats or mice and then examining the body fluid of the animals to confirm if the original compound or pharmacologically acceptable salt thereof can be detected. Examples of the protecting group include ($C_1$-$C_6$ alkoxy)-($C_1$-$C_6$ alkyl) groups such as 1-methoxyethyl, 1-ethoxyethyl, 1-methyl-1-methoxyethyl, 1-(isopropoxy)ethyl, 2-methoxyethyl, 2-ethoxyethyl, 1,1-dimethyl-1-methoxyethyl, ethoxymethyl, n-propoxymethyl, isopropoxymethyl, n-butoxymethyl and t-butoxymethyl; ($C_1$-$C_6$ alkoxy)-($C_1$-$C_6$ alkoxy)-($C_1$-$C_6$ alkyl) groups such as 2-methoxyethoxymethyl; $C_6$-$C_{14}$ aryl groups such as phenyl and naphthyl; ($C_6$-$C_{14}$ aryloxy)-($C_1$-$C_6$ alkyl) groups such as phenoxymethyl; ($C_1$-$C_6$ halogenated alkoxy)-($C_1$-$C_6$ alkyl) groups such as 2,2,2-trichloroethoxymethyl (the "$C_1$-$C_6$ halogenated alkoxy" is a group in which 1 to 5 of the above-mentioned "halogen atom(s)", which may be the same or different, are bonded to the above-mentioned "$C_1$-$C_6$ alkoxy group"); bis($C_1$-$C_6$ halogenated alkoxy)-($C_1$-$C_6$ alkyl) groups such as bis(2-chloroethoxy)methyl; ($C_1$-$C_6$ alkoxy)carbonyl($C_1$-$C_6$ alkyl)groups such as methoxycarbonylmethyl; cyano($C_1$-$C_6$ alkyl)groups such as cyanomethyl and 2-cyanoethyl; ($C_1$-$C_6$ alkyl)thiomethyl groups such as methylthiomethyl and ethylthiomethyl; ($C_6$-$C_{14}$ aryl)thiomethyl groups such as phenylthiomethyl and naphthylthiomethyl; ($C_1$-$C_6$ alkylsulfonyl)-($C_1$-$C_6$ alkyl) groups such as 2-methanesulfonylethyl; ($C_1$-$C_6$ halogenated alkylsulfonyl)-($C_1$-$C_6$ alkyl) groups such as 2-trifluoromethanesulfonylethyl; ($C_6$-$C_{14}$ aryl)sulfonyl($C_1$-$C_6$ alkyl) groups such as 2-benzenesulfonylethyl and 2-toluenesulfonylethyl; 1-(acyloxy)-($C_1$-$C_6$ alkyl) groups such as 1-(acyloxy)methyl and 1-(acyloxy)ethyl; phthalidyl groups such as phthalidyl, dimethylphthalidyl and dimethoxyphthalidyl; $C_1$-$C_6$ alkyl groups such as methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl and 2-ethylbutyl; and carboxy($C_1$-$C_6$ alkyl) groups such as carboxymethyl.

Methods of selecting and producing the "protecting group that can be cleaved in vivo by a biological method such as hydrolysis" are described in Design of Prodrugs, Elsevier, Amsterdam 1985 and Iyakuhin No Kaihatsu [Development of Pharmaceuticals], Vol. 7, Bunshi Sekkei [Molecular Design], Hirokawa Shoten, published in 1990, for example.

The "pharmacologically acceptable salt of the compound or ester" refers to a salt that does not have significant toxicity and can be used as a medicine. The compound represented by the general formula (I) or pharmacologically acceptable ester thereof can be converted to a salt by reacting a basic group with an acid or by reacting an acidic group with a base.

Examples of the salt based on a basic group include hydrohalides such as hydrofluorides, hydrochlorides, hydrobromides and hydroiodides; inorganic acid salts such as nitrates, perchlorates, sulfates and phosphates; alkyl sulfonates such as methanesulfonates and ethanesulfonates; haloalkyl sulfonates such as trifluoromethanesulfonates; aryl sulfonates such as benzenesulfonates and p-toluenesulfonates; and organic acid salts such as acetates, malates, fumarates, succinates, citrates, ascorbates, tartrates, oxalates and maleates.

On the other hand, examples of the salt based on an acidic group include alkali metal salts such as sodium salts, potassium salts and lithium salts; alkaline earth metal salts such as calcium salts and magnesium salts; and metal salts such as aluminum salts and iron salts.

The compound represented by the general formula (I) or pharmacologically acceptable ester thereof, or pharmacologically acceptable salt of the compound or ester according to the present invention may incorporate water molecules to form a hydrate when left to stand in the air or recrystallized, and such a hydrate is also included in the salt of the present invention.

The compound represented by the general formula (I) or pharmacologically acceptable ester thereof, or pharmacologically acceptable salt of the compound or ester according to the present invention may absorb some other specific solvent(s) to form a solvate, and such a solvate is also included in the salt of the present invention.

The compound represented by the general formula (I) or pharmacologically acceptable ester thereof, or pharmacologically acceptable salt of the compound or ester according to the present invention is preferably the compound represented by the general formula (I) or pharmacologically acceptable salt thereof according to the present invention, and more preferably the compound represented by the general formula (I) according to the present invention.

Advantageous Effects of Invention

The compounds represented by the general formula (I) or pharmacologically acceptable esters thereof, or pharmacologically acceptable salts of the compounds or esters according to the present invention have been found to have an excellent hypoglycemic effect, an effect of improving carbohydrate or lipid metabolism, an effect of improving insulin resistance or an effect of improving so-called metabolic syndrome such as arteriosclerosis, hypertension, cardiovascular disorder or complications derived from them or a pathology caused by various inflammations. It has also been found that the compounds are ligands acting on peroxisome proliferator-activated receptor (PPAR) γ and therefore have an effect of inhibiting the growth of cancer cells. The compounds are useful in a therapeutic agent or prophylactic agent for metabolic syndrome, specifically, a disease such as diabetes, hyperglycemia, hyperlipidemia, adiposity, impaired glucose tolerance (IGT), insulin resistance, impaired fasting glucose (IFG), hypertension, fatty liver, nonalcoholic steatohepatitis (NASH), diabetic complications (such as retinopathy, nephropathy or neuropathy), arteriosclerosis, gestational diabetes mellitus (GDM) or polycystic ovary syndrome (PCOS), inflammatory disease (such as osteoarthritis, pain or inflammatory enteritis), acne, sunburn, psoriasis, eczema, allergic disease, asthma, peptic ulcer, ulcerative colitis, Crohn's disease, coronary artery disease, arteriosclerosis, atherosclerosis, diabetic retinopathy, diabetic maculopathy, macular edema, diabetic nephropathy, ischemic heart disease, cerebrovascular disorder, peripheral circulatory disturbance, autoimmune disease (such as systemic lupus erythematosus, chronic rheumatism, Sjogren's syndrome, systemic sclerosis, mixed connective tissue disease, Hashimoto's disease, Crohn's disease, ulcerative colitis, idiopathic Addison's disease, male sterility, Goodpasture's syndrome, rapidly progressive glomerulonephritis, myasthenia gravis, polymyositis, multiple sclerosis, autoimmune hemolytic anemia, idiopathic thrombocytopenic purpura, Behcet's disease or CREST syndrome), pancreatitis, cachexia, cancer (such as gastric cancer, lung cancer, breast cancer, colon cancer, prostate cancer, pancreatic cancer or liver cancer), leukemia, sarcoma (such as liposarcoma), osteoporosis, involutional osteoporosis, neurodegenerative disease, Alzheimer's disease, hyperuricemia or dry eyes. They can also be used as a drug for the treatment and/or prevention of the aforementioned diseases.

Also advantageously, the compounds represented by the general formula (I) or pharmacologically acceptable esters thereof, or pharmacologically acceptable salts of the compounds or esters according to the present invention are highly safe.

DETAILED DESCRIPTION

The compound represented by the general formula (I) according to the present invention can be produced according to Processes A to D described below.

The solvent used in the reaction in each step of the following Processes A to D is not particularly limited insofar as it does not inhibit the reaction and dissolves the starting material to some extent. The solvent is selected from the following solvent group, for example. The solvent group consists of hydrocarbons such as pentane, hexane, octane, petroleum ether, ligroin and cyclohexane; amides such as formamide, N,N-dimethylformamide, N,N-dimethylacetamide, N-methyl-2-pyrrolidone, N-methyl-2-pyrrolidinone and hexamethylphosphoric triamide; ethers such as diethyl ether, diisopropyl ether, tetrahydrofuran, dioxane, dimethoxyethane, diethylene glycol dimethyl ether and cyclopentyl methyl ether; alcohols such as methanol, ethanol, n-propanol, i-propanol, n-butanol, 2-butanol, 2-methyl-1-propanol, t-butanol, isoamyl alcohol, diethylene glycol, glycerin, octanol, cyclohexanol and methyl cellosolve; sulfoxides such as dimethyl sulfoxide; sulfones such as sulfolane; nitriles such as acetonitrile, propionitrile, butyronitrile and isobutyronitrile; esters such as ethyl formate, ethyl acetate, propyl acetate, butyl acetate and diethyl carbonate; ketones such as acetone, methyl ethyl ketone, 4-methyl-2-pentanone, methyl isobutyl ketone, isophorone and cyclohexanone; nitro compounds such as nitroethane and nitrobenzene; halogenated hydrocarbons such as dichloromethane, 1,2-dichloroethane, chlorobenzene, dichlorobenzene, chloroform and carbon tetrachloride; aromatic hydrocarbons such as benzene, toluene and xylene; carboxylic acids such as acetic acid, formic acid, propionic acid, butyric acid and trifluoroacetic acid; water; and mixed solvents thereof.

Examples of the base used in the reaction in each step of the following Processes A to D include inorganic bases such as alkali metal carbonates such as sodium carbonate, potassium carbonate, lithium carbonate and cesium carbonate; alkali metal bicarbonates such as sodium bicarbonate, potassium bicarbonate and lithium bicarbonate; alkali metal hydrides such as lithium hydride, sodium hydride and potassium hydride; alkali metal hydroxides such as sodium hydroxide, potassium hydroxide, and lithium hydroxide; and alkali metal fluorides such as sodium fluoride and potassium fluoride; alkali metal alkoxides such as sodium methoxide, sodium ethoxide, sodium t-butoxide, potassium methoxide, potassium ethoxide, potassium t-butoxide and lithium methoxide; alkali metal trialkylsilanolates such as sodium trimethylsilanolate, potassium trimethylsilanolate and lithium trimethylsilanolate; alkali metal mercaptans such as sodium methyl mercaptan and sodium ethyl mercaptan; organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU); and organometallic bases such as butyllithium, lithium diisopropylamide and lithium bis(trimethylsilyl)amide.

In the reaction in each step of the following Processes A to D, the reaction temperature varies according to the solvent, the starting material, the reagent and the like, and the reaction time varies according to the solvent, the starting material, the reagent, the reaction temperature and the like.

In the reaction in each step of the following Processes A to D, each desired compound is collected from the reaction mixture according to conventional methods after completion of the reaction. The desired compound is obtained as follows, for example. The reaction mixture is appropriately neutralized and insoluble matter, if present, is removed by filtration. Then, water and an immiscible organic solvent such as ethyl acetate are added, and the organic layer containing the desired compound is separated. The organic layer is washed with water or the like and then dried over anhydrous magnesium sulfate, anhydrous sodium sulfate or the like and filtered. Then, the solvent is evaporated. The resulting desired compound may be isolated and purified if necessary by appropriately combining usual methods, for example, methods suitably used for isolation and purification of organic compounds such as recrystallization and reprecipitation and eluting with an appropriate eluent by application of chromatography. The desired compound insoluble in a solvent may be purified by washing the resulting solid crude product with a solvent. The desired compound in each step may also be used as is for the next reaction without purification.

In the reaction in each step of the following Processes A to D, R and Me are as defined above, X represents a halogen atom (preferably a chlorine atom in the compound represented by the general formula (II) and the compound represented by the general formula (XI), and preferably a fluorine atom or a bromine atom in the compound represented by the general formula (XX)), Y represents a protecting group for the carboxyl group (a protecting group generally used in organic synthesis chemistry, preferably a $C_1$-$C_6$ alkyl group, and more preferably a methyl group or an ethyl group) and Z represents a $C_1$-$C_6$ alkoxy group (preferably a methoxy group).

The "protecting group for the carboxyl group" as defined above for Y refers to a protecting group that can be cleaved by a chemical method such as hydrogenolysis, hydrolysis, electrolysis or photolysis and represents a protecting group generally used in organic synthesis chemistry (see T. W. Greene et al., Protective Groups in Organic Synthesis, 3rd Edition, John Wiley & Sons, Inc. (1999), for example). Such a protecting group is not particularly limited insofar as it is a protecting group for a carboxyl group used in the field of organic synthesis chemistry. Examples of the protecting group include $C_1$-$C_6$ alkyl groups; $C_2$-$C_6$ alkenyl groups such as ethenyl, 1-propenyl and 2-propenyl; $C_2$-$C_6$ alkynyl groups such as ethynyl, 1-propynyl and 2-propynyl; $C_1$-$C_6$ halogenated alkyl groups such as trifluoromethyl and trichloromethyl; $C_1$-$C_6$ hydroxyalkyl groups such as hydroxymethyl and 2-hydroxyethyl; ($C_2$-$C_7$ alkylcarbonyl)-($C_1$-$C_6$ alkyl)groups such as acetylmethyl; aralkyl groups such as benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl; and silyl groups such as trimethylsilyl, triethylsilyl, isopropyldimethylsilyl, t-butyldimethylsilyl, methyldiisopropylsilyl, methyldi-t-butylsilyl, triisopropylsilyl, diphenylmethylsilyl, diphenylbutylsilyl, diphenylisopropylsilyl and phenyldiisopropylsilyl. Preferred examples include $C_1$-$C_6$ alkyl groups and aralkyl groups, more preferred examples include $C_1$-$C_6$ alkyl groups, and particularly preferred examples include a methyl group and an ethyl group.

The steps involving protection and deprotection are carried out according to known methods (such as a method described in "Protective Groups in Organic Synthesis" (Theodora W. Greene, Peter G. M. Wuts, 1999, published by Wiley-Interscience Publication)).

The reaction in each step of Processes A to D will be described below.

Process A is a process for producing a compound represented by the general formula (I).

Process A

[Formula 2]

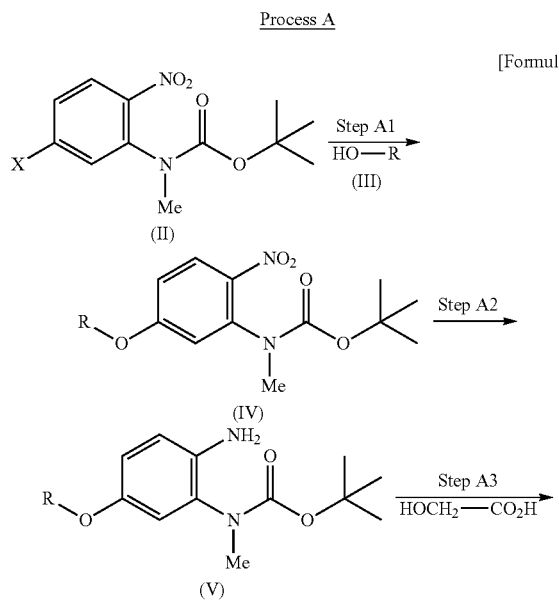

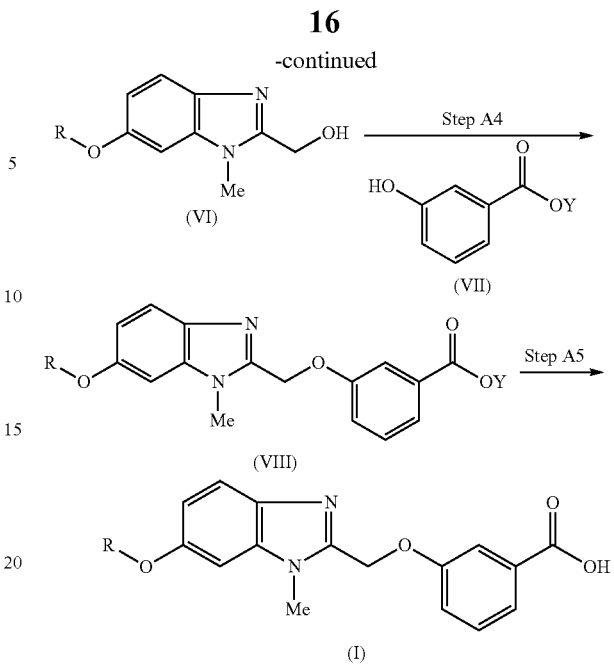

Step A1

This step is a step of producing a compound represented by the general formula (IV).

This step is carried out by reacting a compound represented by the general formula (II) with a compound represented by the general formula (III) in a solvent in the presence of a base.

The compound represented by the general formula (II) and the compound represented by the general formula (III) used in this step are known compounds or are easily produced from known compounds as starting materials by a known method or a method similar to a known method.

The solvent used in this step is preferably an amide, and more preferably N,N-dimethylformamide or N-methyl-2-pyrrolidone.

The base used in this step is preferably an alkali metal carbonate or an alkali metal hydride, and more preferably cesium carbonate or sodium hydride.

The reaction temperature in this step is usually 50° C. to 150° C., and preferably 80° C. to 120° C.

The reaction time in this step is usually 0.5 to 48 hours, and preferably 1 to 30 hours.

Step A2

This step is a step of producing a compound represented by the general formula (V).

This step is carried out by reacting the compound represented by the general formula (IV) with iron in a solvent in the presence of a weak acid or by reducing the compound represented by the general formula (IV) in a solvent in the presence of a palladium catalyst in a hydrogen atmosphere.

The solvent used in this step is preferably an ether, an alcohol, water or a mixed solvent of an alcohol and water, more preferably tetrahydrofuran, methanol, ethanol, water or a mixed solvent of ethanol and water, and still more preferably ethanol or a mixed solvent of ethanol and water.

The weak acid used in this step is preferably acetic acid or ammonium chloride, and more preferably ammonium chloride.

The palladium catalyst used in this step is, for example, a divalent palladium catalyst or a zerovalent palladium catalyst, preferably palladium-active carbon, palladium (II) acetate, palladium (II) trifluoroacetate, palladium black, palladium (II) bromide, palladium (II) chloride, palladium (II) iodide, palladium (II) cyanide, palladium (II) nitrate, palladium (II) oxide, palladium (II) sulfate, dichlorobis(acetonitrile)palladium (II), dichlorobis(benzonitrile)palladium (II), dichloro(1,5-cyclooctadiene)palladium (II), acetylacetone palladium (II), palladium (II) sulfide, tris(dibenzylideneacetone)dipalladium (0), tetrakis(acetonitrile)palladium (II) tetrafluoroborate or an aryl chloride-palladium dimer, more preferably palladium-active carbon or palladium (II) acetate, and still more preferably palladium-active carbon.

The reaction temperature in this step is usually −20° C. to 120° C., and preferably 0° C. to 100° C.

The reaction time in this step is usually 1 to 48 hours, and preferably 2 to 24 hours.

Step A3

This step is a step of producing a compound represented by the general formula (VI).

This step is carried out by reacting the compound represented by the general formula (V) with glycolic acid in a solvent in the presence of hydrochloric acid (preferably 4 N hydrochloric acid).

The solvent used in this step is preferably an ether, water or a mixed solvent of an ether and water, more preferably dioxane, water or a mixed solvent of dioxane and water, and still more preferably a mixed solvent of dioxane and water.

The reaction temperature in this step is usually 50° C. to 150° C., and preferably 80° C. to 120° C.

The reaction time in this step is usually 0.5 to 48 hours, and preferably 1 to 24 hours.

Step A4

This step is a step of producing a compound represented by the general formula (VIII).

This step is carried out by reacting the compound represented by the general formula (VI) with a compound represented by the general formula (VII) in a solvent in the presence of a condensing agent.

The compound represented by the general formula (VII) used in this step is a known compound or is easily produced from a known compound as a starting material by a known method or a method similar to a known method.

The solvent used in this step is preferably an aromatic hydrocarbon, and more preferably toluene.

Examples of the condensing agent used in this step include a combination of an azodicarboxylate and a tertiary phosphine, a combination of an azodicarboxylic amide and a tertiary phosphine, and (trialkylphosphoranylidene)acetonitrile. The condensing agent is preferably a combination of an azodicarboxylic amide and a tertiary phosphine, and more preferably a combination of tributylphosphine and 1,1'-(azodicarbonyl)dipiperidine.

The reaction temperature in this step is usually −78° C. to 120° C., and preferably 0° C. to 50° C.

The reaction time in this step is usually 0.5 to 24 hours, and preferably 1 to 12 hours.

Step A5

This step is a step of producing a compound represented by the general formula (I).

This step is carried out according to known methods (such as a method described in "Protective Groups in Organic Synthesis" (Theodora W. Greene, Peter G. M. Wuts, 1999, published by Wiley-Interscience Publication)). An example where Y is a $C_1$-$C_6$ alkyl group will be demonstrated below.

This step is carried out by reacting the compound represented by the general formula (VIII) with a base in a solvent.

The solvent used in this step is preferably an ether or an alcohol, and more preferably tetrahydrofuran, dioxane or methanol.

The base used in this step is preferably an alkali metal hydroxide, more preferably lithium hydroxide, potassium hydroxide or sodium hydroxide, and still more preferably sodium hydroxide.

The reaction temperature in this step is usually 0° C. to 150° C., and preferably 20° C. to 100° C.

The reaction time in this reaction is usually 0.5 to 24 hours, and preferably 1 to 10 hours.

Process B is another process for producing a compound represented by the general formula (I).

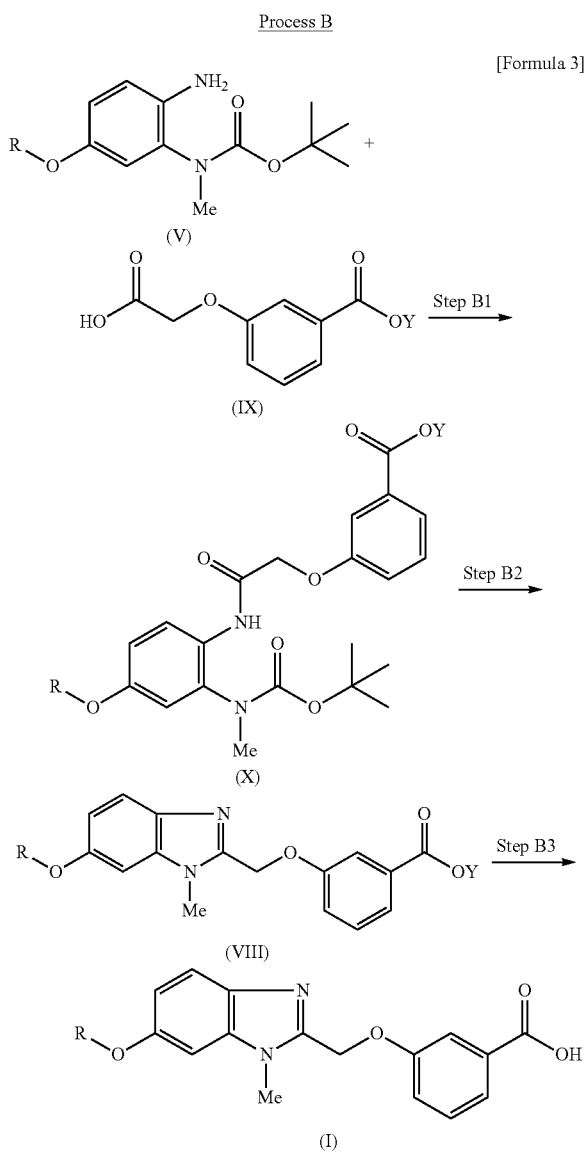

Step B1

This step is a step of producing a compound represented by the general formula (X).

This step is carried out by reacting a compound represented by the general formula (V) with a compound represented by the general formula (IX) in a solvent in the presence of a condensing agent and a base.

The compound represented by the general formula (IX) used in this step is a known compound or is easily produced from a known compound as a starting material by a known method or a method similar to a known method.

The solvent used in this step is preferably an ether, an amide or a halogenated hydrocarbon, and more preferably tetrahydrofuran, N,N-dimethylformamide or dichloromethane.

Examples of the condensing agent used in this step include O-(7-azabenzotriazol-1-yl)-N,N,N',N'-tetramethyluronium hexafluorophosphate (HATU), 1-propanephosphonic acid cyclic anhydride (T3P), dicyclohexylcarbodiimide (DCCD), 1-ethyl-3-(3-dimethylaminopropyl)carbodiimide hydrochloride (EDCI), 1-ethyl-3-(3-dimethylaminopropyl)carbodiimide (EDAC), isobutyl chloroformate (IBCF), 1,1'-carbonylbis-1H-imidazole (CDI), diethyl cyanophosphonate (DEPC), diphenylphosphoryl azide (DPPA), N-hydroxysuccinimide, N-hydroxy-5-norbornene-2,3-dicarboxyimide and dipyridyl disulfide. The condensing agent may be used in the presence of 1-hydroxybenzotriazole (HOBt) or 1-hydroxybenzotriazole monohydrate as necessary. The condensing agent is preferably EDCI.

The base used in this step is preferably triethylamine, N-methylmorpholine or 4-(N,N-dimethylamino)pyridine.

The reaction temperature in this step is usually –50° C. to 100° C., and preferably –20° C. to 60° C.

The reaction time in this step is usually 0.1 to 24 hours, and preferably 0.5 to 10 hours.

Step B2

This step is a step of producing a compound represented by the general formula (VIII).

This step is carried out by reacting the compound represented by the general formula (X) with an acid in a solvent.

The solvent used in this step is preferably an ether, an amide or an alcohol, and more preferably 1,4-dioxane, N,N-dimethylformamide or ethanol.

The acid used in this step is preferably hydrochloric acid, sulfuric acid, nitric acid or benzenesulfonic acid, and more preferably hydrochloric acid.

The reaction temperature in this step is usually –20° C. to 150° C., and preferably 0° C. to 100° C.

The reaction time in this step is usually 0.5 to 150 hours, and preferably 1 to 72 hours.

Step B3

This step is a step of producing a compound represented by the general formula (I).

This step is carried out in the same manner as in Step A5 of the above Process A.

Process C is another process for producing a compound represented by the general formula (I).

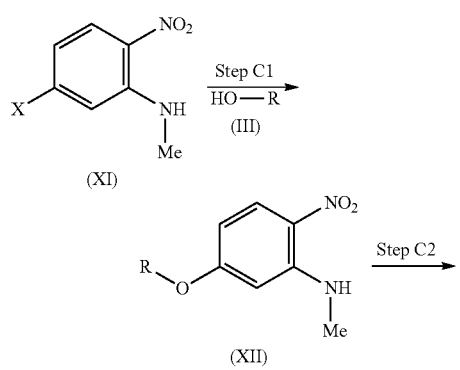

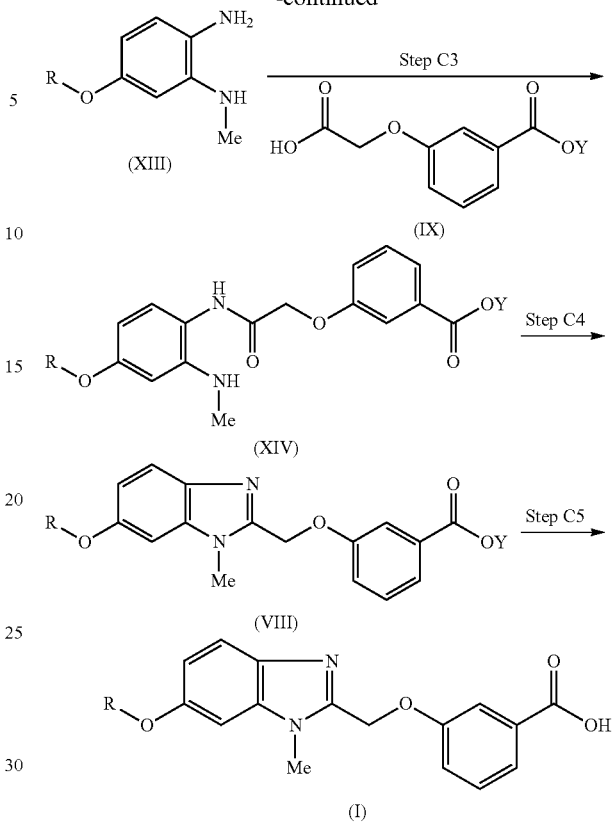

Step C1

This step is a step of producing a compound represented by the general formula (XII).

This step is carried out by reacting a compound represented by the general formula (XI) with a compound represented by the general formula (III) in a solvent in the presence of a base.

The compound represented by the general formula (XI) used in this step is a known compound or is easily produced from a known compound as a starting material by a known method or a method similar to a known method.

The solvent used in this step is preferably an amide, and more preferably N,N-dimethylformamide or N-methyl-2-pyrrolidone.

The base used in this step is preferably an alkali metal hydride, and more preferably sodium hydride.

The reaction temperature in this step is usually –78° C. to 150° C., and preferably 0° C. to 100° C.

The reaction time in this step is usually 0.5 to 48 hours, and preferably 1 to 24 hours.

Step C2

This step is a step of producing a compound represented by the general formula (XIII).

This step is carried out in the same manner as in Step A2 of the above Process A by reacting the compound represented by the general formula (XII) with iron in a solvent in the presence of a weak acid or by reducing the compound represented by the general formula (XII) in a solvent in the presence of a palladium catalyst in a hydrogen atmosphere.

Step C3

This step is a step of producing a compound represented by the general formula (XIV).

This step is carried out in the same manner as in Step B1 of the above Process B by reacting the compound represented by the general formula (XIII) with a compound represented by the general formula (IX) in a solvent in the presence of a condensing agent and a base.

Step C4

This step is a step of producing a compound represented by the general formula (VIII).

This step is carried out in the same manner as in Step B2 of the above Process B by reacting the compound represented by the general formula (XIV) with acetic acid.

Step C5

This step is a step of producing a compound represented by the general formula (I).

This step is carried out in the same manner as in Step A5 of the above Process A.

Process D is another process for producing a compound represented by the general formula (I).

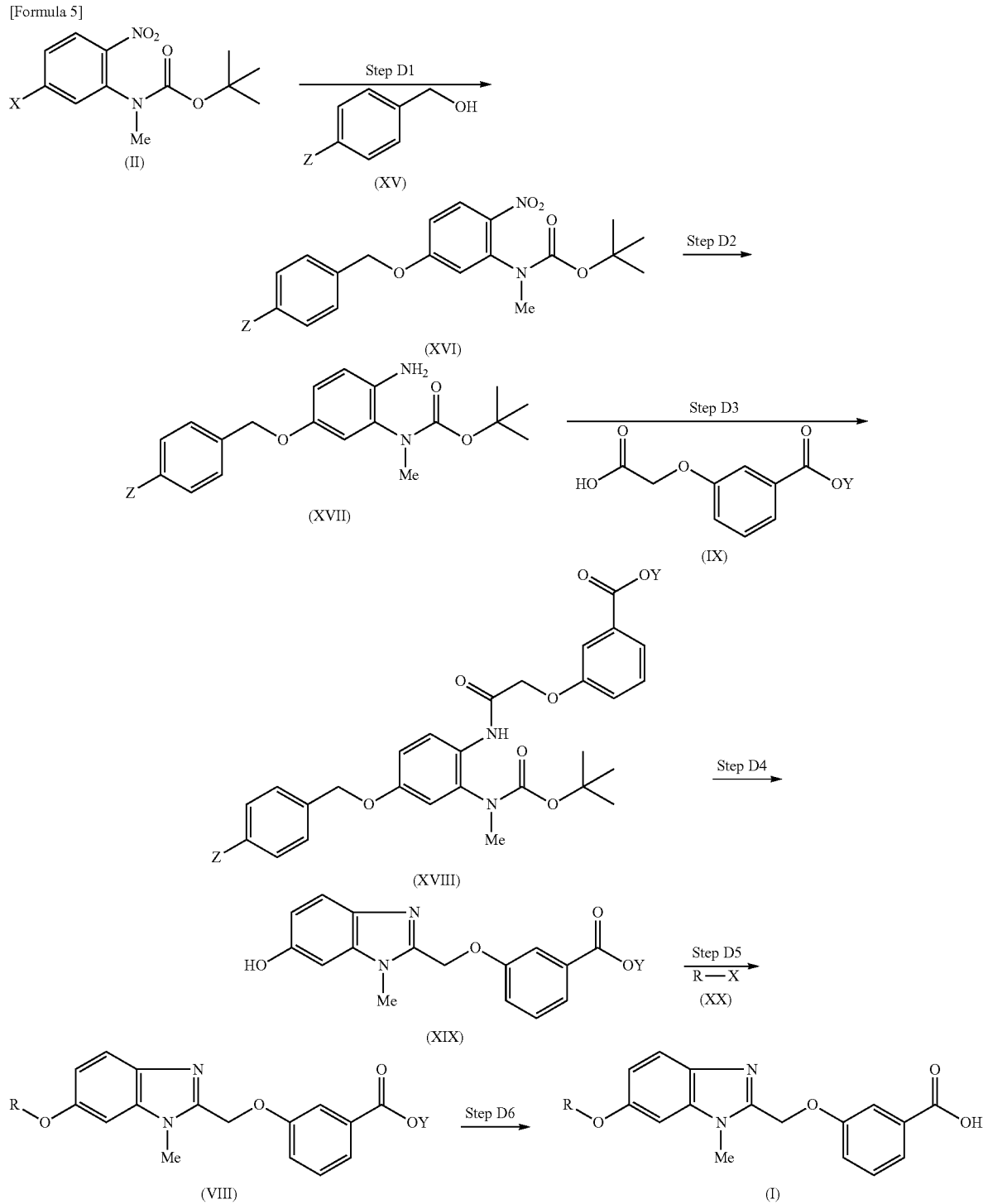

Step D1

This step is a step of producing a compound represented by the general formula (XVI).

This step is carried out by reacting a compound represented by the general formula (II) with a compound represented by the general formula (XV) in a solvent in the presence of a base.

The compound represented by the general formula (XV) used in this step is a known compound or is easily produced from a known compound as a starting material by a known method or a method similar to a known method.

The solvent used in this step is preferably an amide, and more preferably N,N-dimethylformamide or N-methyl-2-pyrrolidone.

The base used in this step is preferably an alkali metal carbonate or an alkali metal hydride, and more preferably cesium carbonate or sodium hydride.

The reaction temperature in this step is usually 50° C. to 150° C., and preferably 80° C. to 120° C.

The reaction time in this reaction is usually 0.5 to 48 hours, and preferably 1 to 30 hours.

Step D2

This step is a step of producing a compound represented by the general formula (XVII).

This step is carried out in the same manner as in Step A2 of the above Process A by reacting the compound represented by the general formula (XVI) with iron in a solvent in the presence of a weak acid or by reducing the compound represented by the general formula (XVI) in a solvent in the presence of a palladium catalyst in a hydrogen atmosphere.

Step D3

This step is a step of producing a compound represented by the general formula (XVIII).

This step is carried out in the same manner as in Step B1 of the above Process B by reacting the compound represented by the general formula (XVII) with a compound represented by the general formula (IX) in a solvent in the presence of a condensing agent and a base.

Step D4

This step is a step of producing a compound represented by the general formula (XIX).

This step is carried out by reacting the compound represented by the general formula (XVIII) with an acid in a solvent.

The solvent used in this step is preferably an ether or an alcohol, and more preferably dioxane or methanol.

Examples of the acid used in this step include hydrogen halides such as hydrogen chloride gas and hydrogen bromide gas; mineral acids such as sulfuric acid, hydrobromic acid and hydrochloric acid; organic sulfonic acids such as methanesulfonic acid, p-toluenesulfonic acid, pyridinium p-toluenesulfonate (PPTS), camphorsulfonic acid and trifluoromethanesulfonic acid; carboxylic acids such as acetic acid, formic acid and trifluoroacetic acid; methyl sulfate; Lewis acids such as aluminum chloride, zinc chloride, tin tetrachloride, titanium trichloride, titanium tetrachloride, boron trifluoride, boron trifluoride-diethyl ether and boron tribromide; and acidic ion exchange resins. The acid is preferably a mineral acid, more preferably sulfuric acid or hydrochloric acid, and still more preferably hydrochloric acid.

The reaction temperature in this step is usually 0° C. to 150° C., and preferably 20° C. to 120° C.

The reaction time in this reaction is usually 0.5 to 24 hours, and preferably 1 to 10 hours.

Step D5

This step is a step of producing a compound represented by the general formula (VIII).

This step is carried out by reacting the compound represented by the general formula (XIX) with a compound represented by the general formula (XX) in a solvent in the presence of copper and its ligand(s).

The compound represented by the general formula (XX) used in this step is a known compound or is easily produced from a known compound as a starting material by a known method or a method similar to a known method.

The solvent used in this step is preferably an ether or an amide, and more preferably tetrahydrofuran, N,N-dimethylformamide or N-methyl-2-pyrrolidone.

Examples of the copper used in this step include zerovalent copper and complexes thereof; monovalent copper salts such as copper (I) chloride, copper (I) bromide, copper (I) iodide and copper (I) trifluoromethanesulfonate, and complexes thereof; and divalent copper salts such as copper (II) bromide, copper (II) acetate and copper (II) sulfate, and complexes thereof. Preferred examples include monovalent copper salts and complexes thereof, and divalent copper salts. More preferred examples include copper (I) chloride, a copper (I) bromide-dimethyl sulfide complex, copper (I) iodide, copper (I) trifluoromethanesulfonate and copper (II) acetate. Still more preferred examples include copper (I) iodide.

The ligand used in this step is preferably N,N'-dimethylethylenediamine, trans-N,N'-dimethylcyclohexane-1,2-diamine, 2-(diphenylphosphino)-2'-(N,N-dimethylamino)biphenyl or 1,10-phenanthroline, and more preferably 1,10-phenanthroline.

The reaction temperature in this step is usually 0° C. to 150° C., and preferably 20° C. to 100° C.

The reaction time in this reaction is usually 0.5 to 24 hours, and preferably 1 to 10 hours.

Step D6

This step is a step of producing a compound represented by the general formula (I).

This step is carried out in the same manner as in Step A5 of the above Process A.

The compound represented by the general formula (I) or pharmacologically acceptable ester thereof, or pharmacologically acceptable salt of the compound or ester according to the present invention used as a medicine can be orally administered as tablets, capsules, granules, powder or syrup or parenterally administered as an injection or suppository, for example, alone or in a mixture with an appropriate pharmacologically acceptable excipient, diluent or the like.

These preparations are produced by known methods using additives such as excipients (whose examples include organic excipients such as sugar derivatives such as lactose, sucrose, glucose, mannitol and sorbitol; starch derivatives such as corn starch, potato starch, α-starch and dextrin; cellulose derivatives such as crystalline cellulose; gum arabic; dextran; and pullulan; and inorganic excipients such as silicate derivatives such as light silicic anhydride, synthetic aluminum silicate, calcium silicate and magnesium aluminometasilicate; phosphates such as calcium hydrogenphosphate; carbonates such as calcium carbonate; and sulfates such as calcium sulfate), lubricants (whose examples include stearic acid and stearic acid metal salts such as calcium stearate and magnesium stearate; talc; colloidal silica; waxes such as veegum and spermaceti; boric acid; adipic acid; sulfates such as sodium sulfate; glycol; fumaric acid; sodium benzoate; DL-leucine; fatty acid sodium salts; lauryl sulfates such as sodium lauryl sulfate and magnesium lauryl sulfate; silicic acids such as silicic anhydride and silicic acid hydrate; and the aforementioned starch derivatives), binders (whose examples include hydroxypropylcellulose, hydroxypropylmethylcellulose, polyvinylpyrrolidone, macrogol and the same compounds as the aforementioned excipients), disintegrants (whose examples include cellulose derivatives such as low-substituted hydroxypropylcellulose, carboxymethylcellulose, calcium carboxymethylcellulose and internally crosslinked sodium carboxymethylcellulose; and chemically modified starches such as carboxymethyl starch and sodium carboxymethyl starch), stabilizers (whose examples include parahydroxybenzoic acid esters such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid), corrigents (whose examples include commonly used sweeteners, acidulants and flavors) and diluents.

The dose of the preparation varies according to the symptoms, the age and the like of the patient (a warm-blooded animal, in particular, a human). However, the preparation is preferably orally administered at 0.0015 mg/kg body weight (preferably 0.008 mg/kg body weight) per dose per day at the lower limit to 70 mg/kg body weight (preferably 7 mg/kg body weight) per dose per day at the upper limit or intravenously administered at 0.00015 mg/kg body weight (preferably 0.0008 mg/kg body weight) per dose per day at the lower limit to 8.5 mg/kg body weight (preferably 5 mg/kg body weight) per dose per day at the upper limit to an adult once to six times per day according to the symptoms.

EXAMPLES

The present invention will be described in more detail below with reference to Examples, Test Examples and Preparation Examples; however, the scope of the present invention is not limited thereto.

Chromatographic elution in Examples was carried out under observation by TLC (Thin Layer Chromatography). In TLC observation, silica gel 60$F_{254}$ manufactured by Merck & Co., Inc. was used as the TLC plate, the solvent used as the elution solvent in column chromatography was used as the developing solvent, and a UV detector was used as the detection method. Silica gel SK-85 (230 to 400 mesh) or silica gel SK-34 (70 to 230 mesh) also manufactured by Merck & Co., Inc., or Chromatorex N.H. (200 to 350 mesh) manufactured by Fuji Silysia Chemical Ltd. was used as the column silica gel. An automatic chromatography system manufactured by Biotage AB (SP-1) was appropriately used in addition to a common column chromatography system. The abbreviations used in Examples have the following meanings:

mg: milligram, g: gram, mL: milliliter, MHz: megahertz.

In the following Examples, in nuclear magnetic resonance (hereinafter $^1$H NMR) spectra, chemical shifts are described in δ values (ppm) using tetramethylsilane as a reference substance. For splitting patterns, s represents singlet, d represents doublet, t represents triplet, and q represents quartet.

Mass spectrometry (hereinafter MS) was carried out by FAB (Fast Atom Bombardment), EI (Electron Ionization) or ESI (Electron Spray Ionization).

Example 1

3-({6-[(3-Chloropyridin-2-yl)oxy]-1-methyl-1H-benzimidazol-2-yl}methoxy)benzoic acid

[Formula 6]

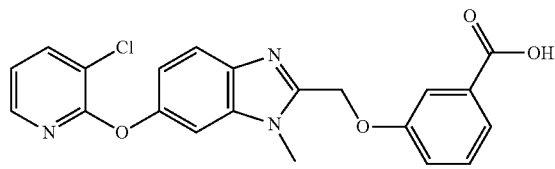

(1a) tert-Butyl {5-[(4-methoxybenzyl)oxy]-2-nitrophenyl}methylcarbamate

Sodium hydride (63%, 25 g, 656 mmol) was added to a solution of 4-methoxybenzyl alcohol (90.3 g, 654 mmol) and tert-butyl (5-chloro-2-nitrophenyl)methylcarbamate (US200216506A1, 156 g, 544 mmol) in DMF (1.4 L) at room temperature, and the mixture was stirred at 80° C. for four hours. After leaving to cool, water (1.5 L) was added to the reaction mixture. The precipitated solid was collected by filtration to obtain the title compound (209 g, 99%) as a yellow solid.

$^1$H-NMR (400 MHz, CDCl$_3$): δ ppm: 1.28 (9H, s), 3.25 (3H, s), 3.81 (3H, s), 5.04 (2H, s), 6.79-6.95 (4H, m), 7.29-7.37 (2H, m), 7.91-8.03 (1H, m).

(1b) tert-Butyl {2-amino-5-[(4-methoxybenzyl)oxy]phenyl}methylcarbamate

A solution of tert-butyl {5-[(4-methoxybenzyl)oxy]-2-nitrophenyl}methylcarbamate produced in Example (1a) (209 g, 538 mmol), iron powder (150 g, 2.69 mol) and ammonium chloride (15.0 g, 280 mmol) in ethanol (1.2 L) and water (1 L) was stirred with heating under reflux for five hours. After leaving to cool, the reaction mixture was filtered through celite. The filtrate was concentrated to about half volume under reduced pressure, and the concentrated residue was extracted with toluene (1 L) twice. The organic layer was dried over anhydrous sodium sulfate and concentrated under reduced pressure to obtain the title compound (193 g, 99%) as a brown oil.

$^1$H-NMR (400 MHz, CDCl$_3$): δ ppm: 1.38 (9H, brs), 3.15 (3H, s), 3.49 (2H, brs), 3.82 (3H, s), 4.91 (2H, s), 6.70 (1H, d, J=8.6 Hz), 6.68-6.71 (1H, m), 6.76 (1H, dd, J=2.4, 8.6 Hz), 6.91 (2H, d, J=8.6 Hz), 7.34 (2H, d, J=8.6 Hz).

(1c) [3-(Methoxycarbonyl)phenoxy]acetic acid

A solution of t-butyl bromoacetate (506 g, 2.59 mol), methyl 3-hydroxybenzoate (395 g, 2.60 mol) and potassium carbonate (789 g, 5.71 mol) in DMF (2 L) was stirred at room temperature for two hours. The reaction mixture was concentrated and then water (1 L) was added, followed by extraction with ethyl acetate (2 L). The organic layer was washed with water (1 L) twice, dried over anhydrous sodium sulfate and concentrated under reduced pressure to obtain t-butyl [3-(methoxycarbonyl)phenoxy]acetate as a colorless oil.

A solution of t-butyl [3-(methoxycarbonyl)phenoxy]acetate in trifluoroacetic acid (1 kg), anisole (100 mL) and dichloromethane (1 L) was stirred at room temperature for 48 hours. The reaction mixture was concentrated and then the residue was crystallized from diisopropyl ether to obtain the title compound (467 g, 86%) as a white solid.

$^1$H-NMR (400 MHz, CDCl$_3$): δ ppm: 3.93 (3H, s), 4.76 (2H, s), 7.17 (1H, dd, J=2.4, 8.2 Hz), 7.39 (1H, t, J=7.8 Hz), 7.57-7.58 (1H, m), 7.72 (1H, d, J=7.4 Hz).

(1d) Methyl 3-[2-({2-[(tert-butoxycarbonyl)(methyl)amino]-4-[(4-methoxybenzyl)oxy]phenyl}amino)-2-oxoethoxy]benzoate A solution of [3-(methoxycarbonyl)phenoxy]acetic acid produced in Example (1c) (121 g, 577 mmol), tert-Butyl {2-amino-5-[(4-methoxybenzyl)oxy]phenyl}methylcarbamate produced in Example (1b) (193 g, 538 mmol), 1-hydroxybenzotriazole (77.7 g, 575 mmol) and 1-ethyl-3-(3-dimethylaminopropyl)carbodiimide hydrochloride (110 g, 575 mmol) in methylene chloride (1 L) was stirred at room temperature for three hours. Water (1 L) was added to the reaction mixture, and the precipitated solid was removed by filtration through celite. The separated organic layer was dried over anhydrous sodium sulfate and the organic solvent was evaporated under reduced pressure. The concentrated residue was recrystallized from a mixed solvent of diisopropyl ether/ethyl acetate (20:1) to obtain the title compound (296 g, 99%) as a white solid.

$^1$H-NMR (400 MHz, CDCl$_3$): δ ppm: 1.43 (9H, brs), 3.12 (3H, s), 3.83 (3H, s), 3.93 (3H, s), 4.67 (2H, s), 4.98 (2H, s), 6.80 (1H, brs), 6.93 (4H, d, J=8.6 Hz), 7.21-7.27 (2H, m), 7.35 (2H, d, J=8.6 Hz), 7.42 (1H, t, J=8.2 Hz), 7.64 (1H, s), 7.75 (1H, d, J=8.2 Hz).

(1e) Methyl 3-[(6-hydroxy-1-methyl-1H-benzimidazol-2-yl)methoxy]benzoate

Methyl 3-[2-({2-[(tert-butoxycarbonyl)(methyl)amino]-4-[(4-methoxybenzyl)oxy]phenyl}amino)-2-oxoethoxy]benzoate produced in Example (1d) (296 g, 538 mmol), a 4 M hydrochloric acid/1,4-dioxane solution (500 mL) and 1,4-dioxane (500 mL) was stirred at 60° C. for two hours. After leaving to cool, the precipitated solid was collected by filtration to obtain a hydrochloride of the title compound as a gray solid.

Water (500 mL) and a solution of imidazole (59 g, 867 mmol) in water (500 mL) were added to a suspension of the hydrochloride of the title compound in ethyl acetate (1 L). The precipitated solid was collected by filtration to obtain the title compound (113 g, 67%) as a gray solid.

$^1$H-NMR (400 MHz, DMSO-d$_6$): δ ppm: 3.74 (3H, s), 3.85 (3H, s), 5.40 (2H, s), 6.71 (1H, dd, J=2.4, 8.6 Hz), 6.83 (1H, d, J=2.0 Hz), 7.40-7.43 (2H, m), 7.47 (1H, t, J=7.4 Hz), 7.58 (1H, dt, J=1.6, 7.8 Hz), 7.63-7.64 (1H, m), 9.36 (1H, s).

(1f) Methyl 3-({6-[(3-chloropyridin-2-yl)oxy]-1-methyl-1H-benzimidazol-2-yl}methoxy)benzoate A solution of methyl 3-[(6-hydroxy-1-methyl-1H-benzimidazol-2-yl)methoxy]benzoate produced in Example (1e) (3.12 g, 10 mmol), 3-chloro-2-fluoropyridine (1.45 g, 11 mmol), copper iodide (0.19 g, 1.0 mmol), 1,10-phenanthroline (0.18 g, 1.0 mmol) and cesium carbonate (9.77 g, 30 mmol) in DMF (50 mL) was stirred in a nitrogen atmosphere at 80° C. for two hours. After leaving to cool, a saturated ammonium chloride aqueous solution (200 mL) was added to the reaction mixture, followed by extraction with ethyl acetate (200 mL). Then, the organic layer was washed with water (200 mL) twice and dried over anhydrous sodium sulfate. After concentration under reduced pressure, the residue was purified by silica gel chromatography (methylene chloride/methanol, 95:5) to obtain the title compound (2.46 g, 58%) as a white solid.

$^1$H-NMR (400 MHz, CDCl$_3$): δ ppm: 3.87 (3H, s), 3.93 (3H, s), 5.42 (2H, s), 6.98 (1H, dd, J=4.7, 7.4 Hz), 7.10 (1H, dd, J=2.4, 9.0 Hz), 7.22 (1H, d, J=2.0 Hz), 7.30 (1H, dd, J=1.0, 8.6 Hz), 7.38 (1H, t, J=7.8 Hz), 7.70 (1H, d, J=7.4 Hz), 7.72-7.73 (1H, m), 7.79 (1H, dd, J=1.6, 7.4 Hz), 7.80 (1H, d, J=8.6 Hz), 8.02 (1H, dd, J=1.6, 4.7 Hz).

(1g) 3-({6-[(3-Chloropyridin-2-yl)oxy]-1-methyl-1H-benzimidazol-2-yl}methoxy)benzoic acid Methyl 3-({6-[(3-chloropyridin-2-yl)oxy]-1-methyl-1H-benzimidazol-2-yl}methoxy)benzoate produced in Example (1f) (2.46 g, 5.8 mmol), a 2 M sodium hydroxide aqueous solution (10 mL) and 1,4-dioxane (20 mL) were stirred at 80° C. for two hours. After leaving to cool, the reaction mixture was concentrated and water (100 mL) was added. This aqueous solution was neutralized by adding 1 M hydrochloric acid and the precipitated solid was collected by filtration to obtain the title compound (1.59 g, 67%) as a white solid.

$^1$H-NMR (400 MHz, DMSO-d$_6$): δ ppm: 3.83 (3H, s), 5.49 (2H, s), 7.01 (1H, dd, J=2.4, 9.0 Hz), 7.15 (1H, dd, J=5.1, 7.8 Hz), 7.37-7.40 (1H, m), 7.45 (1H, t, J=7.4 Hz), 7.49 (1H, d, J=2.4 Hz), 7.57 (1H, d, J=7.8 Hz), 7.63-7.64 (1H, m), 7.67 (1H, d, J=8.6 Hz), 8.03 (1H, dd, J=2.0, 5.1 Hz), 8.06 (1H, dd, J=1.6, 7.8 Hz), 13.06 (1H, brs);

Anal. Calcd for C$_{21}$H$_{16}$ClN$_3$O$_4$: C, 61.54; H, 3.94; N, 10.25.
Found C, 61.40; H, 3.86; N, 10.17.

Example 2

3-({6-[(3-Ethylpyridin-2-yl)oxy]-1-methyl-1H-benzimidazol-2-yl}methoxy)benzoic acid

[Formula 7]

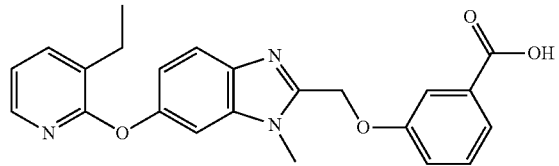

(2a) Methyl 3-({6-[(3-bromopyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (3.12 g, 10 mmol), 3-bromo-2-fluoropyridine (1.94 g, 11 mmol), copper iodide (0.19 g, 1.0 mmol), 1,10-phenanthroline (0.18 g, 1.0 mmol), cesium carbonate (9.77 g, 30 mmol) and DMF (50 mL) to obtain the title compound (2.19 g, 47%) as a white solid.

$^1$H-NMR (400 MHz, CDCl$_3$): δ ppm: 3.87 (3H, s), 3.93 (3H, s), 5.42 (2H, s), 6.91 (1H, dd, J=5.1, 8.6 Hz), 7.10 (1H, dd, J=2.7, 8.6 Hz), 7.21 (1H, d, J=2.4 Hz), 7.30 (1H, dd, J=0.8, 8.2 Hz), 7.38 (1H, t, J=7.8 Hz), 7.68 (1H, d, J=7.8 Hz), 7.72-7.73 (1H, m), 7.80 (1H, d, J=8.6 Hz), 7.96 (1H, dd, J=2.0, 8.6 Hz), 8.06 (1H, dd, J=1.6, 4.7 Hz).

(2b) Methyl 3-({6-[(3-ethylpyridin-2-yl)oxy]-1-methyl-1H-benzimidazol-2-yl}methoxy)benzoate A solution of methyl 3-({6-[(3-bromopyridin-2-yl)oxy]-1-methyl-1H-benzimidazol-2-yl}methoxy)benzoate produced in Example (2a) (1.20 g, 2.56 mmol), triethylborane (1.0 M solution in THF, 5.12 mL, 5.12 mmol), a [1,1'-bis(diphenylphosphino)-ferrocene]dichloropalladium (II)-dichloromethane mixture (0.21 g, 0.26 mmol) and potassium carbonate (0.71 g, 5.12 mmol) in DMF (10 mL) was stirred in a nitrogen atmosphere at 80° C. for two days. After leaving to cool, water (50 mL) was added to the reaction mixture, followed by extraction with ethyl acetate (50 mL). Then, the organic layer was washed with water (100 mL) twice and dried over anhydrous sodium sulfate. After concentration under reduced pressure, the residue was purified by reverse phase column chromatography (acetonitrile/water, 2:1) to obtain the title compound (0.55 g, 51%) as a white solid.

$^1$H-NMR (400 MHz, CDCl$_3$): δ ppm: 1.33 (3H, t, J=7.4 Hz), 2.81 (2H, q, J=7.4 Hz), 3.85 (3H, s), 3.93 (3H, s), 5.42 (2H, s), 6.95 (1H, dd, J=5.1, 7.4 Hz), 7.05 (1H, dd, J=2.4, 8.6 Hz), 7.16 (1H, d, J=2.4 Hz), 7.28-7.31 (1H, m), 7.37 (1H, t, J=8.2 Hz), 7.57 (1H, dd, J=2.0, 7.0 Hz), 7.68-7.70 (1H, m), 7.72-7.73 (1H, m), 7.78 (1H, d, J=8.6 Hz), 7.99 (1H, dd, J=2.0, 4.7 Hz).

(2c) 3-({6-[(3-Ethylpyridin-2-yl)oxy]-1-methyl-1H-benzimidazol-2-yl}methoxy)benzoic acid The reaction and post-treatment were carried out according to Example (1g) using methyl 3-({6-[(3-ethylpyridin-2-yl)oxy]-1-methyl-1H-benzimidazol-2-yl}methoxy)benzoate produced in Example (2b) (0.55 g, 1.32 mmol), a 2 M sodium hydroxide aqueous solution (5 mL) and 1,4-dioxane (10 mL) to obtain the title compound (0.44 g, 89%) as a white solid.

$^1$H-NMR (400 MHz, DMSO-d$_6$): δ ppm: 1.27 (3H, t, J=7.8 Hz), 2.74 (2H, q, J=7.4 Hz), 3.82 (3H, s), 5.48 (2H, s), 6.94 (1H, dd, J=2.4, 8.2 Hz), 7.05 (1H, dd, J=4.7, 7.0 Hz), 7.38-7.40 (2H, m), 7.45 (1H, t, J=7.8 Hz), 7.57 (1H, d, J=7.4 Hz), 7.62-7.64 (2H, m), 7.71 (1H, dd, J=1.2, 7.4 Hz), 7.90 (1H, dd, J=1.2, 4.7 Hz), 13.05 (1H, brs);

Anal. Calcd for C$_{23}$H$_{21}$N$_3$O$_4$: C, 68.47; H, 5.25; N, 10.42. Found C, 68.21; H, 5.15; N, 10.39.

Example 3

3-({6-[(6-Methoxy-5-methylpyridin-2-yl)oxy]-1-methyl-1H-benzimidazol-2-yl}methoxy)benzoic acid

[Formula 8]

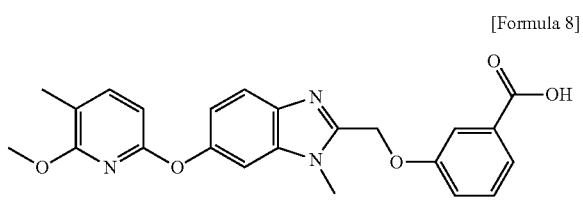 [SMILES: COc1nc(Oc2ccc3nc(COc4cccc(C(=O)O)c4)n(C)c3c2)ccc1C]

(3a) Methyl 3-({6-[(5-bromo-6-chloropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (1.56 g, 5.0 mmol), 3-bromo-2-chloro-6-fluoropyridine (1.16 g, 5.50 mmol), copper iodide (0.10 g, 0.50 mmol), 1,10-phenanthroline (0.09 g, 0.50 mmol), cesium carbonate (4.89 g, 15 mmol) and DMF (30 mL) to obtain the title compound (1.70 g, 68%) as a white solid.

$^1$H-NMR (400 MHz, DMSO-d$_6$): δ ppm: 3.84 (3H, s), 3.86 (3H, s), 5.50 (2H, s), 6.98 (1H, dd, J=0.8, 9.0 Hz), 7.05 (1H, d, J=9.9 Hz), 7.42-7.52 (3H, m), 7.59 (1H, d, J=8.2 Hz), 7.67-7.71 (2H, m), 8.22 (1H, dd, J=1.6, 8.6 Hz).

(3b) Methyl 3-({6-[(5-bromo-6-methoxypyridin-2-yl)oxy]-1-methyl-1H-benzimidazol-2-yl}methoxy)benzoate Methyl 3-({6-[(5-bromo-6-chloropyridin-2-yl)oxy]-1-methyl-1H-benzimidazol-2-yl}methoxy)benzoate produced in Example (3a) (0.74 g, 1.47 mmol), sodium methoxide (5.0 M solution in methanol, 2.94 mL, 14.7 mmol), water (10 mL) and 1,4-dioxane (20 mL) were stirred with heating under reflux for three days. After leaving to cool, the reaction mixture was concentrated and water (50 mL) was added. This aqueous solution was neutralized by adding 1 M hydrochloric acid and the precipitated solid was collected by filtration to obtain crude 3-({6-[(5-bromo-6-methoxypyridin-2-yl)oxy]-1-methyl-1H-benzimidazol-2-yl}methoxy)benzoic acid. Trimethylsilyldiazomethane (2.0 M solution in hexane) was added to a solution of the crude 3-({6-[(5-bromo-6-methoxypyridin-2-yl)oxy]-1-methyl-1H-benzimidazol-2-yl}methoxy)benzoic acid in toluene (20 mL) and methanol (10 mL) until the raw material disappeared. The reaction mixture was concentrated under reduced pressure. Then, the residue was purified by silica gel chromatography (hexane/ethyl acetate, 1:1) to obtain the title compound (0.36 g, 49%) as a white solid.

$^1$H-NMR (400 MHz, CDCl$_3$): δ ppm: 3.86 (3H, s), 3.87 (3H, s), 3.94 (3H, s), 5.42 (2H, s), 6.27 (1H, d, J=8.2 Hz), 7.10 (1H, dd, J=2.4, 9.0 Hz), 7.17 (1H, d, J=2.0 Hz), 7.30 (1H, dd, J=2.0, 8.2 Hz), 7.39 (1H, t, J=7.8 Hz), 7.69-7.78 (4H, m).

(3c) Methyl 3-({6-[(6-methoxy-5-methylpyridin-2-yl)oxy]-1-methyl-1H-benzimidazol-2-yl}methoxy)benzoate The reaction and post-treatment were carried out according to Example (2b) using methyl 3-({6-[(5-bromo-6-methoxypyridin-2-yl)oxy]-1-methyl-1H-benzimidazol-2-yl}methoxy)benzoate produced in Example (3b) (0.36 g, 0.72 mmol), trimethylboroxine (50% solution in THF, 0.40 mL, 1.43 mmol), a [1, 1'-bis(diphenylphosphino)-ferrocene]dichloropalladium (II)-dichloromethane mixture (59 mg, 0.07 mmol), potassium carbonate (0.20 g, 1.43 mmol) and DMF (10 mL) to obtain the title compound (0.26 g, 85%) as a white solid.

$^1$H-NMR (400 MHz, CDCl$_3$): δ ppm: 2.15 (3H, s), 3.85 (3H, s), 3.86 (3H, s), 3.93 (3H, s), 5.41 (2H, s), 6.20 (1H, d, J=7.8 Hz), 7.10 (1H, dd, J=2.0, 8.6 Hz), 7.16 (1H, d, J=2.0 Hz), 7.30-7.32 (1H, m), 7.34 (1H, dd, J=0.8, 7.8 Hz), 7.39 (1H, t, J=7.8 Hz), 7.69-7.76 (3H, m).

(3d) 3-({6-[(6-Methoxy-5-methylpyridin-2-yl)oxy]-1-methyl-1H-benzimidazol-2-yl}methoxy)benzoic acid The reaction and post-treatment were carried out according to Example (1g) using methyl 3-({6-[(6-methoxy-5-methylpyridin-2-yl)oxy]-1-methyl-1H-benzimidazol-2-yl}methoxy)benzoate produced in Example (3c) (0.26 g, 0.61 mmol), a 1 M sodium hydroxide aqueous solution (20 mL) and 1,4-dioxane (40 mL) to obtain the title compound (0.22 g, 87%) as a white solid.

$^1$H-NMR (400 MHz, DMSO-d$_6$): δ ppm: 2.09 (3H, s), 3.70 (3H, s), 3.83 (3H, s), 5.47 (2H, s), 6.32 (1H, d, J=7.8 Hz), 7.00 (1H, dd, J=2.0, 8.6 Hz), 7.38 (1H, dd, J=2.4, 7.8 Hz), 7.43-7.47 (2H, m), 7.53 (1H, d, J=7.8 Hz), 7.58 (1H, d, J=7.8 Hz), 7.64-7.67 (2H, m), 13.04 (1H, brs);

Anal. Calcd for C$_{23}$H$_{21}$N$_3$O$_5$.0.25H$_2$O: C, 65.16; H, 5.11; N, 9.91. Found C, 65.45; H, 4.98; N, 9.96.

Example 4

3-({6-[(5,6-Dimethylpyridin-2-yl)oxy]-1-methyl-1H-benzimidazol-2-yl}methoxy)benzoic acid

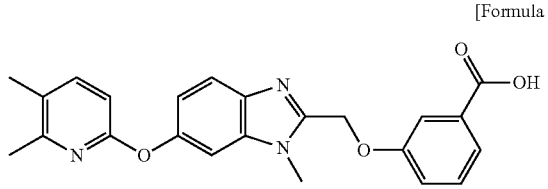

[Formula 9]

(4a) Methyl 3-({6-[(5-bromo-6-methylpyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (3.12 g, 10 mmol), 3-bromo-6-fluoro-2-methylpyridine (2.09 g, 11 mmol), copper iodide (0.19 g, 1.0 mmol), 1,10-phenanthroline (0.18 g, 1.0 mmol), cesium carbonate (9.77 g, 30 mmol) and DMF (50 mL) to obtain the title compound (0.68 g, 14%) as a white solid.

$^1$H-NMR (400 MHz, CDCl$_3$): δ ppm: 2.54 (3H, s), 3.86 (3H, s), 3.93 (3H, s), 5.42 (2H, s), 6.53 (1H, d, J=8.6 Hz), 7.07 (1H, dd, J=2.4, 8.6 Hz), 7.15 (1H, d, J=2.0 Hz), 7.31 (1H, ddd, J=1.2, 2.7, 8.2 Hz), 7.39 (1H, t, J=7.4 Hz), 7.69-7.73 (2H, m), 7.77 (1H, d, J=8.6 Hz).

(4b) Methyl 3-({6-[(5,6-dimethylpyridin-2-yl)oxy]-1-methyl-1H-benzimidazol-2-yl}methoxy)benzoate The reaction and post-treatment were carried out according to Example (2b) using methyl 3-({6-[(5-bromo-6-methylpyridin-2-yl)oxy]-1-methyl-1H-benzimidazol-2-yl}methoxy)benzoate produced in Example (4a) (0.68 g, 1.41 mmol), trimethylboroxine (50% solution in THF, 0.39 mL, 1.41 mmol), a [1,1'-bis(diphenylphosphino)-ferrocene] dichloropalladium (II)-dichloromethane mixture (0.12 g, 0.14 mmol), potassium carbonate (0.39 g, 2.82 mmol) and DMF (5 mL) to obtain the title compound (0.17 g, 29%) as a white solid.

$^1$H-NMR (400 MHz, CDCl$_3$): δ ppm: 2.24 (3H, s), 2.42 (3H, s), 3.85 (3H, s), 3.93 (3H, s), 5.41 (2H, s), 6.51 (1H, d, J=8.2 Hz), 7.07 (1H, dd, J=2.0, 8.6 Hz), 7.13 (1H, d, J=2.0 Hz), 7.29 (1H, ddd, J=1.2, 3.1, 8.6 Hz), 7.38 (1H, d, J=7.8 Hz), 7.39 (1H, t, J=7.8 Hz), 7.69-7.76 (3H, m).

(4c) 3-({6-[(5,6-Dimethylpyridin-2-yl)oxy]-1-methyl-1H-benzimidazol-2-yl}methoxy)benzoic acid The reaction and post-treatment were carried out according to Example (1g) using methyl 3-({6-[(5,6-dimethylpyridin-2-yl)oxy]-1-methyl-1H-benzimidazol-2-yl}methoxy)benzoate produced in Example (4b) (0.17 g, 0.41 mmol), a 2 M sodium hydroxide aqueous solution (5 mL) and 1,4-dioxane (10 mL) to obtain the title compound (0.16 g, 99%) as a white solid.

$^1$H-NMR (400 MHz, DMSO-d$_6$): δ ppm: 2.19 (3H, s), 2.25 (3H, s), 3.82 (3H, s), 5.47 (2H, s), 6.66 (1H, d, J=7.8 Hz), 6.94 (1H, dd, J=2.4, 8.6 Hz), 7.37 (1H, d, J=2.0 Hz), 7.38 (1H, ddd, J=1.2, 2.7, 8.2 Hz), 7.45 (1H, t, J=7.4 Hz), 7.54 (1H, d, J=8.2 Hz), 7.58 (1H, dt, J=1.6, 6.3 Hz), 7.63-7.65 (2H, m), 13.03 (1H, brs);

Anal. Calcd for C$_{23}$H$_{21}$N$_3$O$_4$.0.33H$_2$O: C, 67.47; H, 5.33; N, 10.26. Found C, 67.40; H, 5.26; N, 10.27.

Example 5

3-({6-[(5-Chloro-3-fluoropyridin-2-yl)oxy]-1-methyl-1H-benzimidazol-2-yl}methoxy)benzoic acid

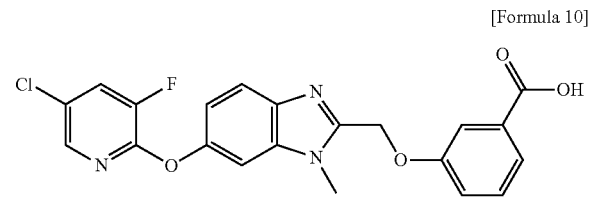 [SMILES: Cn1c(COc2cccc(C(=O)O)c2)nc2ccc(Oc3ncc(Cl)cc3F)cc21]

[Formula 10]

(5a) Methyl 3-({6-[(5-chloro-3-fluoropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (15.6 g, 50.0 mmol), 5-chloro-2,3-difluoropyridine (8.22 g, 55.0 mmol), copper iodide (0.95 g, 5.00 mmol), 1,10-phenanthroline (0.90 g, 5.00 mmol), cesium carbonate (48.9 g, 150 mmol) and DMF (200 mL) to obtain the title compound (15.4 g, 70%) as a white solid.

$^1$H-NMR (500 MHz, CDCl$_3$): δ ppm: 3.87 (3H, s), 3.93 (3H, s), 5.42 (2H, s), 7.09 (1H, dd, J=2.4, 8.8 Hz), 7.21 (1H, d, J=2.0 Hz), 7.30 (1H, ddd, J=1.0, 2.4, 8.3 Hz), 7.38 (1H, t, J=8.3 Hz), 7.54 (1H, dd, J=2.0, 8.8 Hz), 7.70 (1H, dt, J=1.0, 7.8 Hz), 7.73 (1H, dd, J=1.5, 2.4 Hz), 7.80 (1H, d, J=8.8 Hz), 7.88 (1H, d, J=2.0 Hz).

(5b) 3-({6-[(5-Chloro-3-fluoropyridin-2-yl)oxy]-1-methyl-1H-benzimidazol-2-yl}methoxy)benzoic acid The reaction and post-treatment were carried out according to Example (1g) using methyl 3-({6-[(5-chloro-3-fluoropyridin-2-yl)oxy]-1-methyl-1H-benzimidazol-2-yl}methoxy)benzoate produced in Example (5a) (15.4 g, 34.9 mmol), a 2 M sodium hydroxide aqueous solution (100 mL) and THF (200 mL) to obtain the title compound (14.0 g, 94%) as a white solid.

$^1$H-NMR (400 MHz, DMSO-d$_6$): δ ppm: 3.83 (3H, s), 5.49 (2H, s), 7.06 (1H, ddd, J=1.2, 2.4, 8.6 Hz), 7.37-7.40 (1H, m), 7.45 (1H, t, J=7.4 Hz), 7.52 (1H, d, J=2.4 Hz), 7.58 (1H, dd, J=1.6, 7.8 Hz), 7.64 (1H, t, J=1.2 Hz), 7.68 (1H, d, J=8.6 Hz), 8.02 (1H, dd, J=1.2, 2.4 Hz), 8.23 (1H, ddd, J=1.2, 2.0, 9.8 Hz), 13.06 (1H, s);

Anal. Calcd for C$_{21}$H$_{15}$ClFN$_3$O$_4$: C, 58.96; H, 3.53; N, 9.82.

Found C, 58.73; H, 3.40; N, 9.74.

Example 6

3-({6-[(5-Chloro-3-methylpyridin-2-yl)oxy]-1-methyl-1H-benzimidazol-2-yl}methoxy)benzoic acid

[Formula 11]

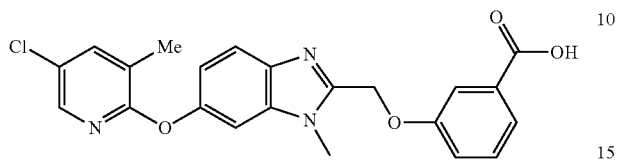

(6a) Methyl 3-({6-[(5-chloro-3-bromopyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (9.40 g, 30.0 mmol), 3-bromo-5-chloro-2-fluoropyridine (6.90 g, 33.0 mmol), copper iodide (0.57 g, 3.00 mmol), 1,10-phenanthroline (0.54 g, 3.00 mmol), cesium carbonate (29.3 g, 90 mmol) and DMF (90 mL) to obtain the title compound (13.7 g, 91%) as a white solid.

$^1$H-NMR (400 MHz, CDCl$_3$): δ ppm: 3.83 (3H, s), 3.89 (3H, s), 5.38 (2H, s), 6.96-7.01 (1H, m), 7.09-7.11 (1H, m), 7.23-7.27 (1H, m), 7.30-7.36 (1H, m), 7.48-7.50 (1H, m), 7.62-7.66 (1H, m), 7.67-7.70 (1H, m), 7.72-7.75 (1H, m), 7.85-7.87 (1H, m).

(6b) Methyl 3-({6-[(5-chloro-3-methylpyridin-2-yl)oxy]-1-methyl-1H-benzimidazol-2-yl}methoxy)benzoate The reaction and post-treatment were carried out according to Example (2b) using methyl 3-({6-[(5-chloro-3-bromopyridin-2-yl)oxy]-1-methyl-1H-benzimidazol-2-yl}methoxy)benzoate produced in Example (6a) (10.1 g, 20.0 mmol), trimethylboroxine (50% solution in THF, 6.2 mL, 44.0 mmol), a [1,1'-bis(diphenylphosphino)-ferrocene] dichloropalladium (II)-dichloromethane mixture (0.82 g, 1.00 mmol), potassium carbonate (8.29 g, 60.0 mmol) and DMF (80 mL) to obtain the title compound (6.60 g, 75%) as a white solid.

$^1$H-NMR (400 MHz, CDCl$_3$): δ ppm: 2.41 (3H, s), 3.82 (3H, s), 3.89 (3H, s), 5.38 (2H, s), 6.98-7.00 (1H, m), 7.09-7.11 (1H, m), 7.22-7.27 (1H, m), 7.31-7.37 (1H, m), 7.49-7.50 (1H, m), 7.64-7.66 (1H, m), 7.64-7.69 (1H, m), 7.74 (1H, d, J=8.6 Hz), 7.84-7.87 (1H, m).

(6c) 3-({6-[(5-Chloro-3-methylpyridin-2-yl)oxy]-1-methyl-1H-benzimidazol-2-yl}methoxy)benzoic acid The reaction and post-treatment were carried out according to Example (1g) using methyl 3-({6-[(5-chloro-3-methylpyridin-2-yl)oxy]-1-methyl-1H-benzimidazol-2-yl}methoxy)benzoate produced in Example (6b) (465 mg, 1.06 mmol), a 1 M sodium hydroxide aqueous solution (2.1 mL), THF (10 mL) and methanol (10 mL) to obtain the title compound (230 mg, 51%) as a white solid.

$^1$H-NMR (400 MHz, DMSO-d$_6$): δ ppm: 2.32 (3H, s), 3.79 (3H, s), 5.45 (2H, s), 6.94 (1H, dd, J=2.2. 8.8 Hz), 7.37-7.41 (3H, m), 7.53-7.55 (1H, m), 7.60-7.62 (2H, m), 7.83-7.85 (1H, m), 7.89-7.92 (1H, m), 13.01 (1H, s);

Anal. Calcd for C$_{22}$H$_{18}$ClN$_3$O$_4$: C, 58.96; H, 3.53; N, 9.82. Found C, 58.73; H, 3.40; N, 9.74;

FAB-MS m/z: 424 (M+H)$^+$.

Example 7

3-({6-[(3,5-Dichloropyridin-2-yl)oxy]-1-methyl-1H-benzimidazol-2-yl}methoxy)benzoic acid

[Formula 12]

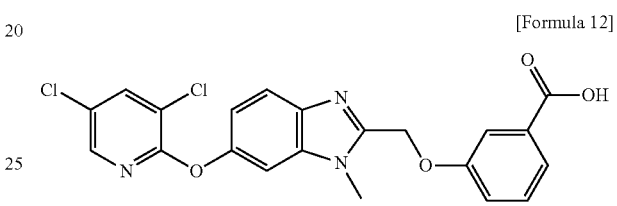

(7a) Methyl 3-({6-[(3,5-dichloropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (7.81 g, 25.0 mmol), 3,5-dichloro-2-fluoropyridine (4.57 g, 27.5 mmol), copper iodide (0.48 g, 2.50 mmol), 1,10-phenanthroline (0.45 g, 2.50 mmol), cesium carbonate (24.44 g, 75.0 mmol) and DMF (100 mL) to obtain the title compound (5.90 g, 53%) as a white solid.

$^1$H-NMR (400 MHz, CDCl$_3$): δ ppm: 3.87 (3H, s), 3.93 (3H, s), 5.42 (2H, s), 7.08 (1H, dd, J=2.0, 8.6 Hz), 7.20 (1H, s), 7.29-7.31 (1H, m), 7.38 (1H, t, J=8.2 Hz), 7.70 (1H, d, J=7.4 Hz), 7.73 (1H, s), 7.80 (1H, d, J=2.4 Hz), 7.82 (1H, brs), 7.96 (1H, d, J=2.4 Hz).

(7b) 3-({6-[(3,5-Dichloropyridin-2-yl)oxy]-1-methyl-1H-benzimidazol-2-yl}methoxy)benzoic acid The reaction and post-treatment were carried out according to Example (1g) using methyl 3-({6-[(3,5-dichloropyridin-2-yl)oxy]-1-methyl-1H-benzimidazol-2-yl}methoxy)benzoate produced in Example (7a) (5.90 g, 12.9 mmol), a 2 M sodium hydroxide aqueous solution (50 mL) and 1,4-dioxane (100 mL) to obtain the title compound (5.30 g, 93%) as a white solid.

$^1$H-NMR (400 MHz, DMSO-d$_6$): δ ppm: 3.83 (3H, s), 5.49 (2H, s), 7.04 (1H, dd, J=2.4, 9.0 Hz), 7.39 (1H, dd, J=2.4, 8.2 Hz), 7.45 (1H, t, J=7.8 Hz), 7.51 (1H, d, J=2.4 Hz), 7.57 (1H, d, J=7.4 Hz), 7.64 (1H, s), 7.68 (1H, d, J=9.0 Hz), 8.12 (1H, dd, J=0.8, 2.4 Hz), 8.36 (1H, d, J=2.4 Hz), 13.04 (1H, brs);

Anal. Calcd for C$_{21}$H$_{15}$Cl$_2$N$_3$O$_4$·0.25H$_2$O: C, 56.20; H, 3.48; N, 9.36. Found C, 56.20; H, 3.30; N, 9.53.

Example 8

3-({6-[(5-Fluoro-3-methylpyridin-2-yl)oxy]-1-methyl-1H-benzimidazol-2-yl}methoxy)benzoic acid

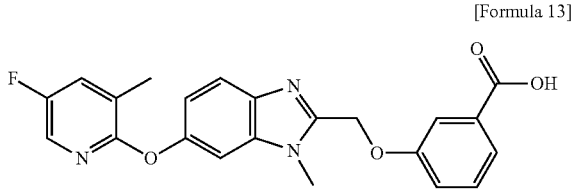 [SMILES: Cc1cc(F)cnc1Oc1ccc2nc(COc3cccc(C(=O)O)c3)n(C)c2c1]

[Formula 13]

(8a) 3-Bromo-2,5-difluoropyridine

Sodium nitrite (1.97 g, 28.6 mmol) was added in small portions to a solution of 3-bromo-5-fluoropyridin-2-amine (WO200625783 A1, 3.64 g, 19.1 mmol) in hydrogen fluoride-pyridine (10 mL) at −10° C. After stirring at room temperature for two hours, water (100 mL) and sodium bicarbonate were added to the reaction mixture at 0° C., followed by extraction with ethyl acetate (100 mL). Then, the organic layer was washed with water (100 mL) twice and dried over anhydrous sodium sulfate. After concentration under reduced pressure, the residue was purified by silica gel chromatography (methylene chloride) to obtain the title compound (1.56 g, 42%) as a brown liquid.

$^1$H-NMR (400 MHz, CDCl$_3$): δ ppm: 7.78 (1H, dt, J=2.7, 6.7 Hz), 8.02 (1H, dd, J=1.6, 2.4 Hz).

(8b) Methyl 3-({6-[(3-bromo-5-fluoropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (2.28 g, 7.30 mmol), 3-bromo-2,5-difluoropyridine produced in Example (8a) (1.56 g, 8.03 mmol), copper iodide (0.14 g, 0.73 mmol), 1,10-phenanthroline (0.13 g, 0.73 mmol), cesium carbonate (7.14 g, 21.9 mmol) and DMF (40 mL) to obtain the title compound (1.92 g, 54%) as a white solid.

$^1$H-NMR (500 MHz, DMSO-d$_6$): δ ppm: 3.83 (3H, s), 3.85 (3H, s), 5.50 (2H, s), 7.00 (1H, dd, J=2.4, 8.6 Hz), 7.43 (1H, ddd, J=1.2, 2.4, 8.2 Hz), 7.45-7.50 (2H, m), 7.59 (1H, dt, J=1.2, 7.8 Hz), 7.65-7.67 (2H, m), 8.13 (1H, d, J=2.7 Hz), 8.38 (1H, dd, J=2.7, 7.4 Hz).

(8c) Methyl 3-({6-[(5-fluoro-3-methylpyridin-2-yl)oxy]-1-methyl-1H-benzimidazol-2-yl}methoxy)benzoate The reaction and post-treatment were carried out according to Example (2b) using methyl 3-({6-[(3-bromo-5-fluoropyridin-2-yl)oxy]-1-methyl-1H-benzimidazol-2-yl}methoxy)benzoate produced in Example (8b) (1.92 g, 3.95 mmol), trimethylboroxine (50% solution in THF, 2.23 mL, 7.90 mmol), a [1,1'-bis(diphenylphosphino)-ferrocene]dichloropalladium (II)-dichloromethane mixture (0.32 g, 0.39 mmol), potassium carbonate (1.09 g, 7.90 mmol) and DMF (40 mL) to obtain the title compound (0.99 g, 60%) as a white solid.

$^1$H-NMR (500 MHz, CDCl$_3$): δ ppm: 2.41 (3H, s), 3.85 (3H, s), 3.93 (3H, s), 5.41 (2H, s), 7.03 (1H, dd, J=1.5, 8.8 Hz), 7.13 (1H, d, J=2.0 Hz), 7.30 (1H, dd, J=2.9, 8.3 Hz), 7.34 (1H, dd, J=1.5, 7.3 Hz), 7.37 (1H, t, J=8.3 Hz), 7.69 (1H, d, J=7.3 Hz), 7.73 (1H, s), 7.77 (1H, d, J=8.8 Hz), 7.81 (1H, d, J=2.9 Hz).

(8d) 3-({6-[(5-Fluoro-3-methylpyridin-2-yl)oxy]-1-methyl-1H-benzimidazol-2-yl}methoxy)benzoic acid The reaction and post-treatment were carried out according to Example (1g) using methyl 3-({6-[(5-fluoro-3-methylpyridin-2-yl)oxy]-1-methyl-1H-benzimidazol-2-yl}methoxy)benzoate produced in Example (8c) (0.99 g, 2.35 mmol), a 1 M sodium hydroxide aqueous solution (10 mL), 1,4-dioxane (10 mL) and methanol (10 mL) to obtain the title compound (0.91 g, 95%) as a white solid.

$^1$H-NMR (400 MHz, DMSO-d$_6$): δ ppm: 2.35 (3H, s), 3.81 (3H, s), 5.47 (2H, s), 6.95 (1H, dd, J=2.4, 8.6 Hz), 7.36-7.38 (2H, m), 7.44 (1H, t, J=7.4 Hz), 7.57 (1H, d, J=7.4 Hz), 7.62-7.64 (2H, m), 7.75 (1H, dd, J=2.7, 8.6 Hz), 7.89 (1H, dd, J=0.8, 2.7 Hz), 13.04 (1H, brs);

Anal. Calcd for C$_{22}$H$_{18}$FN$_3$O$_4$.0.5H$_2$O: C, 63.46; H, 4.60; N, 10.09. Found C, 63.74; H, 4.26; N, 10.26.

Example 9

3-({6-[(3-Fluoro-5-methylpyridin-2-yl)oxy]-1-methyl-1H-benzimidazol-2-yl}methoxy)benzoic acid

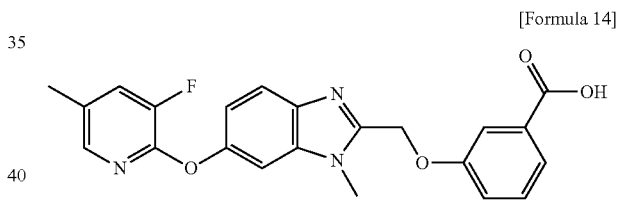

[Formula 14]

(9a) 5-Bromo-2,3-difluoropyridine

The reaction and post-treatment were carried out according to Example (8a) using 5-bromo-3-fluoropyridin-2-amine (WO200784786 A1) (8.42 g, 44.1 mmol), sodium nitrite (4.56 g, 66.1 mmol) and hydrogen fluoride-pyridine (15 mL) to obtain the title compound (8.55 g, 91%) as a colorless liquid.

$^1$H-NMR (500 MHz, CDCl$_3$): δ ppm: 7.74 (1H, dt, J=2.0, 8.3 Hz), 8.08 (1H, t, J=2.0 Hz).

(9b) Methyl 3-({6-[(5-bromo-3-fluoropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (4.06 g, 13.0 mmol), 5-Bromo-2,3-difluoropyridine produced in Example (9a) (2.77 g, 14.3 mmol), copper iodide (0.25 g, 1.30 mmol), 1,10-phenanthroline (0.23 g, 1.30 mmol), cesium carbonate (12.71 g, 39.0 mmol) and DMF (65 mL) to obtain the title compound (4.14 g, 66%) as a white solid.

¹H-NMR (500 MHz, CDCl₃): δ ppm: 3.87 (3H, s), 3.93 (3H, s), 5.41 (2H, brs), 7.10 (1H, brs), 7.23 (1H, brs), 7.31 (1H, d, J=8.3 Hz), 7.38 (1H, t, J=7.8 Hz), 7.67 (1H, dd, J=2.0, 8.8 Hz), 7.70 (1H, d, J=7.8 Hz), 7.73 (1H, s), 7.80 (1H, brs), 7.96 (1H, d, J=2.0 Hz).

(9c) Methyl 3-({6-[(3-fluoro-5-methylpyridin-2-yl)oxy]-1-methyl-1H-benzimidazol-2-yl}methoxy)benzoate The reaction and post-treatment were carried out according to Example (2b) using methyl 3-({6-[(5-bromo-3-fluoropyridin-2-yl)oxy]-1-methyl-1H-benzimidazol-2-yl}methoxy)benzoate produced in Example (9b) (4.14 g, 8.51 mmol), trimethylboroxine (50% solution in THF, 4.80 mL, 17.0 mmol), a [1,1'-bis(diphenylphosphino)-ferrocene]dichloropalladium(II)-dichloromethane mixture (0.70 g, 0.85 mmol), potassium carbonate (2.35 g, 17.0 mmol) and DMF (80 mL) to obtain the title compound (2.02 g, 56%) as a white solid.

¹H-NMR (500 MHz, CDCl₃): δ ppm: 2.31 (3H, s), 3.86 (3H, s), 3.93 (3H, s), 5.42 (2H, s), 7.09 (1H, dd, J=2.0, 8.8 Hz), 7.19 (1H, d, J=2.0 Hz), 7.30 (1H, ddd, J=1.0, 2.9, 8.3 Hz), 7.32-7.35 (1H, m), 7.38 (1H, t, J=7.8 Hz), 7.69 (1H, dt, J=1.5, 7.3 Hz), 7.72-7.73 (2H, m), 7.78 (1H, d, J=8.8 Hz).

(9d) 3-({6-[(3-Fluoro-5-methylpyridin-2-yl)oxy]-1-methyl-1H-benzimidazol-2-yl}methoxy)benzoic acid The reaction and post-treatment were carried out according to Example (1g) using methyl 3-({6-[(3-fluoro-5-methylpyridin-2-yl)oxy]-1-methyl-1H-benzimidazol-2-yl}methoxy)benzoate produced in Example (9c) (2.02 g, 4.79 mmol), a 1 M sodium hydroxide aqueous solution (25 mL) and methanol (50 mL) to obtain the title compound (1.98 g, 98%) as a white solid.

¹H-NMR (500 MHz, DMSO-d₆): δ ppm: 2.27 (3H, s), 3.82 (3H, s), 5.47 (2H, s), 7.00 (1H, dd, J=2.4, 8.8 Hz), 7.38 (1H, dd, J=1.5, 7.8 Hz), 7.42 (1H, d, J=2.4 Hz), 7.44 (1H, t, J=8.3 Hz), 7.56 (1H, dt, J=1.5, 7.3 Hz), 7.63-7.65 (2H, m), 7.73 (1H, dd, J=1.5, 11.2 Hz), 7.75 (1H, s), 13.01 (1H, brs).

Example 10

3-({6-[(3,5-Dimethylpyridin-2-yl)oxy]-1-methyl-1H-benzimidazol-2-yl}methoxy)benzoic acid

[Formula 15]

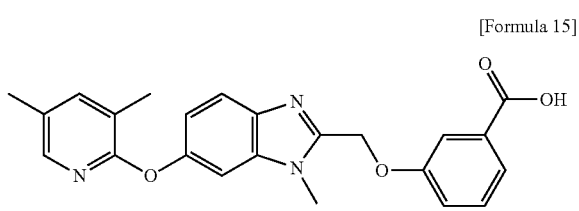 [SMILES: Cc1cnc(Oc2ccc3nc(COc4cccc(C(=O)O)c4)n(C)c3c2)c(C)c1]

(10a) Methyl 3-({6-[(3,5-dibromopyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (2.50 g, 8.00 mmol), 3,5-dibromo-2-fluoropyridine (2.24 g, 8.81 mmol), copper iodide (0.15 g, 0.80 mmol), 1,10-phenanthroline (0.14 g, 0.80 mmol), cesium carbonate (7.82 g, 24.0 mmol) and DMF (40 mL) to obtain the title compound (3.24 g, 74%) as a white solid.

¹H-NMR (400 MHz, DMSO-d₆): δ ppm: 3.83 (3H, s), 3.85 (3H, s), 5.50 (2H, s), 7.02 (1H, dd, J=2.4, 8.6 Hz), 7.43 (1H, ddd, J=1.2, 2.7, 8.2 Hz), 7.46-7.50 (2H, m), 7.59 (1H, dt, J=1.6, 7.4 Hz), 7.66-7.68 (2H, m), 8.20 (1H, d, J=2.0 Hz), 8.52 (1H, d, J=2.4 Hz).

(10b) Methyl 3-({6-[(3,5-dimethylpyridin-2-yl)oxy]-1-methyl-1H-benzimidazol-2-yl}methoxy)benzoate The reaction and post-treatment were carried out according to Example (2b) using methyl 3-({6-[(3,5-dibromopyridin-2-yl)oxy]-1-methyl-1H-benzimidazol-2-yl}methoxy)benzoate produced in Example (10a) (5.47 g, 10.0 mmol), trimethylboroxine (50% solution in THF, 11.28 mL, 40.0 mmol), a [1,1'-bis(diphenylphosphino)-ferrocene]dichloropalladium(II)-dichloromethane mixture (0.82 g, 1.00 mmol), potassium carbonate (5.53 g, 40.0 mmol) and DMF (100 mL) to obtain the title compound (3.80 g, 91%) as a white solid.

¹H-NMR (400 MHz, CDCl₃): δ ppm: 2.25 (3H, s), 2.36 (3H, s), 3.84 (3H, s), 3.93 (3H, s), 5.41 (2H, s), 7.02 (1H, dd, J=2.0, 8.6 Hz), 7.12 (1H, d, J=2.0 Hz), 7.28-7.31 (1H, m), 7.35-7.39 (2H, m), 7.69 (1H, dt, J=1.2, 7.4 Hz), 7.72-7.79 (3H, m).

(10c) 3-({6-[(3,5-Dimethylpyridin-2-yl)oxy]-1-methyl-1H-benzimidazol-2-yl}methoxy)benzoic acid The reaction and post-treatment were carried out according to Example (1g) using methyl 3-({6-[(3,5-dimethylpyridin-2-yl)oxy]-1-methyl-1H-benzimidazol-2-yl}methoxy)benzoate produced in Example (10b) (0.96 g, 2.30 mmol), a 1 M sodium hydroxide aqueous solution (50 mL) and methanol (50 mL) to obtain the title compound (0.85 g, 92%) as a white solid.

¹H-NMR (400 MHz, DMSO-d₆): δ ppm: 2.20 (3H, s), 2.30 (3H, s), 3.81 (3H, s), 5.47 (2H, s), 6.92 (1H, dd, J=2.4, 8.6 Hz), 7.32 (1H, d, J=2.4 Hz), 7.36 (1H, dd, J=1.6, 7.4 Hz), 7.44 (1H, t, J=7.4 Hz), 7.54-7.63 (4H, m), 7.72 (1H, s), 13.04 (1H, brs);

Anal. Calcd for C₂₃H₂₁N₃O₄: C, 68.47; H, 5.25; N, 10.42. Found C, 68.29; H, 5.17; N, 10.41.

Example 11

3-({6-[(5-Ethyl-3-methylpyridin-2-yl)oxy]-1-methyl-1H-benzimidazol-2-yl}methoxy)benzoic acid

[Formula 16]

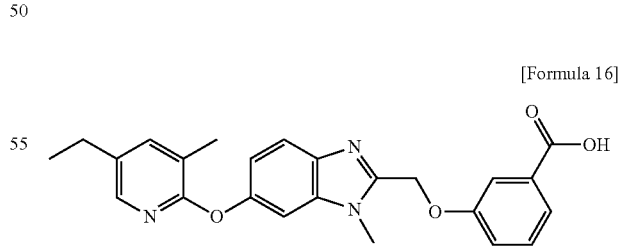

(11a) Methyl 3-({6-[(5-bromo-3-methylpyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (3.12 g, 10.0 mmol), 5-bromo-2-fluoro-3-methylpyridine (2.09 g, 11.0 mmol), copper iodide (0.19 g, 1.00 mmol), 1,10-phenanthroline (0.18 g, 1.00 mmol), cesium carbonate (9.77 g, 30.0 mmol) and DMF (50 mL) to obtain the title compound (0.65 g, 14%) as a white solid.

$^1$H-NMR (500 MHz, CDCl$_3$): δ ppm: 2.39 (3H, s), 3.86 (3H, s), 3.93 (3H, s), 5.42 (2H, s), 7.03 (1H, dd, J=2.4, 8.8 Hz), 7.15 (1H, d, J=2.0 Hz), 7.31 (1H, dd, J=2.0, 7.3 Hz), 7.38 (1H, t, J=7.8 Hz), 7.66-7.67 (1H, m), 7.70 (1H, d, J=7.8 Hz), 7.73 (1H, t, J=2.0 Hz), 7.78 (1H, d, J=8.8 Hz), 8.00 (1H, d, J=2.0 Hz).

(11b) Methyl 3-({6-[(5-ethyl-3-methylpyridin-2-yl)oxy]-1-methyl-1H-benzimidazol-2-yl}methoxy)benzoate The reaction and post-treatment were carried out according to Example (2b) using methyl 3-({6-[(5-bromo-3-methylpyridin-2-yl)oxy]-1-methyl-1H-benzimidazol-2-yl}methoxy)benzoate produced in Example (11a) (0.65 g, 1.35 mmol), triethylborane (1.0 M solution in THF, 2.70 mL, 2.70 mmol), a [1,1'-bis(diphenylphosphino)-ferrocene]dichloropalladium (II)-dichloromethane mixture (0.11 g, 0.13 mmol), potassium carbonate (0.37 g, 2.70 mmol) and DMF (10 mL) to obtain the title compound (0.58 g, 99%) as a pale yellow oil.

$^1$H-NMR (400 MHz, CDCl$_3$): δ ppm: 1.23 (3H, t, J=8.2 Hz), 2.37 (3H, s), 2.58 (2H, q, J=7.8 Hz), 3.85 (3H, s), 3.93 (3H, s), 5.42 (2H, s), 7.04 (1H, dd, J=2.4, 8.6 Hz), 7.14 (1H, d, J=2.0 Hz), 7.29-7.32 (1H, m), 7.37 (1H, d, J=7.8 Hz), 7.40 (1H, d, J=2.7 Hz), 7.69 (1H, d, J=7.4 Hz), 7.72 (1H, t, J=2.0 Hz), 7.76 (1H, d, J=8.6 Hz), 7.81 (1H, d, J=2.4 Hz).

(11c) 3-({6-[(5-Ethyl-3-methylpyridin-2-yl)oxy]-1-methyl-1H-benzimidazol-2-yl}methoxy)benzoic acid The reaction and post-treatment were carried out according to Example (1g) using methyl 3-({6-[(5-ethyl-3-methylpyridin-2-yl)oxy]-1-methyl-1H-benzimidazol-2-yl}methoxy)benzoate produced in Example (11b) (0.58 g, 1.34 mmol), a 1 M sodium hydroxide aqueous solution (5 mL) and methanol (10 mL) to obtain the title compound (0.43 g, 77%) as a white solid.

$^1$H-NMR (400 MHz, DMSO-d$_6$): δ ppm: 1.16 (3H, t, J=7.8 Hz), 2.31 (3H, s), 2.52 (2H, q, J=7.8 Hz), 3.81 (3H, s), 5.47 (2H, s), 6.93 (1H, dd, J=2.0, 8.6 Hz), 7.34 (1H, d, J=2.4 Hz), 7.39 (1H, ddd, J=0.8, 2.4, 8.2 Hz), 7.45 (1H, t, J=7.4 Hz), 7.56-7.58 (2H, m), 7.61 (1H, d, J=9.0 Hz), 7.64 (1H, dd, J=1.6, 2.7 Hz), 7.73 (1H, d, J=2.4 Hz), 12.98 (1H, s).

Example 12

3-({6-[(3-Ethyl-5-methylpyridin-2-yl)oxy]-1-methyl-1H-benzimidazol-2-yl}methoxy)benzoic acid

[Formula 17]

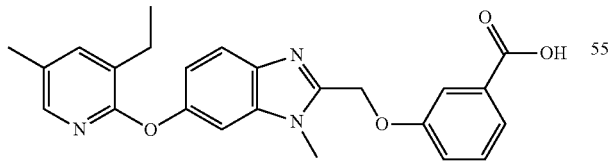

(12a) Methyl 3-({6-[(3-bromo-5-methylpyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (3.12 g, 10.0 mmol), 3-bromo-2-fluoro-5-methylpyridine (2.09 g, 11.0 mmol), copper iodide (0.19 g, 1.00 mmol), 1,10-phenanthroline (0.18 g, 1.00 mmol), cesium carbonate (9.77 g, 30.0 mmol) and DMF (50 mL) to obtain the title compound (0.65 g, 14%) as a white solid.

$^1$H-NMR (500 MHz, CDCl$_3$): δ ppm: 2.28 (3H, s), 3.86 (3H, s), 3.93 (3H, s), 5.42 (2H, s), 7.08 (1H, dd, J=2.4, 8.8 Hz), 7.19 (1H, d, J=2.0 Hz), 7.31 (1H, dd, J=2.9, 8.3 Hz), 7.38 (1H, t, J=8.3 Hz), 7.70 (1H, d, J=7.8 Hz), 7.73 (1H, s), 7.77-7.80 (2H, m), 7.87 (1H, s).

(12b) Methyl 3-({6-[(3-ethyl-5-methylpyridin-2-yl)oxy]-1-methyl-1H-benzimidazol-2-yl}methoxy)benzoate The reaction and post-treatment were carried out according to Example (2b) using methyl 3-({6-[(3-bromo-5-methylpyridin-2-yl)oxy]-1-methyl-1H-benzimidazol-2-yl}methoxy)benzoate produced in Example (12a) (0.65 g, 1.35 mmol), triethylborane (1.0 M solution in THF, 2.70 mL, 2.70 mmol), a [1,1'-bis(diphenylphosphino)-ferrocene]dichloropalladium (II)-dichloromethane mixture (0.11 g, 0.13 mmol), potassium carbonate (0.37 g, 2.70 mmol) and DMF (10 mL) to obtain the title compound (0.23 g, 40%) as a white solid.

$^1$H-NMR (500 MHz, CDCl$_3$): δ ppm: 1.31 (3H, t, J=6.4 Hz), 2.27 (3H, s), 2.76 (2H, q, J=7.3 Hz), 3.84 (3H, s), 3.93 (3H, s), 5.42 (2H, s), 7.03 (1H, dd, J=2.4, 7.8 Hz), 7.12 (1H, s), 7.29-7.31 (1H, m), 7.37 (1H, d, J=7.8 Hz), 7.39 (1H, s), 7.69 (1H, d, J=7.8 Hz), 7.72 (1H, t, J=1.5 Hz), 7.76 (1H, d, J=8.8 Hz), 7.80 (1H, s).

(12c) 3-({6-[(3-Ethyl-5-methylpyridin-2-yl)oxy]-1-methyl-1H-benzimidazol-2-yl}methoxy)benzoic acid The reaction and post-treatment were carried out according to Example (1g) using methyl 3-({6-[(3-ethyl-5-methylpyridin-2-yl)oxy]-1-methyl-1H-benzimidazol-2-yl}methoxy)benzoate produced in Example (12b) (0.23 g, 0.53 mmol), a 1 M sodium hydroxide aqueous solution (5 mL) and methanol (10 mL) to obtain the title compound (0.15 g, 68%) as a white solid.

$^1$H-NMR (500 MHz, DMSO-d$_6$): δ ppm: 1.25 (3H, t, J=7.8 Hz), 2.22 (3H, s), 2.69 (2H, q, J=7.3 Hz), 3.82 (3H, s), 5.48 (2H, s), 6.92 (1H, dd, J=2.4, 8.8 Hz), 7.33 (1H, d, J=2.0 Hz), 7.39 (1H, dd, J=2.4, 8.3 Hz), 7.45 (1H, t, J=7.8 Hz), 7.55 (1H, d, J=2.4 Hz), 7.58 (1H, d, J=7.3 Hz), 7.62 (1H, d, J=8.3 Hz), 7.64 (1H, dd, J=1.5, 2.9 Hz), 7.73 (1H, d, J=2.0 Hz), 13.02 (1H, s).

Example 13

3-({6-[(3,6-Difluoropyridin-2-yl)oxy]-1-methyl-1H-benzimidazol-2-yl}methoxy)benzoic acid

[Formula 18]

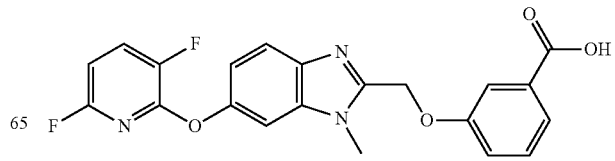

(13a) Methyl 3-({6-[(3,6-difluoropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (3.12 g, 10.0 mmol), 2,3,6-trifluoropyridine (1.46 g, 11.0 mmol), copper iodide (0.19 g, 1.00 mmol), 1,10-phenanthroline (0.18 g, 1.00 mmol), cesium carbonate (9.77 g, 30.0 mmol) and DMF (50 mL) to obtain the title compound (3.02 g, 71%) as a white solid.
$^1$H-NMR (400 MHz, CDCl$_3$): δ ppm: 3.88 (3H, s), 3.93 (3H, s), 5.42 (2H, s), 6.58 (1H, ddd, J=2.4, 3.5, 8.6 Hz), 7.11 (1H, dd, J=2.0, 8.6 Hz), 7.22 (1H, d, J=2.4 Hz), 7.31 (1H, ddd, J=0.8, 2.7, 8.2 Hz), 7.39 (1H, t, J=7.8 Hz), 7.59 (1H, dt, J=5.9, 8.2 Hz), 7.70 (1H, dt, J=1.2, 7.8 Hz), 7.73 (1H, dd, J=1.6, 2.4 Hz), 7.79 (1H, d, J=8.6 Hz).

(13b) 3-({6-[(3,6-Difluoropyridin-2-yl)oxy]-1-methyl-1H-benzimidazol-2-yl}methoxy)benzoic acid The reaction and post-treatment were carried out according to Example (1g) using methyl 3-({6-[(3,6-difluoropyridin-2-yl)oxy]-1-methyl-1H-benzimidazol-2-yl}methoxy)benzoate produced in Example (13a) (3.02 g, 7.10 mmol), a 2 M sodium hydroxide aqueous solution (10 mL) and 1,4-dioxane (20 mL) to obtain the title compound (2.52 g, 86%) as a white solid.
$^1$H-NMR (400 MHz, DMSO-d$_6$): δ ppm: 3.84 (3H, s), 5.48 (2H, s), 6.93 (1H, dt, J=2.0, 8.6 Hz), 7.08 (1H, dd, J=2.0, 8.6 Hz), 7.38 (1H, dd, J=1.6, 8.2 Hz), 7.45 (1H, t, J=7.4 Hz), 7.55 (1H, d, J=2.4 Hz), 7.57 (1H, d, J=7.8 Hz), 7.64 (1H, s), 7.69 (1H, d, J=8.6 Hz), 8.09 (1H, dt, J=6.3, 8.6 Hz), 13.08 (1H, brs).

Example 14

3-({6-[(4-Methoxy-3,5-dimethylpyridin-2-yl)oxy]-1-methyl-1H-benzimidazol-2-yl}methoxy)benzoic acid

[Formula 19]

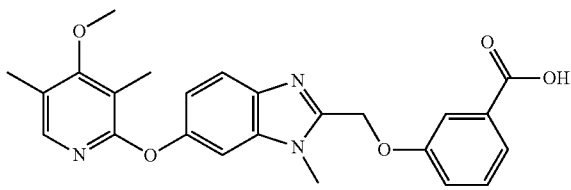

(14a) 3,5-Dibromo-4-chloropyridin-2-amine

A solution of 4-chloropyridin-2-amine (8.16 g, 63.5 mmol) and N-bromosuccinimide (23.7 g, 133 mmol) in dichloromethane (200 mL) was stirred at room temperature for one hour. The insoluble matter was separated by filtration and the filtrate was concentrated under reduced pressure. Then, the residue was purified by silica gel chromatography (methylene chloride/ethyl acetate, 1:1) to obtain the title compound (18.2 g, 56%) as a white solid.
$^1$H-NMR (400 MHz, CDCl$_3$): δ ppm: 5.08 (2H, brs), 8.13 (1H, s).

(14b) 3,5-Dibromo-4-chloro-2-fluoropyridine

The reaction and post-treatment were carried out according to Example (8a) using 3,5-dibromo-4-chloropyridin-2-amine produced in Example (14a) (10.1 g, 35.4 mmol), sodium nitrite (3.66 g, 53.1 mmol) and hydrogen fluoride-pyridine (50 mL) to obtain the title compound (8.50 g, 83%) as a pale yellow oil.
$^1$H-NMR (400 MHz, CDCl$_3$): δ ppm: 8.32 (1H, s).

(14c) Methyl 3-({6-[(3,5-dibromo-4-chloropyridin-2-yl)oxy]-1-methyl-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (1.69 g, 5.00 mmol), 3,5-dibromo-4-chloro-2-fluoropyridine produced in Example (14b) (1.59 g, 5.50 mmol), copper iodide (0.10 g, 0.50 mmol), 1,10-phenanthroline (0.09 g, 0.50 mmol), cesium carbonate (4.89 g, 15.0 mmol) and DMF (30 mL) to obtain the title compound (1.56 g, 54%) as a white solid.
$^1$H-NMR (500 MHz, CDCl$_3$): δ ppm: 3.87 (3H, s), 3.93 (3H, s), 5.42 (2H, s), 7.05-7.07 (1H, m), 7.18 (1H, d, J=2.0 Hz), 7.28-7.31 (1H, m), 7.38 (1H, t, J=7.8 Hz), 7.70 (1H, d, J=7.8 Hz), 7.72-7.74 (1H, m), 7.81 (1H, d, J=8.8 Hz), 8.16 (1H, s).

(14d) Methyl 3-({6-[(3,5-dibromo-4-methoxypyridin-2-yl)oxy]-1-methyl-1H-benzimidazol-2-yl}methoxy)benzoate The reaction and post-treatment were carried out according to Example (3b) using methyl 3-({6-[(3,5-dibromo-4-chloropyridin-2-yl)oxy]-1-methyl-1H-benzimidazol-2-yl}methoxy)benzoate produced in Example (14c) (1.56 g, 2.68 mmol), sodium methoxide (5.0 M solution in methanol, 5.36 mL, 26.8 mmol), water (5 mL) and methanol (100 mL) to obtain the title compound (0.13 g, 8%) as a white solid.
$^1$H-NMR (400 MHz, CDCl$_3$): δ ppm: 3.87 (3H, s), 3.93 (3H, s), 4.05 (3H, s), 5.42 (2H, s), 7.07 (1H, dd, J=2.0, 8.6 Hz), 7.18 (1H, d, J=2.4 Hz), 7.28-7.31 (1H, m), 7.38 (1H, t, J=7.8 Hz), 7.69 (1H, d, J=7.8 Hz), 7.72-7.73 (1H, m), 7.80 (1H, d, J=8.6 Hz), 8.09 (1H, s).

(14e) Methyl 3-({6-[(4-methoxy-3,5-dimethylpyridin-2-yl)oxy]-1-methyl-1H-benzimidazol-2-yl}methoxy)benzoate The reaction and post-treatment were carried out according to Example (2b) using methyl 3-({6-[(3,5-dibromo-4-methoxypyridin-2-yl)oxy]-1-methyl-1H-benzimidazol-2-yl}methoxy)benzoate produced in Example (14d) (0.13 g, 0.23 mmol), trimethyl boroxine (50% solution in THF, 0.25 mL, 0.90 mmol), a [1,1'-bis(diphenylphosphino)-ferrocene]dichloropalladium (II)-dichloromethane mixture (0.02 g, 0.02 mmol), potassium carbonate (0.12 g, 0.90 mmol) and DMF (10 mL) to obtain the title compound (57 mg, 57%) as a white solid.
$^1$H-NMR (500 MHz, CDCl$_3$): δ ppm: 2.20 (3H, s), 2.31 (3H, s), 3.84 (3H, s), 3.84 (3H, s), 3.93 (3H, s), 5.42 (2H, s), 7.03 (1H, dd, J=2.0, 8.8 Hz), 7.13 (1H, d, J=2.4 Hz), 7.28-7.31 (1H, m), 7.37 (1H, t, J=7.8 Hz), 7.69 (1H, dt, J=1.0, 7.3 Hz), 7.72 (1H, dd, J=1.5, 2.4 Hz), 7.76 (1H, d, J=8.8 Hz), 7.78 (1H, s).

(14f) 3-({6-[(4-Methoxy-3,5-dimethylpyridin-2-yl)oxy]-1-methyl-1H-benzimidazol-2-yl}methoxy)benzoic acid The reaction and post-treatment were carried out according to Example (1g) using methyl 3-({6-[(4-methoxy-3,5-dimethylpyridin-2-yl)oxy]-1-methyl-1H-benzimidazol-2-yl}methoxy)benzoate produced in Example (14e) (57 mg, 0.13 mmol), a 1 M sodium hydroxide aqueous solution (2 mL) and methanol (2 mL) to obtain the title compound (37 mg, 67%) as a white solid.

$^1$H-NMR (400 MHz, DMSO-$d_6$): δ ppm: 2.14 (3H, s), 2.23 (3H, s), 3.79 (3H, s), 3.81 (3H, s), 5.47 (2H, s), 6.92 (1H, dd, J=0.8, 8.6 Hz), 7.33 (1H, d, J=2.4 Hz), 7.38 (1H, d, J=8.2 Hz), 7.44 (1H, t, J=7.4 Hz), 7.57 (1H, d, J=7.8 Hz), 7.61 (1H, d, J=8.6 Hz), 7.63 (1H, s), 7.73 (1H, d, J=0.8 Hz), 13.05 (1H, brs).

Example 15

3-({1-Methyl-6-[(3,5,6-trimethylpyridin-2-yl)oxy]-1H-benzimidazol-2-yl}methoxy)benzoic acid

[Formula 20]

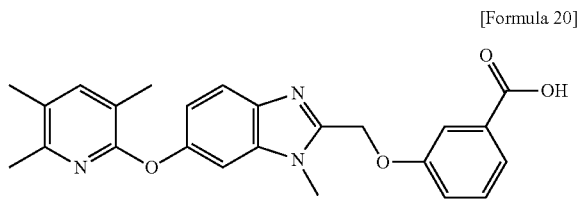

(15a) 3,5,6-Tribromopyridin-2-amine

The reaction and post-treatment were carried out according to Example (14a) using 6-bromopyridin-2-amine (1.73 g, 10.0 mmol), N-bromosuccinimide (3.74 g, 21.0 mmol) and dichloromethane (50 mL) to obtain the title compound (2.34 g, 71%) as a pale brown solid.

$^1$H-NMR (400 MHz, CDCl$_3$): δ ppm: 5.06 (2H, brs), 7.79 (1H, s).

(15b) 2,3,5-Tribromo-6-fluoropyridine

The reaction and post-treatment were carried out according to Example (8a) using 3,5,6-tribromopyridin-2-amine produced in Example (15a) (2.34 g, 7.07 mmol), sodium nitrite (0.73 g, 10.6 mmol) and hydrogen fluoride-pyridine (5 mL) to obtain the title compound (1.98 g, 84%) as a pale yellow oil.

$^1$H-NMR (400 MHz, CDCl$_3$): δ ppm: 8.15 (1H, d, J=7.4 Hz). (15c) Methyl 3-({1-methyl-6-[(3,5,6-tribromopyridin-2-yl)oxy]-1H-benzimidazol-2-yl}methoxy)benzoate The reaction and post-treatment were carried out according to Example (1f) using methyl 3-[(6-hydroxy-1-methyl-1H-benzimidazol-2-yl)methoxy]benzoate produced in Example (1e) (1.69 g, 5.40 mmol), 2,3,5-tribromo-6-fluoropyridine produced in Example (15b) (1.98 g, 5.94 mmol), copper iodide (0.10 g, 0.54 mmol), 1,10-phenanthroline (0.10 g, 0.54 mmol), cesium carbonate (5.28 g, 16.2 mmol) and DMF (30 mL) to obtain the title compound (2.92 g, 86%) as a white solid.

$^1$H-NMR (400 MHz, CDCl$_3$): δ ppm: 3.88 (3H, s), 3.93 (3H, s), 5.43 (2H, s), 7.08 (1H, dd, J=2.4, 9.0 Hz), 7.21 (1H, d, J=2.0 Hz), 7.29-7.32 (1H, m), 7.39 (1H, t, J=7.8 Hz), 7.70 (1H, dt, J=1.6, 6.3 Hz), 7.74 (1H, dd, J=1.6, 2.4 Hz), 7.79 (1H, d, J=9.0 Hz), 8.10 (1H, s). (15d) Methyl 3-({1-methyl-6-[(3,5,6-trimethylpyridin-2-yl)oxy]-1H-benzimidazol-2-yl}methoxy)benzoate The reaction and post-treatment were carried out according to Example (2b) using methyl 3-({1-methyl-6-[(3,5,6-tribromopyridin-2-yl)oxy]-1H-benzimidazol-2-yl}methoxy)benzoate produced in Example (15c) (2.92 g, 4.66 mmol), trimethylboroxine (50% solution in THF, 3.89 mL, 14.0 mmol), a [1,1'-bis(diphenylphosphino)-ferrocene]dichloropalladium (II)-dichloromethane mixture (0.38 g, 0.47 mmol), potassium carbonate (1.93 g, 14.0 mmol) and DMF (50 mL) to obtain the title compound (1.30 g, 65%) as a white solid.

$^1$H-NMR (400 MHz, CDCl$_3$): δ ppm: 2.22 (3H, s), 2.25 (3H, s), 2.30 (3H, s), 3.82 (3H, s), 3.93 (3H, s), 5.40 (2H, s), 6.99 (1H, dd, J=2.4, 9.0 Hz), 7.04 (1H, d, J=2.4 Hz), 7.29-7.31 (2H, m), 7.38 (1H, t, J=7.4 Hz), 7.69 (1H, dt, J=1.2, 7.8 Hz), 7.70 (1H, d, J=8.6 Hz), 7.73 (1H, dd, J=1.6, 2.7 Hz).

(15e) 3-({1-Methyl-6-[(3,5,6-trimethylpyridin-2-yl)oxy]-1H-benzimidazol-2-yl}methoxy)benzoic acid The reaction and post-treatment were carried out according to Example (1g) using methyl 3-({1-methyl-6-[(3,5,6-trimethylpyridin-2-yl)oxy]-1H-benzimidazol-2-yl}methoxy)benzoate produced in Example (15d) (1.30 g, 3.01 mmol), a 1 M sodium hydroxide aqueous solution (100 mL), 1,4-dioxane (100 mL) and methanol (100 mL) to obtain the title compound (1.13 g, 93%) as a white solid.

$^1$H-NMR (400 MHz, DMSO-$d_6$): δ ppm: 2.15 (3H, s), 2.16 (3H, s), 2.23 (3H, s), 3.80 (3H, s), 5.45 (2H, s), 6.88 (1H, dd, J=2.4, 8.6 Hz), 7.27 (1H, d, J=2.4 Hz), 7.38 (1H, ddd, J=1.2, 2.7, 8.2 Hz), 7.74 (1H, s), 7.74 (1H, t, J=7.8 Hz), 7.57 (1H, d, J=7.4 Hz), 7.60 (1H, d, J=9.0 Hz), 7.63 (1H, dd, J=1.6, 2.4 Hz), 13.03 (1H, brs);

Anal. Calcd for C$_{24}$H$_{23}$N$_3$O$_4$.0.25H$_2$O: C, 68.31; H, 5.61; N, 9.96. Found C, 68.58; H, 5.49; N, 9.95.

Example 16

3-({6-[(2-Methoxypyridin-4-yl)oxy]-1-methyl-1H-benzimidazol-2-yl}methoxy)benzoic acid

[Formula 21]

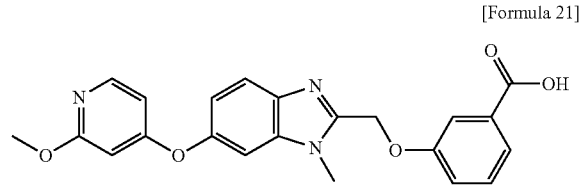 [SMILES: COc1cc(Oc2ccc3nc(COc4cccc(C(=O)O)c4)n(C)c3c2)ccn1]

(16a) 4-(Benzyloxy)-2-methoxypyridine

A solution of 4-(benzyloxy)pyridin-2(1H)-one (9.92 g, 49.3 mmol), methyl iodide (4.60 mL, 74.0 mmol) and silver carbonate (13.6 g, 49.3 mmol) in chloroform (50 mL) was stirred with heating under reflux for four hours. After leaving to cool, the insoluble matter was separated by filtration and the filtrate was concentrated under reduced pressure. Then, the residue was purified by silica gel chromatography (hexane/ethyl acetate, 2:1) to obtain the title compound (4.65 g, 44%) as a pale yellow oil.

$^1$H-NMR (500 MHz, CDCl$_3$): δ ppm: 3.92 (3H, s), 5.08 (2H, s), 6.28 (1H, d, J=2.0 Hz), 6.56 (1H, dd, J=2.4, 5.9 Hz), 7.34-7.43 (5H, m), 7.99 (1H, d, J=5.9 Hz).

(16b) 2-Methoxypyridin-4-ol

A solution of 4-(benzyloxy)-2-methoxypyridine produced in Example (16a) (4.65 g, 21.6 mmol) and 10% palladium carbon (2.30 g, 2.16 mmol) in ethanol (100 mL) was stirred in a hydrogen atmosphere at room temperature for 30 minutes. The insoluble matter was separated by filtration and then the filtrate was concentrated to obtain the title compound (2.70 g, 99%) as a colorless oil.

$^1$H-NMR (400 MHz, CDCl$_3$): δ ppm: 3.90 (3H, s), 6.13 (1H, s), 6.42 (1H, d, J=5.9 Hz), 7.80 (1H, brs).

(16c) 5-[(2-Methoxypyridin-4-yl)oxy]-N-methyl-2-nitroaniline

A solution of 5-fluoro-N-methyl-2-nitroaniline (US2003-675927, 3.30 g, 19.4 mmol), 2-methoxypyridin-4-ol (2.70 g, 21.6 mmol) produced in Example (16b) and cesium carbonate (10.6 g, 32.4 mmol) in DMF (20 mL) was stirred at 80° C. for two hours. After leaving to cool, water (100 mL) was added to the reaction mixture, followed by extraction with ethyl acetate (100 mL). The organic layer was washed with water (100 mL) twice and dried over anhydrous sodium sulfate. After concentration under reduced pressure, the residue was purified by silica gel chromatography (hexane/ethyl acetate, 2:1) to obtain the title compound (3.90 g, 66%) as a yellow solid.

$^1$H-NMR (400 MHz, CDCl$_3$): δ ppm: 2.98 (3H, d, J=5.1 Hz), 3.95 (3H, s), 6.34 (1H, dd, J=2.4, 9.4 Hz), 6.36 (1H, d, J=2.4 Hz), 6.46 (1H, d, J=2.4 Hz), 6.62 (1H, dd, J=2.4, 5.9 Hz), 8.13 (1H, d, J=5.9 Hz), 8.19 (1H, brs), 8.23 (1H, d, J=9.4 Hz).

(16d) 4-[(2-Methoxypyridin-4-yl)oxy]-N$^2$-methyl-benzene-1,2-diamine

The reaction and post-treatment were carried out according to Example (1b) using 5-[(2-methoxypyridin-4-yl)oxy]-N-methyl-2-nitroaniline produced in Example (16c) (3.90 g, 14.2 mmol), iron powder (3.96 g, 70.8 mmol), ammonium chloride (0.38 g, 7.08 mmol), ethanol (80 mL) and water (40 mL) to obtain the title compound (3.46 g, 99%) as a brown oil.

$^1$H-NMR (500 MHz, CDCl$_3$): δ ppm: 2.83 (3H, s), 3.23 (2H, brs), 3.64 (1H, brs), 3.90 (3H, s), 6.19 (1H, d, J=2.0 Hz), 6.37 (1H, s), 6.37-6.39 (1H, m), 6.54 (1H, dd, J=2.0, 5.9 Hz), 6.71 (1H, d, J=7.8 Hz), 8.00 (1H, d, J=6.0 Hz).

(16e) Methyl 3-[2-({4-[(2-methoxypyridin-4-yl)oxy]-2-(methylamino)phenyl}amino)-2-oxoethoxy]benzoate Pivaloyl chloride (1.74 mL, 14.2 mmol) was added dropwise to a solution of [3-(methoxycarbonyl)phenoxy]acetic acid produced in Example (1c) (3.27 g, 15.6 mmol) and triethylamine (1.97 mL, 14.2 mmol) in dichloromethane (40 mL) in a nitrogen atmosphere at 0° C. After one hour, a solution of 4-[(2-methoxypyridin-4-yl)oxy]-N$^2$-methylbenzene-1,2-diamine produced in Example (16d) (3.46 g, 14.2 mmol) and triethylamine (1.97 mL, 14.2 mmol) in dichloromethane (40 mL) was added dropwise at 0° C., and the mixture was stirred at room temperature for two hours. The reaction mixture was concentrated under reduced pressure. Then, the residue was purified by silica gel chromatography (ethyl acetate) to obtain the title compound (4.81 g, 78%) as a pale brown oil.

$^1$H-NMR (500 MHz, CDCl$_3$): δ ppm: 2.80 (3H, d, J=3.9 Hz), 3.92 (3H, s), 3.95 (3H, s), 3.99 (1H, brs), 4.76 (2H, s), 6.25 (1H, d, J=2.4 Hz), 6.47 (1H, s), 6.47-6.49 (1H, m), 6.57 (1H, dd, J=2.4, 6.4 Hz), 7.23 (1H, ddd, J=1.0, 2.4, 8.3 Hz), 7.25-7.29 (1H, m), 7.46 (1H, t, J=7.8 Hz), 7.69 (1H, dd, J=1.5, 2.4 Hz), 7.78 (1H, dt, J=1.0, 6.8 Hz), 7.93 (1H, brs), 8.04 (1H, d, J=5.9 Hz).

(16f) Methyl 3-({6-[(2-methoxypyridin-4-yl)oxy]-1-methyl-1H-benzimidazol-2-yl}methoxy)benzoate Methyl 3-[2-({4-[(2-methoxypyridin-4-yl)oxy]-2-(methylamino)phenyl}amino)-2-oxoethoxy]benzoate produced in Example (16e) (4.52 g, 10.3 mmol) and acetic acid (50 mL) was stirred at 80° C. for two hours. The reaction mixture was concentrated and then water (100 mL) and sodium bicarbonate were added, followed by extraction with ethyl acetate (100 mL). The organic layer was washed with a saturated sodium bicarbonate aqueous solution (100 mL) twice and dried over anhydrous sodium sulfate. After concentration under reduced pressure, the residue was purified by silica gel chromatography (hexane/ethyl acetate, 1:1) to obtain the title compound (3.10 g, 72%) as a white solid.

$^1$H-NMR (400 MHz, CDCl$_3$): δ ppm: 3.87 (3H, s), 3.91 (3H, s), 3.93 (3H, s), 5.43 (2H, s), 6.17 (1H, d, J=2.4 Hz), 6.56 (1H, ddd, J=0.8, 2.0, 5.9 Hz), 7.05 (1H, dd, J=1.6, 9.0 Hz), 7.11 (1H, d, J=2.4 Hz), 7.27-7.32 (1H, m), 7.39 (1H, t, J=7.4 Hz), 7.71 (1H, d, J=7.8 Hz), 7.74 (1H, d, J=1.6 Hz), 7.79 (1H, d, J=8.6 Hz), 8.04 (1H, d, J=5.9 Hz).

(16g) 3-({6-[(2-Methoxypyridin-4-yl)oxy]-1-methyl-1H-benzimidazol-2-yl}methoxy)benzoic acid The reaction and post-treatment were carried out according to Example (1g) using methyl 3-({6-[(2-methoxypyridin-4-yl)oxy]-1-methyl-1H-benzimidazol-2-yl}methoxy)benzoate produced in Example (16f) (3.10 g, 7.39 mmol), a 1 M sodium hydroxide aqueous solution (25 mL) and methanol (50 mL) to obtain the title compound (2.65 g, 88%) as a white solid.

$^1$H-NMR (400 MHz, DMSO-d$_6$): δ ppm: 3.81 (3H, s), 3.85 (3H, s), 5.48 (2H, s), 6.18 (1H, s), 6.60 (1H, dd, J=2.4, 6.3 Hz), 7.03 (1H, dd, J=2.0, 8.6 Hz), 7.39 (1H, dd, J=2.0, 8.2 Hz), 7.45 (1H, t, J=7.4 Hz), 7.51 (1H, s), 7.58 (1H, d, J=7.4 Hz), 7.64 (1H, s), 7.72 (1H, d, J=8.6 Hz), 8.05 (1H, d, J=5.9 Hz), 13.09 (1H, brs);

Anal. Calcd for C$_{22}$H$_{19}$N$_3$O$_5$: C, 65.18; H, 4.72; N, 10.37. Found C, 65.37; H, 4.55; N, 10.34.

Example 17

3-({6-[(2-Methoxy-6-methylpyridin-4-yl)oxy]-1-methyl-1H-benzimidazol-2-yl}methoxy)benzoic acid

[Formula 22]

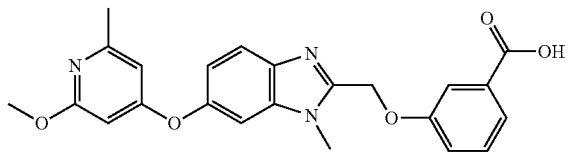

(17a) 6-Methyl-4-[3-(methylamino)-4-nitrophenoxy]pyridin-2-ol

The reaction and post-treatment were carried out according to Example (16c) using 5-fluoro-N-methyl-2-nitroaniline (US2003-675927, 6.30 g, 37.0 mmol), 6-methylpyridine-2, 4-diol (5.09 g, 40.7 mmol), potassium carbonate (5.63 g, 40.7 mmol) and DMF (100 mL) to obtain the title compound (9.06 g, 89%) as a yellow solid.

$^1$H-NMR (400 MHz, DMSO-$d_6$): δ ppm: 2.16 (3H, s), 2.92 (3H, d, J=5.2 Hz), 5.53 (1H, d, J=2.4 Hz), 5.89 (1H, d, J=2.4 Hz), 6.40 (1H, dd, J=2.7, 9.4 Hz), 6.64 (1H, d, J=2.4 Hz), 8.15 (1H, d, J=9.4 Hz), 8.30-8.33 (1H, m), 11.52 (1H, brs).

(17b) 5-[(2-Methoxy-6-methylpyridin-4-yl)oxy]-N-methyl-2-nitroaniline

A solution of 6-methyl-4-[3-(methylamino)-4-nitrophenoxy]pyridin-2-ol produced in Example (17a) (7.85 g, 18.7 mmol), methyl iodide (4.66 mL, 74.8 mmol) and silver carbonate (10.32 g, 37.4 mmol) in chloroform (100 mL) was stirred in a nitrogen atmosphere at room temperature for five days. The insoluble matter was separated by filtration and the filtrate was concentrated under reduced pressure. Then, the residue was purified by silica gel chromatography (hexane/ethyl acetate, 5:1) to obtain the title compound (4.87 g, 90%) as a yellow solid.

$^1$H-NMR (400 MHz, CDCl$_3$): δ ppm: 2.44 (3H, s), 2.98 (3H, d, J=5.1 Hz), 3.93 (3H, s), 6.18 (1H, d, J=1.6 Hz), 6.32 (1H, dd, J=2.4, 9.4 Hz), 6.44-6.45 (2H, m), 8.18 (1H, brs), 8.22 (1H, d, J=9.4 Hz).

(17c) 4-[(2-Methoxy-6-methylpyridin-4-yl)oxy]-$N^2$-methylbenzene-1,2-diamine The reaction and post-treatment were carried out according to Example (1b) using 5-[(2-methoxy-6-methylpyridin-4-yl)oxy]-N-methyl-2-nitroaniline produced in Example (17b) (4.87 g, 16.8 mmol), iron powder (4.70 g, 84.2 mmol), ammonium chloride (0.45 g, 8.42 mmol), ethanol (80 mL) and water (40 mL) to obtain the title compound (4.37 g, 99%) as a brown oil.

$^1$H-NMR (500 MHz, CDCl$_3$): δ ppm: 2.38 (3H, s), 2.83 (3H, s), 3.38 (2H, brs), 3.88 (3H, s), 6.02 (1H, d, J=2.0 Hz), 6.36-6.38 (3H, m), 6.70 (1H, d, J=8.8 Hz).

(17d) Methyl 3-[2-({4-[(2-methoxy-6-methylpyridin-4-yl)oxy]-2-(methylamino)phenyl}amino)-2-oxoethoxy]benzoate The reaction and post-treatment were carried out according to Example (16e) using 4-[(2-methoxy-6-methylpyridin-4-yl)oxy]-$N^2$-methylbenzene-1,2-diamine produced in Example (17c) (4.13 g, 15.9 mmol), [3-(methoxycarbonyl)phenoxy]acetic acid produced in Example (1c) (3.68 g, 17.5 mmol), triethylamine (4.44 mL, 31.8 mmol), pivaloyl chloride (1.96 mL, 15.9 mmol) and dichloromethane (80 mL) to obtain the title compound (4.44 g, 64%) as a white powder.

$^1$H-NMR (500 MHz, CDCl$_3$): δ ppm: 2.40 (3H, s), 2.79 (3H, s), 3.90 (3H, s), 3.95 (3H, s), 3.99 (1H, brs), 4.76 (2H, s), 6.09 (1H, d, J=1.5 Hz), 6.39 (1H, d, J=2.0 Hz), 6.46-6.48 (2H, m), 7.23 (1H, dd, J=2.4, 8.3 Hz), 7.24-7.27 (1H, m), 7.46 (1H, t, J=7.8 Hz), 7.69 (1H, s), 7.78 (1H, d, J=7.8 Hz), 7.93 (1H, brs).

(17e) Methyl 3-({6-[(2-Methoxy-6-methylpyridin-4-yl)oxy]-1-methyl-1H-benzimidazol-2-yl}methoxy)benzoate The reaction and post-treatment were carried out according to Example (16f) using methyl 3-[2-({4-[(2-methoxy-6-methylpyridin-4-yl)oxy]-2-(methylamino)phenyl}amino)-2-oxoethoxy]benzoate produced in Example (17d) (4.44 g, 9.83 mmol) and acetic acid (50 mL) to obtain the title compound (4.12 g, 99%) as a white powder.

$^1$H-NMR (400 MHz, CDCl$_3$): δ ppm: 2.39 (3H, s), 3.86 (3H, s), 3.88 (3H, s), 3.93 (3H, s), 5.42 (2H, s), 6.00 (1H, s), 6.36 (1H, s), 7.04 (1H, dd, J=2.0, 8.6 Hz), 7.09 (1H, d, J=2.0 Hz), 7.29-7.32 (1H, m), 7.39 (1H, t, J=7.4 Hz), 7.70 (1H, dd, J=1.6, 7.8 Hz), 7.73-7.74 (1H, m), 7.78 (1H, d, J=8.6 Hz).

(17f) 3-({6-[(2-Methoxy-6-methylpyridin-4-yl)oxy]-1-methyl-1H-benzimidazol-2-yl}methoxy)benzoic acid The reaction and post-treatment were carried out according to Example (1g) using methyl 3-({6-[(2-Methoxy-6-methylpyridin-4-yl)oxy]-1-methyl-1H-benzimidazol-2-yl}methoxy)benzoate produced in Example (17e) (4.12 g, 9.50 mmol), a 1 M sodium hydroxide aqueous solution (25 mL) and methanol (50 mL) to obtain the title compound (3.85 g, 99%) as a white solid.

$^1$H-NMR (500 MHz, DMSO-$d_6$): δ ppm: 2.31 (3H, s), 3.79 (3H, s), 3.85 (3H, s), 5.48 (2H, s), 6.00 (1H, d, J=2.0 Hz), 6.43 (1H, d, J=2.0 Hz), 7.01 (1H, dd, J=2.0, 8.3 Hz), 7.39 (1H, ddd, J=1.0, 2.9, 7.3 Hz), 7.46 (1H, t, J=7.8 Hz), 7.48 (1H, d, J=2.0 Hz), 7.58 (1H, dt, J=1.5, 7.3 Hz), 7.64 (1H, dd, J=1.5, 2.4 Hz), 7.71 (1H, d, J=8.3 Hz), 13.03 (1H, brs);

Anal. Calcd for $C_{23}H_{21}N_3O_5$: C, 65.86; H, 5.05; N, 10.02. Found C, 65.66; H, 4.96; N, 9.94.

Example 18

3-({6-[(6-Methoxypyridin-3-yl)oxy]-1-methyl-1H-benzimidazol-2-yl}methoxy)benzoic acid

[Formula 23]

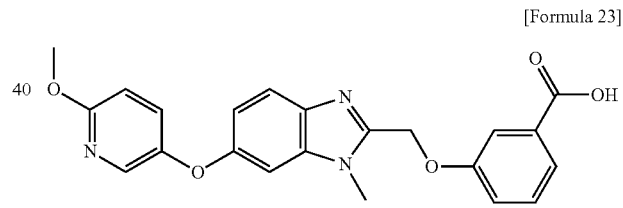

(18a) tert-Butyl {5-[(6-chloropyridin-3-yl)oxy]-2-nitrophenyl}methylcarbamate The reaction and post-treatment were carried out according to Example (1a) using 6-chloropyridin-3-ol (10 g, 77 mmol), tert-butyl (5-chloro-2-nitrophenyl)methylcarbamate (19 g, 66 mmol), sodium hydride (56%, 3.1 g, 77 mmol) and N-methylpyrrolidinone (80 mL) to obtain the title compound.

$^1$H-NMR (400 MHz, CDCl$_3$): δ ppm: 1.32 (6H, s), 1.50 (3H, brs), 3.27 (3H, s), 6.92 (1H, d, J=2.7 Hz), 6.88 (1H, d, J=9.0 Hz), 7.43 (2H, brs), 7.97 (1H, d, J=9.4 Hz), 8.26 (1H, dd, J=1.0, 2.2 Hz).

(18b) tert-Butyl {2-amino-5-[(6-chloropyridin-3-yl)oxy]phenyl}methylcarbamate The reaction and post-treatment were carried out according to Example (1b) using tert-butyl{5-[(6-chloropyridin-3-yl)oxy]-2-nitrophenyl}methylcarbamate produced in Example (18a) (8.0 g, 21 mmol), iron powder (5.6 g, 105 mmol), ammonium chloride (0.56 g, 11 mmol), ethanol (40 mL) and water (20 mL) to obtain the title compound (7.4 g, 99%) as a brown oil.

$^1$H-NMR (400 MHz, CDCl$_3$): δ ppm: 1.40 (9H, brs), 3.15 (3H, s), 3.72 (2H, brs), 6.75-6.82 (1H, m), 6.79 (2H, d, J=7.8 Hz), 7.17-7.24 (2H, m), 8.09 (1H, brs).

(18c) Methyl 3-[2-({2-[(tert-butoxycarbonyl)(Methyl)amino]-4-[(6-chloropyridin-3-yl)oxy]phenyl}amino)-2-oxoethoxy]benzoate The reaction and post-treatment were carried out according to Example (1d) using tert-butyl {2-amino-5-[(6-chloropyridin-3-yl)oxy]phenyl}methylcarbamate produced in Example (18b) (7.4 g, 21 mmol), [3-(methoxycarbonyl)phenoxy]acetic acid produced in Example (1c) (4.4 g, 21 mmol), 1-ethyl-3-(3-dimethylaminopropyl)carbodiimide hydrochloride (4.8 g, 25 mmol) and dichloromethane (80 mL) to obtain the title compound (8.0 g, 70%).

$^1$H-NMR (400 MHz, CDCl$_3$): δ ppm: 3.12 (3H, s), 3.93 (3H, s), 4.69 (2H, s), 6.90 (1H, d, J=2.4 Hz), 6.97 (1H, dd, J=9.0, 2.7 Hz), 7.20 (1H, dd, J=8.2, 2.4 Hz), 7.29 (3H, d, J=1.6 Hz), 7.42 (1H, t, J=8.0 Hz), 7.64 (1H, brs), 7.75 (1H, d, J=7.8 Hz), 8.17 (1H, s);
MS (FAB) m/z: 542 (M+H)$^+$.

(18d) Methyl 3-({6-[(6-chloropyridin-3-yl)oxy]-1-methyl-1H-benzimidazol-2-yl}methoxy)benzoate The reaction and post-treatment were carried out according to Example (1e) using methyl 3-[2-({2-[(tert-butoxycarbonyl)(methyl)amino]-4-[(6-chloropyridin-3-yl)oxy]phenyl}amino)-2-oxoethoxy]benzoate produced in Example (18c) (8.0 g, 14 mmol) and a 4 M hydrochloric acid/ethyl acetate solution (40 mL) to obtain the title compound (4.9 g, 78%) as a white solid.

$^1$H-NMR (400 MHz, CDCl$_3$): δ ppm: 3.85 (3H, s), 3.93 (3H, s), 5.41 (2H, s), 7.00-7.04 (2H, m), 7.24-7.32 (3H, m), 7.39 (1H, t, J=7.9 Hz), 7.70 (1H, dt, J=1.1, 7.5 Hz), 7.72-7.74 (1H, m), 7.78 (1H, d, J=9.4 Hz), 8.17 (1H, dd, J=1.6, 2.4 Hz);
MS (FAB) m/z: 424 (M+H)$^+$.

(18e) 3-({6-[(6-Chloropyridin-3-yl)oxy]-1-methyl-1H-benzimidazol-2-yl}methoxy)benzoic acid The reaction and post-treatment were carried out according to Example (1g) using methyl 3-({6-[(6-chloropyridin-3-yl)oxy]-1-methyl-1H-benzimidazol-2-yl}methoxy)benzoate produced in Example (18d) (4.9 g, 12 mmol), a 1 M sodium hydroxide aqueous solution (17 mL) and 1,4-dioxane (20 mL) to obtain the title compound (4.6 g, 97%) as a white solid.

$^1$H-NMR (500 MHz, DMSO-d$_6$): δ ppm: 3.83 (3H, s), 5.48 (2H, s), 7.03 (1H, dd, J=2.4, 8.7 Hz), 7.37-7.41 (1H, m), 7.43-7.51 (4H, m), 7.58 (1H, dt, J=1.2, 7.4 Hz), 7.64 (1H, dd, J=1.4, 2.5 Hz), 7.71 (1H, d, J=8.7 Hz), 8.22 (1H, t, J=1.4 Hz), 13.07 (1H, brs).

(18f) 3-({6-[(6-Methoxypyridin-3-yl)oxy]-1-methyl-1H-benzimidazol-2-yl}methoxy)benzoic acid A solution of 3-({6-[(6-chloropyridin-3-yl)oxy]-1-methyl-1H-benzimidazol-2-yl}methoxy)benzoic acid produced in Example (18e) (0.40 g, 0.98 mmol) and sodium hydride (63%, 0.372 g, 9.76 mmol) in methanol (9.8 mL) was heated under reflux under microwave irradiation for two hours. After leaving to cool, water was added to the reaction mixture. This aqueous solution was washed with hexane five times and neutralized by adding 1 M hydrochloric acid. The precipitated solid was collected by filtration to obtain the crude title compound. A suspension of the crude title compound in ethanol (5 mL) and water (5 mL) was heated under reflux for two hours and left to cool. Then, the precipitated solid was collected by filtration to obtain the title compound (0.312 g, 79%) as a white solid.

$^1$H-NMR (400 MHz, DMSO-d$_6$): δ ppm: 3.80 (3H, s), 3.84 (3H, s), 5.46 (2H, s), 6.86 (1H, d, J=9.0 Hz), 6.93 (1H, dd, J=2.4, 9.0 Hz), 7.24 (1H, d, J=2.4 Hz), 7.35-7.40 (1H, m), 7.44 (1H, d, J=7.8 Hz), 7.48 (1H, dd, J=2.7, 9.0 Hz), 7.57 (1H, d, J=7.4 Hz), 7.61-7.65 (2H, m), 7.99 (1H, d, J=3.1 Hz), 13.04 (1H, brs);
Anal. Calcd for C$_{22}$H$_{19}$N$_3$O$_5$: C, 65.18; H, 4.72; N, 10.37. Found C, 63.51; H, 4.95; N, 10.00.

Example 19

3-({6-[(5-Ethylpyridin-3-yl)oxy]-1-methyl-1H-benzimidazol-2-yl}methoxy)benzoic acid

[Formula 24]

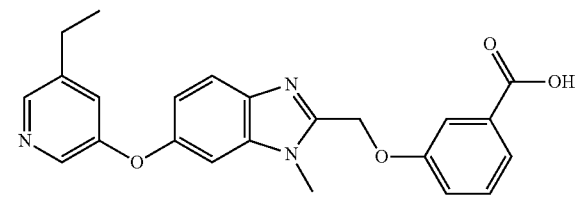

(19a) tert-Butyl {5-[(5-bromopyridin-3-yl)oxy]-2-nitrophenyl}methylcarbamate

The reaction and post-treatment were carried out according to Example (1a) using 5-bromo-3-hydroxypyridine (5.01 g, 28.8 mmol), tert-butyl (5-chloro-2-nitrophenyl)methylcarbamate (US200216506 A1, 7.50 g, 26.2 mmol), sodium hydride (63%, 1.10 g, 28.8 mmol) and DMF (87 mL) to obtain the title compound (11.1 g, 99%) as a yellow brown solid.

$^1$H-NMR (400 MHz, CDCl$_3$): δ ppm: 1.33 (9H, brs), 3.28 (3H, s), 6.90 (1H, dd, J=2.7, 9.0 Hz), 6.93-6.96 (1H, m), 7.59-7.62 (1H, m), 7.96-8.02 (1H, m), 8.41 (1H, d, J=2.4 Hz), 8.58 (1H, s).

(19b) tert-Butyl {2-amino-5-[(5-bromopyridin-3-yl)oxy]phenyl}methylcarbamate

The reaction and post-treatment were carried out according to Example (1b) using tert-butyl {5-[(5-bromopyridin-3-yl)oxy]-2-nitrophenyl}methylcarbamate produced in Example (19a) (11.1 g, 26.2 mmol), iron powder (4.38 g, 78.5 mol), ammonium chloride (0.70 g, 13.1 mmol), ethanol (87 mL) and water (40 mL) to obtain the title compound (9.63 g, 94%) as a brown solid.

$^1$H-NMR (400 MHz, CDCl$_3$): δ ppm: 1.41 (9H, brs), 3.15 (3H, s), 3.76 (2H, brs), 6.75-6.85 (3H, m), 7.32 (1H, brs), 8.26-8.29 (1H, m), 8.33-8.35 (1H, m).

(19c) Methyl 3-[2-({4-[(5-bromopyridin-3-yl)oxy]-2-[(tert-butoxycarbonyl)(methyl)amino]-2-oxoethoxy]benzoate The reaction and post-treatment were carried out according to Example (1d) using [3-(methoxycarbonyl)phenoxy]acetic acid produced in Example (1c) (5.65 g, 26.9 mmol), tert-butyl {2-amino-5-[(5-bromopyridin-3-yl)oxy]phenyl}methylcarbamate produced in Example (19b) (9.63 g, 24.4 mmol), 1-hydroxybenzotriazole (0.33 g, 2.44 mmol), 1-ethyl-3-(3-dimethylaminopropyl)carbodiimide hydrochloride (5.15 g, 26.9 mmol) and methylene chloride (81 mL) to obtain the title compound (14.3 g, 99%) as a brown solid.

$^1$H-NMR (500 MHz, CDCl$_3$): δ ppm: 1.42 (9H, brs), 3.13 (3H, s), 3.93 (3H, s), 4.70 (2H, s), 6.93 (1H, s), 6.99-7.03 (1H, m), 7.19-7.22 (1H, m), 7.43 (2H, t, J=7.8 Hz), 7.64 (1H, s), 7.74-7.77 (1H, m), 8.33 (1H, d, J=2.0 Hz), 8.43 (1H, d, J=2.0 Hz).

(19d) Methyl 3-({6-[(5-bromopyridin-3-yl)oxy]-1-methyl-1H-benzimidazol-2-yl}methoxy)benzoate The reaction and post-treatment were carried out according to Example (1e) using methyl 3-[2-({4-[(5-bromopyridin-3-yl)oxy]-2-[(tert-butoxycarbonyl)(methyl)amino]-2-oxoethoxy]benzoate produced in Example (19c) (14.3 g, 24.4 mmol), a 4 M hydrochloric acid/1,4-dioxane solution (24 mL) and 1,4-dioxane (12 mL) to obtain the title compound (10.9 g, 96%) as a pale brown solid.

$^1$H-NMR (400 MHz, CDCl$_3$): δ ppm: 3.71 (3H, s), 3.93 (3H, s), 5.42 (2H, s), 7.03 (1H, dd, J=2.4, 8.6 Hz), 7.06 (1H, d, J=2.4 Hz), 7.28-7.32 (1H, m), 7.36-7.42 (2H, m), 7.68-7.75 (2H, m), 7.80 (1H, d, J=8.6 Hz), 8.34 (1H, d, J=2.7 Hz), 8.40 (1H, d, J=2.0 Hz).

(19e) Methyl 3-({6-[(5-ethylpyridin-3-yl)oxy]-1-methyl-1H-benzimidazol-2-yl}methoxy)benzoate The reaction and post-treatment were carried out according to Example (2b) using methyl 3-({6-[(5-bromopyridin-3-yl)oxy]-1-methyl-1H-benzimidazol-2-yl}methoxy)benzoate produced in Example (19d) (2.00 g, 4.27 mmol), triethylborane (1.0 M solution in THF, 8.54 mL, 8.54 mmol), a [1,1'-bis(diphenylphosphino)-ferrocene]dichloropalladium (II)-dichloromethane mixture (0.17 g, 0.21 mmol), potassium carbonate (0.89 g, 6.41 mmol) and DMF (21 mL) to obtain the title compound (0.596 g, 34%) as a white solid.

$^1$H-NMR (400 MHz, CDCl$_3$): δ ppm: 1.23 (3H, t, J=7.6 Hz), 2.63 (2H, q, J=7.6 Hz), 3.84 (3H, s), 3.93 (3H, s), 5.41 (2H, s), 7.01-7.05 (2H, m), 7.10-7.13 (1H, m), 7.27-7.32 (1H, m), 7.38 (1H, t, J=7.8 Hz), 7.67-7.78 (3H, m), 8.21-8.24 (2H, m).

(19f) 3-({6-[(5-Ethylpyridin-3-yl)oxy]-1-methyl-1H-benzimidazol-2-yl}methoxy)benzoic acid The reaction and post-treatment were carried out according to Example (1g) using methyl 3-({6-[(5-ethylpyridin-3-yl)oxy]-1-methyl-1H-benzimidazol-2-yl}methoxy)benzoate produced in Example (19e) (0.590 g, 1.41 mmol), a 1 M sodium hydroxide aqueous solution (2.12 mL) and 1,4-dioxane (7.1 mL) to obtain the title compound (0.551 g, 97%) as a white solid.

$^1$H-NMR (400 MHz, DMSO-d$_6$): δ ppm: 1.15 (3H, t, J=7.6 Hz), 2.60 (2H, q, J=7.6 Hz), 3.83 (3H, s), 5.48 (2H, s), 6.99 (1H, dd, J=2.4, 8.6 Hz), 7.23-7.25 (1H, m), 7.37-7.42 (2H, m), 7.46 (1H, t, J=7.8 Hz), 7.56-7.60 (1H, m), 7.63-7.65 (1H, m), 7.69 (1H, d, J=8.6 Hz), 8.17 (1H, d, J=2.7 Hz), 8.21 (1H, d, J=1.6 Hz), 13.10 (1H, brs);

Anal. Calcd for C$_{23}$H$_{21}$N$_3$O$_4$: C, 68.47; H, 5.25; N, 10.42. Found C, 68.28; H, 5.12; N, 10.33.

Test Example 1

Hypoglycemic Effect

Six-week-old male KK mice were purchased from CLEA Japan, Inc. and then were fed until 15 to 20 weeks old to develop diabetes. The mice were individually fed during the adaptation period and the test period, and water and feed (FR2, Funabashi Farm) were freely ingested.

At the start of the experiment, after body weight measurement, blood was collected from the tail vein of the mice into a heparin-coated glass tube and centrifuged, and then plasma was separated. The glucose level in the plasma was measured by Glucoloader GXT (A&T Corp.), and individuals having a plasma glucose level of about 350 mg/dl or more were selected. The mice were grouped, each group having 3 to 4 mice, to make the average body weight and the average plasma glucose level similar. Each compound was administered to a compound group with a diet admixture containing 0.03% of the compound. A separate group in which the mice were fed only with diet was a control group.

The experiment period (drug administration period) was three days. The grouping day was the 0th day. On the 3rd day, the body weight was measured and blood was collected from the tail vein to measure the plasma glucose level.

The glucose lowering rate was determined by the following formula.

Glucose lowering rate=[(Control group plasma glucose level−Compound-administered group plasma glucose level)/Control group plasma glucose level]×100

The higher the glucose lowering rate of the compound, the more potent the hypoglycemic effect of the compound.

The following Compound A described as Example 26 in WO 2008/126732 was used as a comparative compound.

[Formula 25]

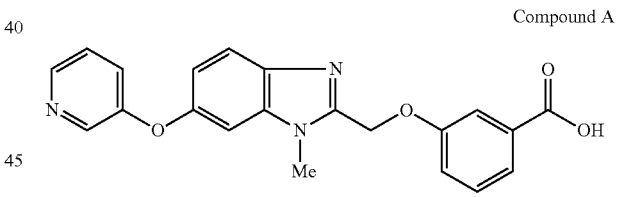

Compound A

The results of comparing the compounds of the present invention with the comparative Compound A are shown in Table 1.

TABLE 1

| Example | Glucose lowering rate (%) |
| --- | --- |
| 2 | 31 |
| 4 | 28 |
| 5 | 34 |
| 8 | 33 |
| 9 | 41 |
| 10 | 37 |
| 15 | 30 |
| 16 | 17 |
| 17 | 36 |
| Compound A | 20. |

As is clear from Table 1, the compounds of the present invention have a hypoglycemic effect equal to or greater than that of Compound A described in WO 2008/126732. Accordingly, the compounds of the present invention are assumed to be useful as therapeutic agents for diabetes (especially therapeutic agents for type II diabetes).

Test Example 2

Measurement of PPARγ Activation Effect/Modulator Activity

Rosiglitazone used in Examples is a commercially available PPARγ activator and is a compound described in U.S. Pat. No. 5,002,953, and can be produced according to the method described therein.

A test was carried out according to the reporter assay method with reference to a report by Kliewer et al. (Journal of Biological Chemistry, 1995, Vol. 270 (22), p. 12953-12956) as a method for measuring the ability of a compound to activate PPARγ (hereinafter PPARγ activation effect/modulator activity). Commercially available reagents and kits were used according to the attached instructions. The details will be shown below.

(1) Preparation of GAL4-PPARγ Chimeric Receptor Expression Plasmid

The ligand-binding domain of human PPARγ (corresponding to about 300 amino acids at the carboxy end) was bound to the DNA-binding domain of the yeast transcription factor GAL4 (corresponding to 147 amino acids at the amino end) with reference to the report by Kliewer et al. to prepare a gene expressing a GAL4-PPARγ receptor.

The base sequence of the human PPARγ gene is described in the gene database GenBank under Accession No. X90563.

(1-1) Extraction of Total RNA from Cell Line HepG2

The cell line HepG2 (American Type Culture Collection HB-8065) was purchased from Dainippon Pharmaceutical Co., Ltd. and cultured in a tissue culture flask having a culture area of 75 cm$^2$ (manufactured by BD Biosciences). Dulbecco's modified Eagle's medium (Gibco D-MEM, manufactured by Invitrogen Corporation) supplemented with fetal bovine serum (manufactured by HyClone) at a volume ratio of 10% and an antibiotic solution [Antibiotic Antimycotic Solution, stabilized (100×), manufactured by Sigma] at a volume ratio of 1% was used as a medium.

The cells were cultured in a carbon dioxide incubator at 37° C. under 5% carbon dioxide for three days. When the cells were grown to an approximately semiconfluent state, the medium in the flask was removed by aspiration. The cells were washed by adding 10 ml of ice-cooled phosphate-buffered saline (Gibco Dulbecco's Phosphate-Buffered Saline, manufactured by Invitrogen Corporation), and then the saline was removed by aspiration. Thereafter, 7.5 ml of Trizol reagent (Gibco TRIZOL reagent, manufactured by Invitrogen Corporation) was added to the cells in the flask, and repeatedly pipetted. The cells were lysed by incubating at room temperature for about five minutes.

The cell lysate was subjected to precipitation with isopropyl alcohol according to the instructions of the Trizol reagent. The resulting RNA precipitate was dissolved in pure water and stored in a freezer at about −20° C. Here, the volume of the RNA solution was 0.22 ml. A sample obtained by diluting a part of the RNA solution 100-fold with pure water had an absorbance at 260 nm of 0.562. The yield of the total RNA was calculated to be 0.562×100×39.5×0.22=488 μg assuming that 39.5 μg/ml of RNA was present when the absorbance was 1.

(1-2) Cloning of cDNA of PPARγ Ligand-Binding Domain

Two oligonucleotides represented by SEQ ID NOS: 1 and 2 in the later-described Sequence Listing, as designed based on the gene sequence of human PPARγ, were chemically synthesized as primers for amplification by reverse transcript polymerase chain reaction (hereinafter RT-PCR) of cDNA of the PPARγ ligand-binding domain using Beckman Oligo 1000 (manufactured by Beckman).

cDNA of PPARγ was amplified by RT-PCR using Ready-To-Go RT-PCR Beads (manufactured by Amersham Pharmacia Biotech, Inc.) with the HepG2 total RNA previously obtained as a template and the two oligonucleotides as primers. The reaction product was subjected to 1.5% agarose electrophoresis. The amplified band of about 900 base pairs was cut out, purified, and cloned to the plasmid pCRII (manufactured by Invitrogen Corporation). The amplified DNA fragment is assumed to have the nucleotide sequence represented by SEQ ID NO: 3 of the Sequence Listing which includes a sequence encoding the ligand-binding domain, specifically, amino acids 175 to 475, of human PPARγ, and to which a restriction enzyme BamHI cleavage site and a restriction enzyme HindIII site are added on the 5'-terminal and 3'-terminal, respectively. The plasmid clone correctly containing the sequence represented by SEQ ID NO: 3 was selected by confirming the nucleotide sequence.

(1-3) Production of Plasmid pM-PPARγ

Next, the selected plasmid was treated with restriction enzymes BamHI and HindIII to obtain a 900-base-pair fragment containing the gene of the PPARγ ligand-binding domain. This was inserted into the BamHI-HindIII site of the plasmid pM having the gene of the DNA-binding domain of the yeast transcription factor GAL4 (manufactured by Clontech Laboratories, Inc.) and cloned.

The plasmid pM-PPARγ obtained by the above operation includes the nucleotide sequence represented by SEQ ID NO: 4 of the Sequence Listing and encodes an amino acid sequence represented by SEQ ID NO: 5 of the Sequence Listing containing amino acids 1 to 147 of the yeast transcription factor GAL4 at the amino end and containing amino acids 175 to 475 of human PPARγ and a stop codon at the carboxy end. The plasmid is a gene that can express a GAL4-PPARγ chimeric receptor in mammalian cells.

(2) Measurement of PPARγ Activation Ability

The previously acquired plasmid pM-PPARγ and the plasmid pFR-Luc purchased from Stratagene Cloning Systems, Inc. were dissolved in deionised water at a concentration of 1 mg/mL each.

The monkey kidney-derived cell line COS-7 (American Type Culture Collection CRL-1651) was seeded into a 75 cm$^2$ culture flask and cultured using Dulbecco's modified Eagle's medium containing 10% fetal bovine serum (hereinafter medium) under the conditions of 37° C. and 5% carbon dioxide gas until an approximately 80% confluent state was obtained.

COS-7 cells were transfected with 4.8 micrograms per flask of the plasmid pM-PPARγ and 19.2 μg per flask of the plasmid pFR-Luc using Lipofectamine 2000 transfection reagent (manufactured by Invitrogen Corporation), and the cells were cultured overnight.

On the following day, the cells were harvested by trypsin treatment, suspended in 75 mL of phenol red-free Dulbecco's modified Eagle's medium containing 10% fetal bovine serum, seeded into a white 96-well plate (manufactured by Costar) using the medium in a volume of 95 μL per well, and cultured overnight.

The test compound was dissolved in dimethyl sulfoxide at a concentration of 4 mM. The solution was serially diluted 3.3-fold with dimethyl sulfoxide to prepare solutions of the compound at concentrations up to 400 nM. Dimethyl sulfoxide was prepared for the control group. Rosiglitazone dissolved in dimethyl sulfoxide at a concentration of 4 mM was prepared for the positive control group. They were diluted 20-fold with the medium, and 5 μL of the dilution was added to the wells in which the cells were grown. The concentrations of the test compound treating the cells ranged from 10 μM to 1 nM. After the addition, the cells were cultured overnight.

On the following day, the medium was removed, and Luc Lite (manufactured by PerkinElmer Inc.) was prepared according to the attached document and added at 50 microliters per well. The plate with cells in the Luc Lite was stirred for about 30 minutes. The amount of luminescence in each well was measured as luciferase activity using Analyst (Molecular Devices) for 0.5 second. A dose-dependent curve was drawn.

When the luciferase activity of the positive control group was 100% and the luciferase activity of the control group was 0%, the maximum luciferase activity exhibited by the test compound alone was calculated as Emax (%) and the concentration of the test compound represented by Emax/2 was calculated as EC50.

The smaller the EC50 value of the compound, the more potent the PPARγ activation effect/modulator activity of the compound.

Compound A used in Test Example 1 was used as a comparative compound.

The results of comparing the compounds of the present invention with the comparative Compound A are shown in Table 2.

TABLE 2

| Example | $EC_{50}$ (nM) | Emax (%) |
|---|---|---|
| 2 | 180 | 73 |
| 4 | 180 | 81 |
| 5 | 24 | 79 |
| 8 | 100 | 100 |
| 9 | 43 | 74 |
| 10 | 51 | 60 |
| 11 | 260 | 82 |
| 12 | 71 | 83 |
| 14 | 69 | 67 |
| 15 | 120 | 94 |
| 16 | 190 | 110 |
| 17 | 100 | 110 |
| 18 | 160 | 100 |
| Compound A | 6800 | 66. |

As shown in Table 2, the compounds of the present invention have PPARγ activation effect/modulator activity equal to or greater than that of Compound A described in WO 2008/126732. Accordingly, the compounds of the present invention are assumed to be useful as therapeutic agents or prophylactic agents for a disease based on dyslipidemia, arteriosclerosis, hyperlipidemia, diabetes, involutional osteoporosis, adiposis, cancer, or the like.

Formulation Example 1

Capsules

| Compound of Example 1 or 2 | 50 mg |
|---|---|
| Lactose | 128 mg |
| Corn starch | 70 mg |
| Magnesium stearate | 2 mg |
| | 250 mg |

The above-formulated powder is mixed and allowed to pass through a 60-mesh sieve. Then, the powder is put in 250 mg gelatin capsules to prepare capsules.

Formulation Example 2

Tablets

| Compound of Example 1 or 2 | 50 mg |
|---|---|
| Lactose | 126 mg |
| Corn starch | 23 mg |
| Magnesium stearate | 1 mg |
| | 200 mg |

The above-formulated powder is mixed, granulated using a corn starch paste, dried, and then tableted using a tableting machine to prepare tablets each having a weight of 200 mg. The tablets may be sugar-coated as necessary.

Industrial Applicability

The compounds represented by the general formula (I) or pharmacologically acceptable esters thereof, or pharmacologically acceptable salts of the compounds or esters according to the present invention have excellent hypoglycemic effects and are useful as therapeutic agents and/or prophylactic agents for metabolic syndrome, specifically, a disease such as diabetes, hyperglycemia, hyperlipidemia, adiposity, impaired glucose tolerance (IGT), insulin resistance, impaired fasting glucose (IFG), hypertension, fatty liver, non-alcoholic steatohepatitis (NASH), diabetic complications (such as retinopathy, nephropathy or neuropathy), arteriosclerosis, gestational diabetes mellitus (GDM) or polycystic ovary syndrome (PCOS), inflammatory disease (such as osteoarthritis, pain or inflammatory enteritis), acne, sunburn, psoriasis, eczema, allergic disease, asthma, peptic ulcer, ulcerative colitis, Crohn's disease, coronary artery disease, arteriosclerosis, atherosclerosis, diabetic retinopathy, diabetic maculopathy, macular edema, diabetic nephropathy, ischemic heart disease, cerebrovascular disorder, peripheral circulatory disturbance, autoimmune disease (such as systemic lupus erythematosus, chronic rheumatism, Sjogren's syndrome, systemic sclerosis, mixed connective tissue disease, Hashimoto's disease, Crohn's disease, ulcerative colitis, idiopathic Addison's disease, male sterility, Goodpasture's syndrome, rapidly progressive glomerulonephritis, myasthenia gravis, polymyositis, multiple sclerosis, autoimmune hemolytic anemia, idiopathic thrombocytopenic purpura, Behcet's disease or CREST syndrome), pancreatitis, cachexia, cancer (such as gastric cancer, lung cancer, breast cancer, colon cancer, prostate cancer, pancreatic cancer or liver cancer), leukemia, sarcoma (such as liposarcoma), osteoporosis, involutional osteoporosis, neurodegenerative disease, Alzheimer's disease, hyperuricemia, or dry eyes.

Sequence Listing Free Text

SEQ ID NO: 1: PCR sense primer

SEQ ID NO: 2: PCR antisense primer

SEQ ID NO: 3: Nucleotide sequence of synthetic human PPARγ cDNA

SEQ ID NO: 4: Nucleotide sequence of GAL4 chimeric PPARγ receptor gene

SEQ ID NO: 5: Amino acid sequence of GAL4 chimeric PPARγ receptor

The invention claimed is:

1. A compound having a formula (I):

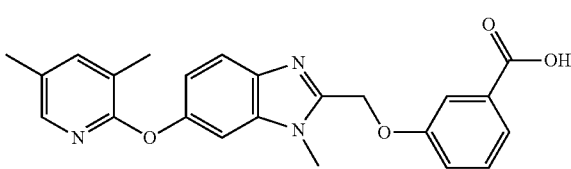

(I)

or a pharmacologically acceptable $C_1$ to $C_4$ alkyl ester of the compound, or a pharmacologically acceptable salt of the compound or the ester.

2. The compound according to claim 1 that is: 3-({6-[(3,5-dimethylpyridin-2-yl)oxy]-1-methyl-1H-benzimidazol-2-yl}methoxy)benzoic acid.

3. The compound according to claim 1 that is: a pharmacologically acceptable salt of 3-({6-[(3,5-dimethylpyridin-2-yl)oxy]-1-methyl-1H-benzimidazol-2-yl}methoxy)benzoic acid.

4. The compound according to claim 1 that is: a calcium salt of 3-({6-[(3,5-dimethylpyridin-2-yl)oxy]-1-methyl-1H-benzimidazol-2-yl}methoxy)benzoic acid.

5. The compound according to claim 1 that is: a sodium salt of 3-({6-[(3,5-dimethylpyridin-2-yl)oxy]-1-methyl-1H-benzimidazol-2-yl}methoxy)benzoic acid.

6. The compound according to claim 1 that is: a hydrochloride salt of 3-({6-[(3,5-dimethylpyridin-2-yl)oxy]-1-methyl-1H-benzimidazol-2-yl}methoxy)benzoic acid.

7. A composition comprising the compound, or the pharmacologically acceptable $C_1$ to $C_4$ alkyl ester of the compound, or the pharmacologically acceptable salt of the compound or the ester of claim 1 and an inert carrier or diluent.

8. The composition according to claim 7, further comprising an additive.

9. The composition according to claim 8, wherein the additive is selected from the group consisting of: excipients, lubricants, binders, disintegrants, stabilizers, corrigents, diluents, and a combination thereof.

10. The composition according to claim 7, wherein the composition is for oral administration.

11. A method for the treatment of a disease selected from the group consisting of: diabetes, type II diabetes, impaired glucose tolerance, and gestational diabetes mellitus, the method comprising
administering a pharmacologically effective amount of the compound, or the pharmacologically acceptable ester of the compound, or the pharmacologically acceptable salt of the compound or the ester of claim 1 to a warm-blooded animal.

12. The method according to claim 11, wherein the warm-blooded animal is a human.

13. The method according to claim 12, wherein the disease is diabetes.

14. The method according to claim 12, wherein the disease is type II diabetes.

15. A method for lowering blood glucose levels in a human comprising
administering a pharmacologically effective amount of the compound, or the pharmacologically acceptable ester of the compound, or the pharmacologically acceptable salt of the compound or the ester of claim 1 to the human.

16. A method for improving insulin resistance in a human comprising
administering a pharmacologically effective amount of the compound, or the pharmacologically acceptable ester of the compound, or the pharmacologically acceptable salt of the compound or the ester of claim 1 to the human.

17. A method for activating peroxisome proliferator-activated receptor (PPAR) γ in a human, comprising
administering a pharmacologically effective amount of the compound, or the pharmacologically acceptable ester of the compound, or the pharmacologically acceptable salt of the compound or the ester of claim 1 to the human.

* * * * *

SEQUENCE LISTING

```
<160> NUMBER OF SEQ ID NOS: 5

<210> SEQ ID NO 1
<211> LENGTH: 29
<212> TYPE: DNA
<213> ORGANISM: Artificial
<220> FEATURE:
<223> OTHER INFORMATION: Inventor: Shinozuka, Tsuyoshi; Tsukada,
      Tomoharu Inventor: Fujii, Kunihiko; Mori, Makoto
<220> FEATURE:
<223> OTHER INFORMATION: PCR sense primer

<400> SEQUENCE: 1
ggatccataa tgccatcagg tttgggcgg                                           29

<210> SEQ ID NO 2
<211> LENGTH: 30
<212> TYPE: DNA
<213> ORGANISM: Artificial
<220> FEATURE:
<223> OTHER INFORMATION: PCR antisense primer

<400> SEQUENCE: 2
aagcttctag tacaagtcct tgtagatctc                                          30

<210> SEQ ID NO 3
<211> LENGTH: 917
<212> TYPE: DNA
<213> ORGANISM: Artificial Sequence
<220> FEATURE:
<223> OTHER INFORMATION: ScDNA coding ligand binding domain of human
      PPAR gamma

<400> SEQUENCE: 3
ggatccataa tgccatcagg tttgggcgga tgccacaggc cgagaaggag aagctgttgg         60
cggagatctc cagtgatatc gaccagctga atccagagtc cgctgacctc cgggccctgg       120
caaaacattt gtatgactca tacataaagt ccttcccgct gaccaaagca aaggcgaggg       180
cgatcttgac aggaaagaca acagacaaat caccattcgt tatctatgac atgaattcct       240
taatgatggg agaagataaa atcaagttca acacatcac cccctgcag gagcagagca         300 aagaggtggc catccgcatc tttcagggct gccagtttcg ctccgtggag gctgtgcagg       360
agatcacaga gtatgccaaa agcattcctg gttttgtaaa tcttgacttg aacgaccaag       420
taactctcct caaatatgga gtccacgaga tcatttacac aatgctggcc tccttgatga       480
ataaagatgg ggttctcata tccgagggcc aaggcttcat gacaagggag tttctaaaga       540
gcctgcgaaa gccttttggt gactttatgg agcccaagtt tgagtttgct gtgaagttca       600
atgcactgga attagatgac agcgacttgg caatatttat tgctgtcatt attctcagtg       660
gagaccgccc aggtttgctg aatgtgaagc ccattgaaga cattcaagac aacctgctac       720
aagccctgga gctccagctg aagctgaacc accctgagtc ctcacagctg tttgccaagc       780
tgctccagaa aatgacagac ctcagacaga ttgtcacgga cacgtgcag ctactgcagg       840 tgatcaagaa gacggagaca gacatgagtc ttcacccgct cctgcaggag atctacaagg       900
acttgtacta gaagctt                                                       917

<210> SEQ ID NO 4
<211> LENGTH: 1365
<212> TYPE: DNA
<213> ORGANISM: Artificial
```

```
<220> FEATURE:
<223> OTHER INFORMATION: GAL4-PPAR gamma chimeric receptor
<220> FEATURE:
<221> NAME/KEY: CDS
<222> LOCATION: (1)..(1365)

<400> SEQUENCE: 4 atg aag cta ctg tct tct atc gaa caa gca tgc gat att tgc cga ctt    48
Met Lys Leu Leu Ser Ser Ile Glu Gln Ala Cys Asp Ile Cys Arg Leu
1               5                   10                  15 aaa aag ctc aag tgc tcc aaa gaa aaa ccg aag tgc gcc aag tgt ctg    96
Lys Lys Leu Lys Cys Ser Lys Glu Lys Pro Lys Cys Ala Lys Cys Leu
                20                  25                  30 aag aac aac tgg gag tgt cgc tac tct ccc aaa acc aaa agg tct ccg   144
Lys Asn Asn Trp Glu Cys Arg Tyr Ser Pro Lys Thr Lys Arg Ser Pro
            35                  40                  45 ctg act agg gca cat ctg aca gaa gtg gaa tca agg cta gaa aga ctg   192
Leu Thr Arg Ala His Leu Thr Glu Val Glu Ser Arg Leu Glu Arg Leu
        50                  55                  60 gaa cag cta ttt cta ctg att ttt cct cga gaa gac ctt gac atg att   240
Glu Gln Leu Phe Leu Leu Ile Phe Pro Arg Glu Asp Leu Asp Met Ile
65                  70                  75                  80 ttg aaa atg gat tct tta cag gat ata aaa gca ttg tta aca gga tta   288
Leu Lys Met Asp Ser Leu Gln Asp Ile Lys Ala Leu Leu Thr Gly Leu
                85                  90                  95 ttt gta caa gat aat gtg aat aaa gat gcc gtc aca gat aga ttg gct   336
Phe Val Gln Asp Asn Val Asn Lys Asp Ala Val Thr Asp Arg Leu Ala
                100                 105                 110 tca gtg gag act gat atg cct cta aca ttg aga cag cat aga ata agt   384
Ser Val Glu Thr Asp Met Pro Leu Thr Leu Arg Gln His Arg Ile Ser
            115                 120                 125 gcg aca tca tca tcg gaa gag agt agt aac aaa ggt caa aga cag ttg   432
Ala Thr Ser Ser Ser Glu Glu Ser Ser Asn Lys Gly Gln Arg Gln Leu
        130                 135                 140 act gta tcg ccg gaa ttc ccg ggg atc cat aat gcc atc agg ttt ggg   480
Thr Val Ser Pro Glu Phe Pro Gly Ile His Asn Ala Ile Arg Phe Gly
145                 150                 155                 160 cgg atg cca cag gcc gag aag gag aag ctg ttg gcg gag atc tcc agt   528
Arg Met Pro Gln Ala Glu Lys Glu Lys Leu Leu Ala Glu Ile Ser Ser
                165                 170                 175 gat atc gac cag ctg aat cca gag tcc gct gac ctc cgg gcc ctg gca   576
Asp Ile Asp Gln Leu Asn Pro Glu Ser Ala Asp Leu Arg Ala Leu Ala
                180                 185                 190 aaa cat ttg tat gac tca tac ata aag tcc ttc ccg ctg acc aaa gca   624
Lys His Leu Tyr Asp Ser Tyr Ile Lys Ser Phe Pro Leu Thr Lys Ala
            195                 200                 205 aag gcg agg gcg atc ttg aca gga aag aca aca gac aaa tca cca ttc   672
Lys Ala Arg Ala Ile Leu Thr Gly Lys Thr Thr Asp Lys Ser Pro Phe
        210                 215                 220 gtt atc tat gac atg aat tcc tta atg atg gga gaa gat aaa atc aag   720
Val Ile Tyr Asp Met Asn Ser Leu Met Met Gly Glu Asp Lys Ile Lys
225                 230                 235                 240 ttc aaa cac atc acc ccc ctg cag gag cag agc aaa gag gtg gcc atc   768
Phe Lys His Ile Thr Pro Leu Gln Glu Gln Ser Lys Glu Val Ala Ile
                245                 250                 255 cgc atc ttt cag ggc tgc cag ttt cgc tcc gtg gag gct gtg cag gag   816
Arg Ile Phe Gln Gly Cys Gln Phe Arg Ser Val Glu Ala Val Gln Glu
                260                 265                 270 atc aca gag tat gcc aaa agc att cct ggt ttt gta aat ctt gac ttg   864
Ile Thr Glu Tyr Ala Lys Ser Ile Pro Gly Phe Val Asn Leu Asp Leu
            275                 280                 285
```

```
aac gac caa gta act ctc ctc aaa tat gga gtc cac gag atc att tac      912
Asn Asp Gln Val Thr Leu Leu Lys Tyr Gly Val His Glu Ile Ile Tyr
    290                 295                 300 aca atg ctg gcc tcc ttg atg aat aaa gat ggg gtt ctc ata tcc gag      960
Thr Met Leu Ala Ser Leu Met Asn Lys Asp Gly Val Leu Ile Ser Glu
305                 310                 315                 320 ggc caa ggc ttc atg aca agg gag ttt cta aag agc ctg cga aag cct     1008
Gly Gln Gly Phe Met Thr Arg Glu Phe Leu Lys Ser Leu Arg Lys Pro
                325                 330                 335 ttt ggt gac ttt atg gag ccc aag ttt gag ttt gct gtg aag ttc aat     1056
Phe Gly Asp Phe Met Glu Pro Lys Phe Glu Phe Ala Val Lys Phe Asn
            340                 345                 350 gca ctg gaa tta gat gac agc gac ttg gca ata ttt att gct gtc att     1104
Ala Leu Glu Leu Asp Asp Ser Asp Leu Ala Ile Phe Ile Ala Val Ile
        355                 360                 365 att ctc agt gga gac cgc cca ggt ttg ctg aat gtg aag ccc att gaa     1152
Ile Leu Ser Gly Asp Arg Pro Gly Leu Leu Asn Val Lys Pro Ile Glu
    370                 375                 380 gac att caa gac aac ctg cta caa gcc ctg gag ctc cag ctg aag ctg     1200
Asp Ile Gln Asp Asn Leu Leu Gln Ala Leu Glu Leu Gln Leu Lys Leu
385                 390                 395                 400 aac cac cct gag tcc tca cag ctg ttt gcc aag ctg ctc cag aaa atg     1248
Asn His Pro Glu Ser Ser Gln Leu Phe Ala Lys Leu Leu Gln Lys Met
                405                 410                 415 aca gac ctc aga cag att gtc acg gaa cac gtg cag cta ctg cag gtg     1296
Thr Asp Leu Arg Gln Ile Val Thr Glu His Val Gln Leu Leu Gln Val
            420                 425                 430 atc aag aag acg gag aca gac atg agt ctt cac ccg ctc ctg cag gag     1344
Ile Lys Lys Thr Glu Thr Asp Met Ser Leu His Pro Leu Leu Gln Glu
        435                 440                 445 atc tac aag gac ttg tac tag                                          1365
Ile Tyr Lys Asp Leu Tyr
    450

<210> SEQ ID NO 5
<211> LENGTH: 454
<212> TYPE: PRT
<213> ORGANISM: Artificial
<220> FEATURE:
<223> OTHER INFORMATION: Synthetic Construct

<400> SEQUENCE: 5

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125
```

```
Ala Thr Ser Ser Ser Glu Glu Ser Ser Asn Lys Gly Gln Arg Gln Leu
    130             135             140
Thr Val Ser Pro Glu Phe Pro Gly Ile His Asn Ala Ile Arg Phe Gly
145             150             155             160
Arg Met Pro Gln Ala Glu Lys Glu Lys Leu Leu Ala Glu Ile Ser Ser
            165             170             175
Asp Ile Asp Gln Leu Asn Pro Glu Ser Ala Asp Leu Arg Ala Leu Ala
            180             185             190
Lys His Leu Tyr Asp Ser Tyr Ile Lys Ser Phe Pro Leu Thr Lys Ala
            195             200             205
Lys Ala Arg Ala Ile Leu Thr Gly Lys Thr Thr Asp Lys Ser Pro Phe
    210             215             220
Val Ile Tyr Asp Met Asn Ser Leu Met Met Gly Glu Asp Lys Ile Lys
225             230             235             240
Phe Lys His Ile Thr Pro Leu Gln Glu Gln Ser Lys Glu Val Ala Ile
                245             250             255
Arg Ile Phe Gln Gly Cys Gln Phe Arg Ser Val Glu Ala Val Gln Glu
            260             265             270
Ile Thr Glu Tyr Ala Lys Ser Ile Pro Gly Phe Val Asn Leu Asp Leu
    275             280             285
Asn Asp Gln Val Thr Leu Leu Lys Tyr Gly Val His Glu Ile Ile Tyr
    290             295             300
Thr Met Leu Ala Ser Leu Met Asn Lys Asp Gly Val Leu Ile Ser Glu
305             310             315             320
Gly Gln Gly Phe Met Thr Arg Glu Phe Leu Lys Ser Leu Arg Lys Pro
            325             330             335
Phe Gly Asp Phe Met Glu Pro Lys Phe Glu Phe Ala Val Lys Phe Asn
            340             345             350
Ala Leu Glu Leu Asp Asp Ser Asp Leu Ala Ile Phe Ile Ala Val Ile
            355             360             365
Ile Leu Ser Gly Asp Arg Pro Gly Leu Leu Asn Val Lys Pro Ile Glu
    370             375             380
Asp Ile Gln Asp Asn Leu Leu Gln Ala Leu Glu Leu Gln Leu Lys Leu
385             390             395             400
Asn His Pro Glu Ser Ser Gln Leu Phe Ala Lys Leu Leu Gln Lys Met
            405             410             415
Thr Asp Leu Arg Gln Ile Val Thr Glu His Val Gln Leu Leu Gln Val
            420             425             430
Ile Lys Lys Thr Glu Thr Asp Met Ser Leu His Pro Leu Leu Gln Glu
    435             440             445
Ile Tyr Lys Asp Leu Tyr
    450
```